(12) United States Patent
Myles et al.

(10) Patent No.: US 10,292,971 B2
(45) Date of Patent: May 21, 2019

(54) TETRAHYDRO-1H-PYRIDO[3,4-B]INDOLE ANTI-ESTROGENIC DRUGS

(71) Applicant: Olema Pharmaceuticals, Inc., San Francisco, CA (US)

(72) Inventors: David C. Myles, Berkeley, CA (US); Peter J. Kushner, San Francisco, CA (US); Cyrus L. Harmon, Bolinas, CA (US)

(73) Assignee: Olema Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 15/764,988

(22) PCT Filed: Sep. 29, 2016

(86) PCT No.: PCT/US2016/054549
§ 371 (c)(1),
(2) Date: Mar. 30, 2018

(87) PCT Pub. No.: WO2017/059139
PCT Pub. Date: Apr. 6, 2017

(65) Prior Publication Data
US 2018/0289679 A1  Oct. 11, 2018

Related U.S. Application Data

(60) Provisional application No. 62/235,900, filed on Oct. 1, 2015.

(51) Int. Cl.
| | | |
|---|---|---|
| *A61K 45/06* | (2006.01) | |
| *A61P 35/00* | (2006.01) | |
| *A61K 31/437* | (2006.01) | |
| *A61K 31/506* | (2006.01) | |
| *C07D 471/04* | (2006.01) | |
| *A61K 31/4545* | (2006.01) | |

(52) U.S. Cl.
CPC ........ *A61K 31/437* (2013.01); *A61K 31/4545* (2013.01); *A61K 31/506* (2013.01); *A61K 45/06* (2013.01); *A61P 35/00* (2018.01); *C07D 471/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 4,418,068 A | 11/1983 | Jones | |
| 4,659,516 A | 4/1987 | Bowler et al. | |
| 5,393,763 A | 2/1995 | Black et al. | |
| 5,457,117 A | 10/1995 | Black et al. | |
| 5,478,847 A | 12/1995 | Draper | |
| 5,780,497 A | 7/1998 | Miller et al. | |
| 5,880,137 A | 3/1999 | Miller et al. | |
| 5,998,402 A | 12/1999 | Miller et al. | |
| 6,005,102 A | 12/1999 | Raveendranath et al. | |
| 6,326,392 B1 | 12/2001 | Gast et al. | |
| 6,479,535 B1 | 11/2002 | Pickar et al. | |
| 6,512,002 B2 | 1/2003 | Lee et al. | |
| 6,583,170 B1 | 6/2003 | Pickar et al. | |
| 6,632,834 B2 | 10/2003 | Thompson et al. | |
| 6,756,401 B2 | 6/2004 | Day et al. | |
| 6,774,122 B2 | 8/2004 | Evans et al. | |
| 6,777,424 B2 | 8/2004 | Littman | |
| 6,821,989 B2 | 11/2004 | Rosati | |
| 7,456,160 B2 | 11/2008 | Evans et al. | |
| 8,299,112 B2 | 10/2012 | Smith et al. | |
| 8,455,534 B2 | 6/2013 | Smith et al. | |
| 8,703,810 B2 | 4/2014 | Kahraman et al. | |
| 8,853,423 B2 | 10/2014 | Govek et al. | |
| 9,018,244 B2 | 4/2015 | Kushner et al. | |
| 9,078,871 B2 | 7/2015 | Kahraman et al. | |
| 2001/0056099 A1 | 12/2001 | Day et al. | |
| 2002/0013327 A1 | 1/2002 | Lee et al. | |
| 2002/0016340 A1 | 2/2002 | Rosati | |
| 2002/0128276 A1 | 9/2002 | Day et al. | |
| 2005/0272759 A1 | 12/2005 | Moon et al. | |
| 2012/0238755 A1 | 9/2012 | Ueda et al. | |
| 2013/0178445 A1 | 7/2013 | Kushner et al. | |
| 2014/0357661 A1 | 12/2014 | Bradbury et al. | |
| 2015/0005286 A1 | 1/2015 | Smith et al. | |
| 2016/0175289 A1 | 6/2016 | Labadie et al. | |
| 2017/0362228 A1 | 12/2017 | Labadie et al. | |
| 2018/0002344 A1 | 1/2018 | Labadie et al. | |
| 2018/0235945 A1 | 8/2018 | Labadie et al. | |

FOREIGN PATENT DOCUMENTS

| | | |
|---|---|---|
| EP | 0802184 A1 | 10/1997 |
| WO | WO-1999/024027 A2 | 5/1999 |
| WO | WO-2002/003975 A2 | 1/2002 |
| WO | WO-2002/003976 A2 | 1/2002 |
| WO | WO-2002/003977 A2 | 1/2002 |
| WO | WO-2002/003986 A2 | 1/2002 |
| WO | WO-2002/003988 A2 | 1/2002 |
| WO | WO-2002/003989 A2 | 1/2002 |
| WO | WO-2002/003990 A2 | 1/2002 |
| WO | WO-2002/003991 A2 | 1/2002 |
| WO | WO-2002/003992 A2 | 1/2002 |

(Continued)

OTHER PUBLICATIONS

Blizzard, T.A. et al., Estrogen receptor ligands. Part 14: Application of novel antagonist side chains to existing platforms, Bioorganic & Medicinal Chemistry Letters, 15:5124-5128 (2005).

(Continued)

*Primary Examiner* — Joseph R Kosack
(74) *Attorney, Agent, or Firm* — Choate Hall & Stewart, LLP; Brenda Herschbach Jarrell; Michael A. Shinall

(57) ABSTRACT

The present disclosure provides tetrahydro-1H-pyrido[3,4-b]indole compounds or a pharmaceutically acceptable salt, solvate, hydrate, prodrug, stereoisomer, tautomer, rotamer, N-oxide and/or substituted derivative or, optionally in a pharmaceutical composition, for the modulation of disorders mediated by estrogen, or other disorders as more fully described herein.

29 Claims, 10 Drawing Sheets

(56) References Cited

FOREIGN PATENT DOCUMENTS

| WO | WO-2002/004418 A2 | 1/2002 |
|---|---|---|
| WO | WO-2002/013802 A2 | 2/2002 |
| WO | WO-2006/078834 A1 | 7/2006 |
| WO | WO-2008/127715 A1 | 10/2008 |
| WO | WO-2010/138695 A1 | 12/2010 |
| WO | WO-2010/138706 A1 | 12/2010 |
| WO | WO-2010/138758 A1 | 12/2010 |
| WO | WO-2011/156518 A2 | 12/2011 |
| WO | WO-2012/084711 A1 | 6/2012 |
| WO | WO-2013/090921 A1 | 6/2013 |
| WO | WO-2014/191726 A1 | 12/2014 |
| WO | WO-2014/203129 A1 | 12/2014 |
| WO | WO-2014/203132 A1 | 12/2014 |
| WO | WO-2014/205136 A1 | 12/2014 |
| WO | WO-2014/205138 A1 | 12/2014 |
| WO | WO-2016/097072 A1 | 6/2016 |
| WO | WO-2017/059139 A1 | 4/2017 |

OTHER PUBLICATIONS

De Savi, C. et al., Optimization of a Novel Binding Motif to (E)-3-(3,5-Difluoro-4-((1R,3R)-2-(2-fluoro-2-methylpropyl)-3-methyl-2,3,4,9-tetrahydro-1H-pyrido[3,4-b ]indol-1-yl)phenyl)acrylic Acid (AZD9496), a Potent and Orally Bioavailable Selective Estrogen Receptor Downregulator and Antagonist, J. of Med. Chem., 58 (20):8128-8140 (2015).

International Search Report for PCT/US2016/054549, 2 pages (dated Dec. 9, 2016).
Jordan, V.C., Alternate antiestrogens and approaches to the prevention of breast cancer, J. Cell Biochem. Suppl., 22:51-7 (1995).
Joseph, J.D. et al., The selective estrogen receptor downregulator GDC-0810 is efficacious in diverse models of ER+ breast cancer, Elife, 5. Pii: 15828 (2016).
Lai, A. et al, Identification of GDC-0810 (ARN-810), an Orally Bioavailable Selective Estrogen Receptor Degrader SERD) that Demonstrates Robust Activity in Tamoxifen-Resistant Breast Cancer Xenografts, J. Med Chem., 58(12): 4888-904 (2015).
Robertson, J. F. et al, Activity of fulvestrant 500 mg versus anastrozole 1 mg as first-line treatment for advanced breast cancer: results from the FIRST study, J. Clin. Oncol., 27(27):4530-5 (2009).
Sharma, A.P. et al, Structure-activity relationship of antiestrogens. Effect of the side chain and its position on the activity of 2,3-diaryl-2H-1-benzopyrans, J. Med. Chem., 33(12):3216-22 (1990).
Sharma, A.P. et al, Structure-activity relationship of antiestrogens. Phenolic analogues of 2,3-diaryl-2H-1-benzopyrans, J. Med. Chem., 33(12):3222-9 (1990).
Wakeling, A.E. et al, A Potent Specific Pure Antiestrogen with Clinical Potential, Cancer Research, 51(15):3867-3873 (1991).
Written Opinion for PCT/US2016/054549, 7 pages (dated Dec. 9, 2016).
Wu, Y.L. et al, Structural basis for an unexpected mode of SERM-mediated ER antagonism, Mol. Cell., 18(14): 413-24 (2005).
Fan, M. et al, Characterization of molecular and structural determinants of selective estrogen receptor downregulators, Breast Cancer Res. Treat, 103: 37-44 (2007).
Ullrich, J. W. and Miller, C. P., Estrogen receptor modulator review, Expert Opinion on Therapeutics Patents, 16(5): 559-572 (2006).

TETRAHYDRO-1H-PYRIDO[3,4-B]INDOLE ANTI-ESTROGENIC DRUGS

RELATED APPLICATIONS

This application is the U.S. national phase entry of PCT Application No. PCT/US2016/054549, filed Sep. 29, 2016, which claims priority to U.S. Provisional Application No. 62/235,900, filed Oct. 1, 2015. The entire contents of each application are incorporated by reference herewith in their entirety.

FIELD OF THE DISCLOSURE

This invention is in the field of pharmaceuticals, and is in particular novel tetrahydro-1H-pyrido[3,4-b]indole compounds and their medical uses, including as estrogen receptor modulators and for medical conditions that would benefit from an anti-estrogenic drug, and salts (including pharmaceutically acceptable salts), prodrugs and derivatives thereof and compositions thereof.

BACKGROUND

Estrogen receptor modulators are a class of compounds that act on the estrogen receptor. These compounds can be pure agonists (mimicking estrogen), pure antagonists, or mixed agonist-antagonists (sometimes referred to as Selective Estrogen Receptor Modulators (SERMs)). For example, estradiol is a pure agonist, fulvestrant is a complete antagonist, and tamoxifen and raloxifene are SERMs.

Most breast cancers express estrogen receptors (ER), and their growth is driven by the action of estrogen at its receptors, primarily at ER alpha. This type of cancer is treated with an estrogen receptor antagonist, which competes with estrogen for binding to the receptor, but does not activate it, preventing estrogen driven growth. Partial anti-estrogens such as raloxifene and tamoxifen retain some estrogen-like effects, including an estrogen-like stimulation of uterine growth, and also, in some cases, an estrogen-like action during breast cancer progression which stimulates tumor growth. In contrast, fulvestrant, a complete anti-estrogen, is free of estrogen-like action on the uterus and is effective in tamoxifen-resistant tumors. A recent study also suggests that fulvestrant is substantially superior to the aromatase inhibitor anastrozole in treating metastatic breast cancer (Robertson et al. J Clin Oncol (2009) 27(27):4530-5).

Estradiol is a naturally-occurring female estrogenic hormone. Raloxifene was disclosed by Eli Lilly in 1981 (U.S. Pat. Nos. 4,418,068; 5,478,847; 5,393,763; and 5,457,117) for prevention of breast cancer and treatment of osteoporosis. Fulvestrant was disclosed by Imperial Chemical Industries (ICI) in 1983 (U.S. Pat. No. 4,659,516, expired in 2007 with a patent term extension; U.S. Pat. Nos. 6,774,122 and 7,456,160). Tamoxifen was also disclosed by ICI in the '516 patent. Tamoxifen was developed for the treatment of breast cancer on the basis of strong antagonism of estrogen action in mammary tissue (Jordan, J. Cell. Biochem. 51 (1995)).

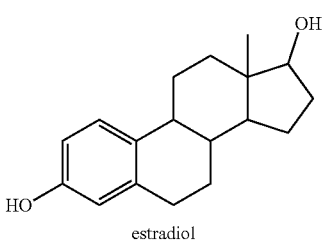

estradiol

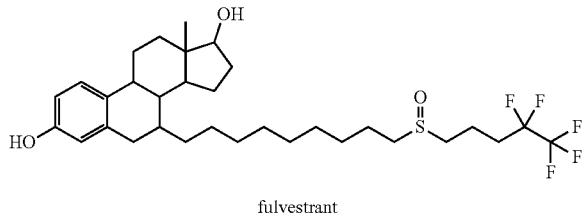

fulvestrant

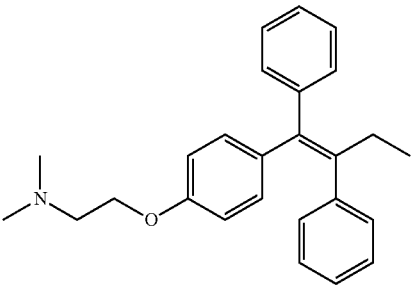

tamoxifen

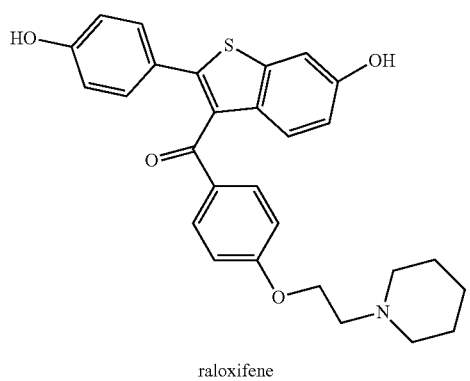

raloxifene

The degree of anti-estrogenicity is often assayed by exposing female, immature (preferably ovariectomized) rodents to test doses of the compound both in the absence (agonist mode) and presence (antagonist mode) of estrogen. Tamoxifen and other partial anti-estrogens stimulate uterine weight gain in the agonist mode and only partly block estrogen-driven uterine weight gain in the antagonist mode. Fulvestrant and other complete anti-estrogens do not stimulate uterine weight gain in the agonist mode and completely block estrogen-driven weight gain in the antagonist mode. The induction of estrogen-regulated alkaline phosphatase expression in human uterine cancer cell growth in culture can be used to distinguish partial and complete anti-estrogenicity and correlates well with the rodent weight gain assay. See U.S. Pat. No. 9,018,244.

Tamoxifen and fulvestrant both inhibit cultured human breast cancer cell proliferation provoked by estrogen. However, fulvestrant more fully inhibits the proliferation when provoked with growth factors, especially of the insulin/insulin-like growth factor family. Thus the inhibition of growth-factor driven breast cancer cell proliferation and the effect on uterine weight provide two assays which can distinguish between complete and partial anti-estrogens.

Compounds that act by degrading the estrogen receptor are sometimes referred to as "SERDs" (Selective Estrogen Receptor Degraders). While tamoxifen binding stabilizes the estrogen receptor, fulvestrant and chemically related antiestrogens, such as ICI-164384 and RU-58668, cause degradation of the estrogen receptor. The ability to induce degradation of the receptor is a factor that differentiates the behavior of tamoxifen and fulvestrant and may be desirable in a drug to treat breast cancer.

Fulvestrant incorporates a core of 17-beta estradiol. The estradiol core blocks oral absorption and the long flexible aliphatic side chain leads to poor solubility of the drug. Together, these aspects provide for poor oral bioavailabity of fulvestrant and the drug must be administered via injection. Two 5 ml intramuscular depot injections, one into each buttock, must be administered monthly by a health professional. Furthermore, it is unclear whether these two injections provide sufficient drug exposure for optimal action. The drug does not appear to work in pre-menopausal women.

Some compounds, such as GW-5638 (Wu et al, Mol Cell., 18, 413 (2005)), degrade the receptor but are partial estrogens, rather than complete anti-estrogens. Thus the ability to degrade the estrogen receptor does not ensure complete antiestrogenicity.

In 1990, a family of high-affinity benzopyran anti-estrogens was discovered by Kapil and coworkers. (Sharma et al. (1990) J Med Chem, 33(12):3222-9; Sharma et al. (1990) J Med Chem, 33(12):3216-22). This research resulted in the discovery of the drug candidate acolbifene.

In June 2011, Aragon Pharmaceuticals filed PCT/US2011/039669 (published Dec. 15, 2011 as WO2011/156518) which claimed priority to U.S. Provisional Application 61/353,531 titled "Estrogen Receptor Modulators and Uses Thereof." Aragon disclosed additional benzopyran derivatives and at least 71 acolbifene analogs for treatment of tamoxifen-resistant breast cancer. Patent filings assigned to Aragon also include U.S. Pat. Nos. 8,455,534 and 8,299,112. Aragon was acquired by Johnson & Johnson in 2013 for its line of prostate anti-androgen drugs, and Aragon continued with its anti-estrogenic developmental drugs under the name Seragon Pharmaceuticals, Inc. Seragon is now advancing SERD ARN-810 in clinical trials for postmenopausal women with locally advanced or metastatic estrogen receptor positive breast cancer. Patent filings by Seragon in this area include U.S. Pat. Nos. 9,078,871; 8,853,423; and 8,703,810; as well as US 2015/0005286 and WO 2014/205136 filed by Govek, et al., and WO 2014/205138 filed by Kahraman et al. Seragon was acquired by Genentech in 2014.

Kushner et al. in WO 2013/090921 and US2013/0178445, filed Dec. 17, 2012 and assigned to Olema Pharmaceuticals, describe OP-1038 (3-(4-hydroxyphenyl)-4-methyl-2-(4-{2-[(3R)-3-methylpyrrolidin-1-yl]ethoxy}phenyl)-2H-chromen-7-ol) and OP-1074 ((2S)-3-(4-hydroxyphenyl)-4-methyl-2-(4-{2-[(3R)-3-methylpyrrolidin-1-yl]ethoxy}phenyl)-2H-chromen-7-ol), as well as pharmaceutical compositions and methods of use. Additional patent filings by Olema in the area of anti-estrogenic compounds include WO 2014/203129 and WO 2014/203132.

Astra Zeneca is currently developing AZD9496 a novel, oral selective estrogen receptor down-regulator (SERD) in patients with estrogen receptor positive (ER+) breast cancer. See, WO 2014/191726. The structure of AZD9496 is illustrated below:

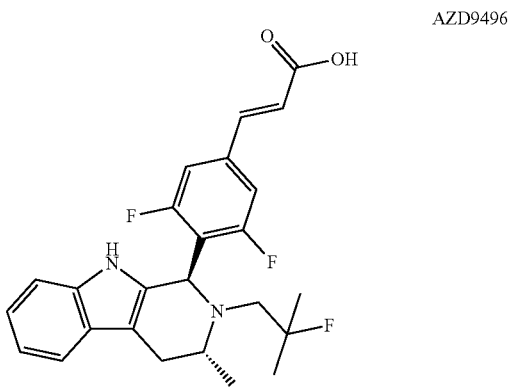 [SMILES: C[C@@H]1Cc2c([nH]c3ccccc23)[C@@H](c2c(F)cc(/C=C/C(=O)O)cc2F)N1CC(C)(C)F]

AZD9496

Additional indole, benzopyran, and 2H-chromene compounds are disclosed in WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497 and 5,880,137.

The object of the present invention is to provide new anti-estrogenic compounds with advantageous properties for the treatment of medical disorders that are mediated or affected by an estrogen receptor and pharmaceutical compositions and uses thereof.

SUMMARY OF THE INVENTION

The present invention provides specific tetrahydro-1H-pyrido[3,4-b]indole compounds of Formula I having advantageous properties for the treatment of medical disorders in a host, typically a human, that are modulated or affected by an estrogen receptor. These tetrahydro-1H-pyrido[3,4-b]indole compounds have a significant inhibitory effect on estrogen receptors at nanomolar concentration and have minimal residual estrogenic effects.

The present invention particularly provides two specific compounds, Compound B ((1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole) and Compound C ((1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole), whose structures are surprisingly different from prior compounds described in the art as being useful estrogen receptor antagonists, and in fact contain specific structural features that teachings in the art affirmatively indicated were undesirable. Specifically, Compounds B and C, unlike AZD9496, described above, lack the difluorophenyl bridge, as illustrated below.

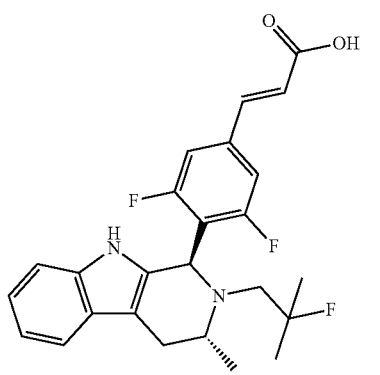

AZD9496

Compound B

Compound C

The present disclosure describes these Compounds B and C and various methods and compositions relating thereto. Furthermore, the present disclosure documents certain surprising and unexpected attributes of these compounds, even when compared with structurally similar agents. Compounds B and C are both encompassed within Formula I, provided by the present invention:

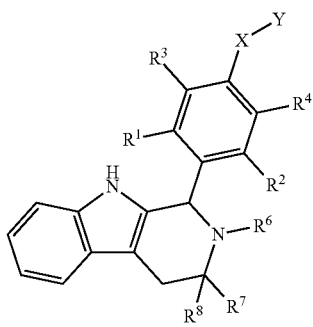

I wherein:
X is —CH$_2$— or —O—;

Y is

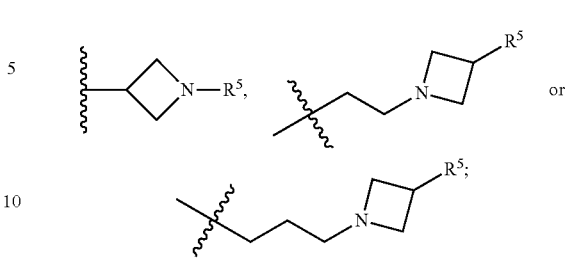

$R^1$, $R^2$, $R^3$ and $R^4$ are each independently selected from hydrogen or halo;

$R^5$ is hydrogen, $C_1$-$C_6$alkyl, $C_1$-$C_6$haloalkyl, $C_2$-$C_6$alkenyl, $C_0$-$C_4$($C_3$-$C_6$cycloalkyl) or $C_1$-$C_6$heteroalkyl;

$R^6$ is hydrogen, $C_1$-$C_6$alkyl, $C_1$-$C_6$haloalkyl or $C_0$-$C_4$($C_3$-$C_6$cycloalkyl);

$R^7$ and $R^8$ are each independently selected from hydrogen or $C_1$-$C_6$alkyl;

or a pharmaceutically acceptable salt or a composition thereof.

Compounds B and C, as documented herein, have particularly notable structural aspects, and furthermore are characterized by unexpected and desirable functional attributes, even with respect to other compounds having structures within the scope of Formula I.

As is readily apparent from the structures of Compounds B and C, each of $R^1$, $R^2$, $R^3$ and $R^4$ is H. In addition to describing the particular significance of Compounds B and C, the present disclosure specifically, and more generally, provides compounds of Formula I wherein each of $R^1$, $R^2$, $R^3$ and $R^4$ is H.

Particular compounds within Formula I that are exemplified herein include Compound A, which is (1R,3R)-2-(2-fluoro-2-methylpropyl)-1-(3-fluoro-4-((1-propylazetidin-3-yl)oxy)phenyl)-3-methyl-2,3,4,9-tetrahydro-1H-pyrido[3,4-b]indole, Compound B, which is (1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole, Compound C, which is (1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole, and Compound D, which is (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole.

The structures of Compound A, Compound B, Compound C, and Compound D are illustrated below.

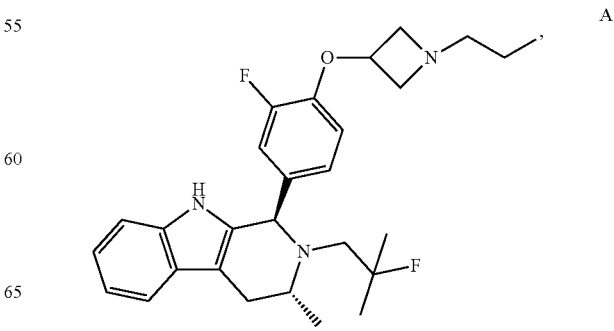

A

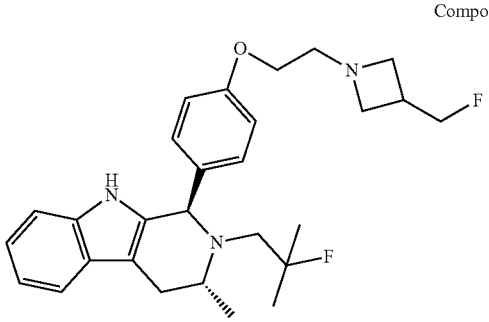

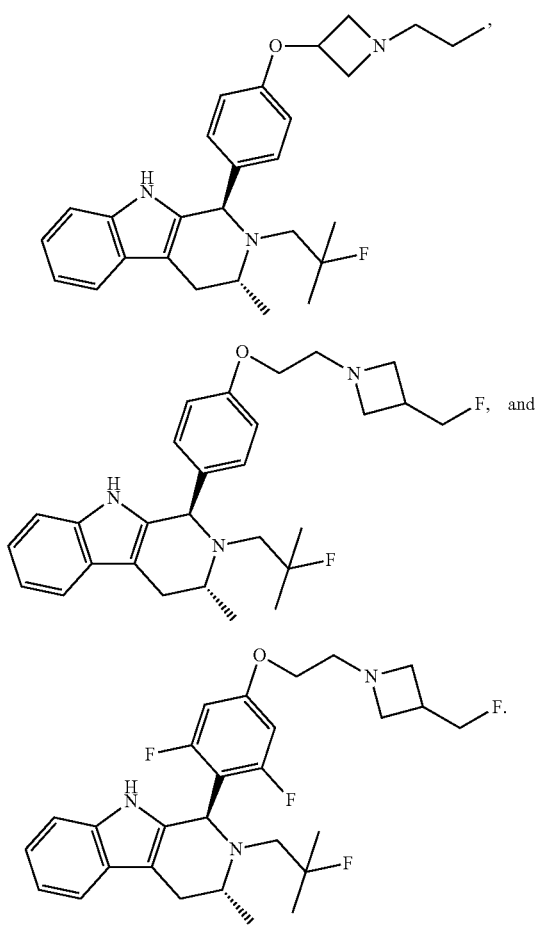

In each of these compounds,

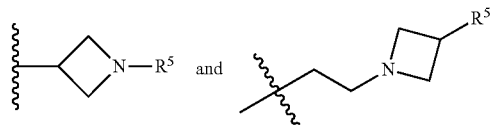

moieties are bonded to a tetrahydro-1H-pyrido[3,4-b]indole core via a phenyl or fluoro-substituted phenyl bridge. Of note, only one of these compounds, Compound D, includes a difluoro substitution of the type that the AstraZeneca disclosure teaches is critical. Compound D was reported by Goodacre, et al. in PCT Application Publication No. WO 2016/097072, and is otherwise referred to herein as "Goodacre Compound 102." Each of at least Compounds A-C, therefore, has a structure that explicitly lacks a moiety taught by the art as essential for estrogen receptor antagonists.

The present disclosure documents that each of Compounds A-D has certain advantageous anti-estrogen activities. For example, while AZD9496 is a potent inhibitor of E2-induced transcription in breast cells with an $IC_{50}=1.3$ nM and E2-stimulated proliferation in breast cells with an $IC_{50}=0.2$ nM, AZD9496 has approximately 10-fold greater estrogen-like activity as both an alkaline phosphatase (AP) agonist and antagonist in comparison to Compounds A-D. Advantageous activities of Compound A, Compound B, Compound C and Compound D are illustrated in Table 1.

TABLE 1

| Compound | ERE-Luc $IC_{50}$ (nM) | MCF-7 Proliferation $IC_{50}$ (nM) | AP Agonist Act. (% of E2) | AP Antagonist Act. (% of E2) |
|---|---|---|---|---|
| A | 2.96 | 7.58 | 3.96 | 3.15 |
| B | 4.35 | 4.53 | 2.18 | 1.96 |
| C | 10.7 | 14.5 | 3.1 | 2.5 |
| D | 10.0 | 8.4 | 3.37 | 4.07 |
| AZD9496 | 0.2 | 1.3 | 35 | 33 |

Compounds B and C show comparable activity to fulvestrant, an intramuscularly injected antiestrogen shown to be superior to other hormonal therapies for treating first line metastatic human breast cancer. Compounds B and C have potency similar to fulvestrant in blocking estrogen driven gene expression and proliferation of human breast cancer cells. The potency of Compounds B and C, therefore, is superior to AZD9496. See FIG. 2A.

The present disclosure exemplifies a variety of additional interesting and desirable activities for Compound B. For example, Compound B inhibited E2-induced transcription in breast cells with an $IC_{50}=4.35$ nM. Compound B also demonstrated inhibition of E2-stimulated proliferation in breast cells with an $IC_{50}=4.53$ nM. When ECC-1 cells were incubated with Compound B, the cells had only 2.18% of the AP activity that the cells would have if AP activity were normalized to the affect that 500 pM 17β-estradiol has on ECC-1 cells. When ECC-1 cells were co-treated with Compound B and 500 pM 17β-estradiol, the ECC-1 cells exhibited only 1.96% of the activity that 17β-estradiol would produce.

Compounds provided by the present invention can be prepared, if desired, as a pharmaceutically acceptable salt, solvate, hydrate, prodrug, stereoisomer, tautomer, rotamer, N-oxide or X, Y, $R^1$, $R^2$, $R^3$, $R^4$, $R^5$, $R^6$, $R^7$ and/or $R^8$ substituted derivative optionally in a pharmaceutically acceptable composition to treat a disorder that is modulated or affected by an estrogen receptor, including those treatable with an anti-estrogenic agent.

In certain embodiments, a compound is disclosed having Formula I(a):

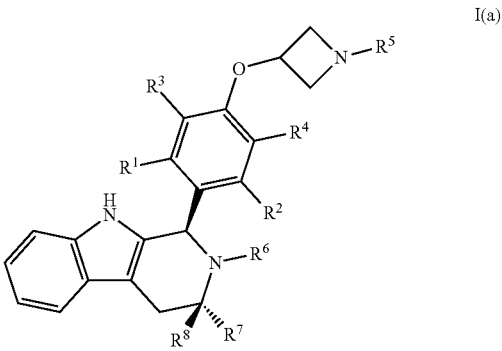

wherein:

$R^1$, $R^2$, $R^3$, $R^4$, $R^5$, $R^6$, $R^7$ and $R^8$ are as defined above;

or a pharmaceutically acceptable salt thereof.

In certain embodiments, a compound is disclosed having Formula I(b):

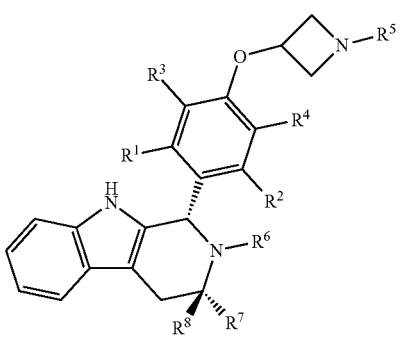

wherein:
$R^1$, $R^2$, $R^3$, $R^4$, $R^5$, $R^6$, $R^7$ and $R^8$ are as defined above;
or a pharmaceutically acceptable salt thereof.

In certain embodiments, a compound is disclosed having Formula I(c):

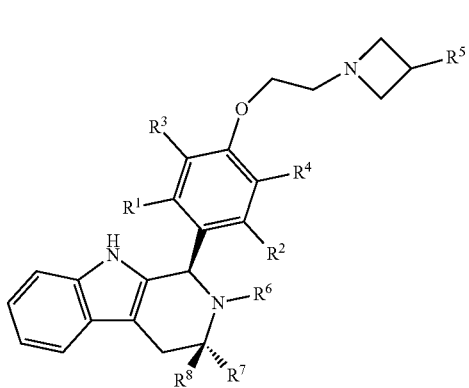

wherein:
$R^1$, $R^2$, $R^3$, $R^4$, $R^5$, $R^6$, $R^7$ and $R^8$ are as defined above;
or a pharmaceutically acceptable salt thereof.

In certain embodiments, a compound is disclosed having Formula I(d):

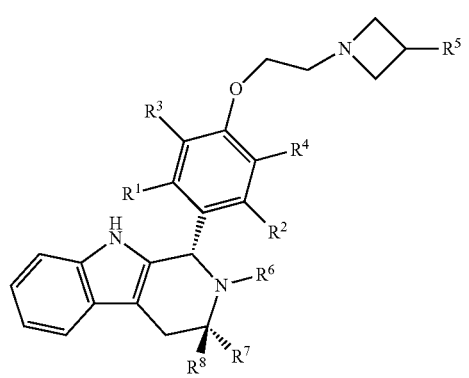

wherein:
$R^1$, $R^2$, $R^3$, $R^4$, $R^5$, $R^6$, $R^7$ and $R^8$ are as defined above;
or a pharmaceutically acceptable salt thereof.

Compounds provided by the present invention can be prepared as is or as a pharmaceutically acceptable salt, solvate, hydrate, prodrug, stereoisomer, tautomer, rotamer or N-oxide, optionally in a pharmaceutically acceptable composition, to treat a disorder that is modulated or affected by an estrogen receptor in a human or other host in need thereof. In some embodiments, a compound of Formula I is provided as a prodrug.

In some embodiments, a compound of Formula I has at least one isotopic substitution, and in particular, for example, at least one substitution of deuterium for hydrogen. In one embodiment, the deuterium can be bound in a location of bond breakage during metabolism (an α-deuterium kinetic isotope effect) or next to or near the site of bond breakage (a β-deuterium kinetic isotope effect).

Examples of disorders that can be treated with compounds described herein or their pharmaceutically acceptable salts, prodrugs, etc. or compositions thereof include, but are not limited to, local, advanced or metastatic breast cancer that is positive for expression of estrogen receptors, progesterone receptors or both. Compounds may be administered prior to surgery or following surgery to decrease the risk of recurrence or to treat remaining tumor. Compounds described herein are useful as adjunctive therapy after or instead of chemotherapy, radiation or surgery. They are also useful for the prevention of breast cancer in women at high risk for an estrogen modulated tumor or for the treatment of other cancers and overgrowth diseases of estrogen-receptive tissue, such as the female reproductive tract including ovarian, endometrial, and vaginal cancer and endometriosis.

In some embodiments, the cancer, such as breast cancer, is in a postmenopausal woman who has relapsed or progressed following therapy. In other embodiments, the cancer, such as breast cancer in a postmenopausal woman, has progressed in the presence of endocrine therapy. In yet other embodiments, the cancer, including in a postmenopausal woman, has previously progressed in the presence of therapy with an aromatase inhibitor, such as aminoglutethimide, testolactone, anastrozole, letrozole, exemestane, vorozole, formestane, fadrozole, 4-hydroxyandrostenedione, 1,4,6-androstatrien-3,17-dione, or 4-androstene-3,6,17-trione. In some embodiments, the aromatase inhibitor is anastrozole, letrozole, or exemestane.

In some embodiments, a compound of the present invention is used to treat estrogen or progesterone receptor negative breast cancer.

Compounds provided herein can be used as the initial treatment of an estrogen modulated tumor for example, in patients who have never received previous hormonal therapy for advanced breast cancer, either by itself or in combination with one or more other anti-cancer agents, including targeted therapies, for example, a targeted therapy such as an mTOR inhibitor such as everolimus or rapamycin, a CDK4/6 inhibitor such as palbociclib (PD-0332991) (Pfizer), Abemaciclib (LY2835219) (Lilly) or LEE001 (Novartis), herceptin, an antibody to or inhibitor of PD-1, PD-L1, or CTLA-4, or an inhibitor of or antibody to EGFR, PGFR or IGFR. Administration in combination can proceed by any technique apparent to those of skill in the art including, for example, separate, sequential, concurrent or alternating administration.

Compounds provided by the present invention are also useful as adjuvant therapy after surgery to prevent recurrence. Such adjuvant use is often administered for several years, for instance up to 5 years, or 10 years after surgery and/or associated chemotherapy and radiotherapy have been concluded.

Compounds provided by the present invention are useful for the prevention of breast cancer in women at high risk and can be taken for any desired time period, including indefinitely. For example, a patient, typically a woman, with a family history of breast cancer, or who has been determined to carry a mutation in the BRCA1 or BRCA2 or other gene that predisposes a patient to breast cancer may choose to use such preventative treatment instead of a mastectomy or other intervention. Compounds described herein are also useful as neoadjuvants to shrink large tumors prior to surgical removal, both to enable breast conservative surgery and to reduce the risk of recurrence.

Selective estrogen receptor modulators (SERMs) are also useful for hormonal therapy for postmenopausal women in particular to treat or prevent osteoporosis. In some embodiments, a compound of the present invention is used to treat osteopenia, osteoporosis, or a related bone disorder, optionally in combination with an estrogen, SERM or partial anti-estrogen such that the anti-estrogen prevents adverse action of the total or partial estrogen on the uterus and other tissues.

Other objects and advantages will become apparent to those skilled in the art from a consideration of the ensuing detailed description. All variations and modifications of the disclosed invention are considered within the scope of this invention.

The present invention includes at least the following features:

(a) a compound of Formula I as described herein, and a pharmaceutically acceptable salt solvate, hydrate, prodrug, stereoisomer, tautomer, rotamer or N-oxide thereof (each of which and all subgenuses and species thereof considered individually and specifically described);

(b) a compound of Formula I as described herein, and a pharmaceutically acceptable salt solvate, hydrate, prodrug, stereoisomer, tautomer, rotamer or N-oxide thereof for use in treating or preventing disorders modulated or affected by an estrogen receptor in a human or other host in need thereof and other disorders described further herein;

(c) use of a compound of Formula I, and a pharmaceutically acceptable salt, solvate, hydrate, prodrug, stereoisomer, tautomer, rotamer or N-oxide in the manufacture of a medicament for use in treating or preventing a disorder that is modulated or affected by an estrogen receptor in a human or other host in need thereof and other disorders described further herein;

(d) a process for manufacturing a medicament intended for the therapeutic use for treating or preventing disorders modulated or affected by an estrogen receptor in a human or other host in need thereof and other disorders described further herein characterized in that a compound of Formula I as described herein is used in the manufacture;

(e) a pharmaceutical formulation(s) comprising an effective host-treating amount of a compound of Formula I or a pharmaceutically acceptable salt, solvate, hydrate, prodrug, stereoisomer, tautomer, rotamer or N-oxide thereof together with a pharmaceutically acceptable carrier or diluent;

(f) a compound of Formula I as described herein in substantially pure form, including substantially isolated from other chemical entities (e.g., at least 90 or 95%);

(g) processes for the manufacture of compounds of Formula I and salts, compositions, dosage forms thereof; and (h) processes for the preparation of therapeutic products that contain an effective amount of a compound of Formula I, as described herein.

DETAILED DESCRIPTION OF THE INVENTION

Figure 1A:
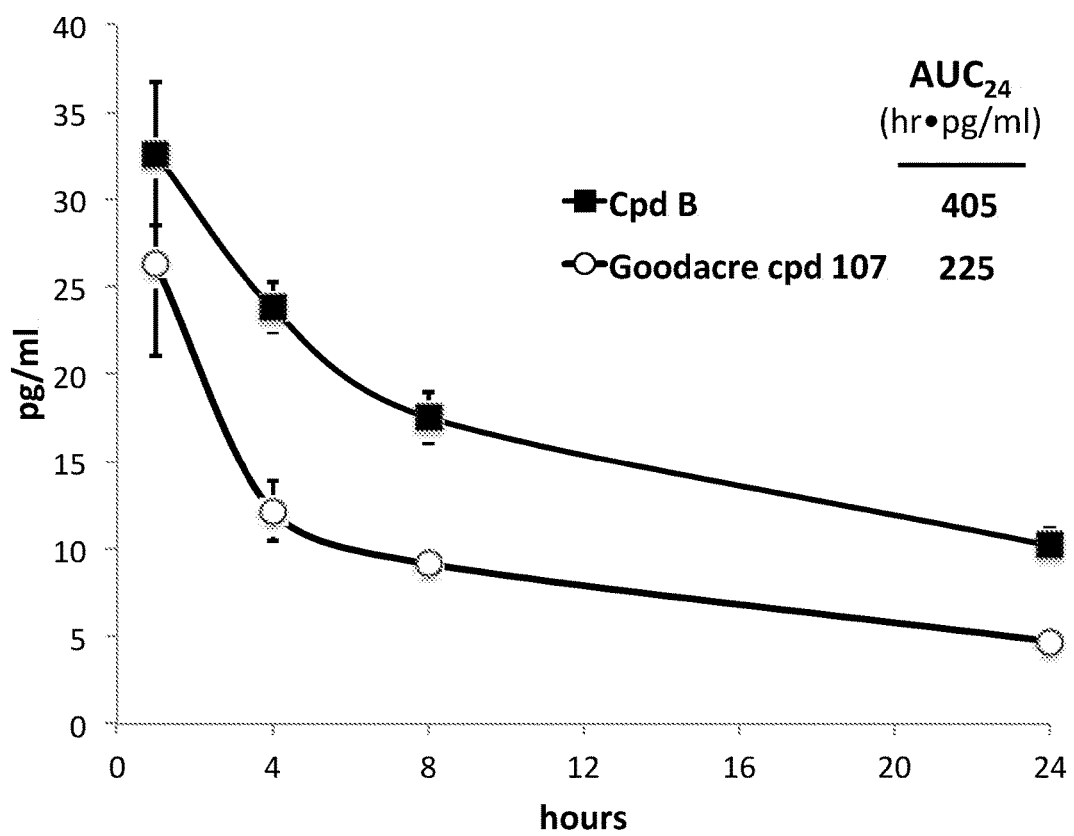
FIG. 1A is a plot of the free drug concentration in BALB/c mice, at a dosage of 5 mg/kg for Compound B and Goodacre Compound 107. The x-axis depicts time in hours, and the y-axis depicts the concentration in pg/ml.

Efforts to develop treatments for disorders such as breast cancer focus on interactions with estrogen receptors to ultimately inactivate the receptor, either through competitive binding, or through degradation of the receptor. Compounds that compete with estrogen for receptor binding, and inhibit receptor activity, are known as "antiestrogens."

Recent development of antiestrogens by AstraZeneca has focused around the compound AZD9496, which recently entered clinical trials. See PCT Application Publication No. WO 2014/191726.

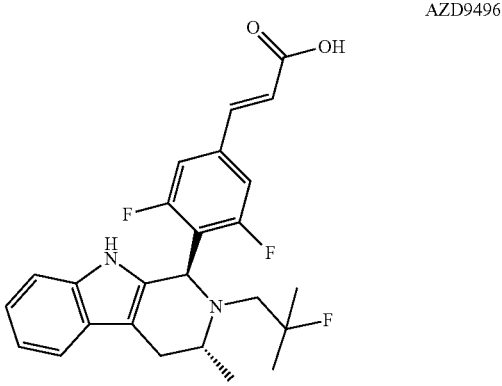 [SMILES: C[C@@H]1Cc2c([nH]c3ccccc23)[C@@H](c2c(F)cc(/C=C/C(=O)O)cc2F)N1CC(C)(C)F]

AZD9496

AZD9496 comprises a difluorophenyl bridge, which was unlike other antiestrogens in development at the time. AstraZeneca demonstrated, however, that this difluorophenyl bridge was necessary for increasing potency overall (e.g., as assessed by one or more of increased binding to isolated receptor, enhanced degradation of the estrogen receptor, more effective inhibition of estrogen-induced expression of the progesterone receptor gene, and/or increased inhibition of proliferation of human breast cancer cell). Potency of compounds with the difluorophenyl bridge was found to be 5- to 10-fold higher than that of analogous compounds which lacked the difluorophenyl bridge. See PCT Application Publication No. WO 2014/191726, Table A (page 29). Specifically, AstraZeneca documented that compound AZD9496 (Example 1), has better ER binding $IC_{50}$ and ER down regulation $IC_{50}$ values than Example 2, depicted below, which lacks the difluorophenyl bridge.

Therefore, as these two compounds (AZD9496 and Example 2 from WO 2014/191726) are structurally identical to one another except for the difluoro substitution, the teachings provided by AstraZeneca clearly indicate that difluoro substitution is necessary for overall potency and/or activity.

In light of these findings, subsequent development of antiestrogens tended to incorporate the same or similar difluorophenyl linkers into compounds. For example, a patent application filed by Genentech and directed to structurally similar compounds was published on Jun. 23, 2016. See PCT Application Publication No. WO 2016/097072. While the genera described therein are broad, almost all of

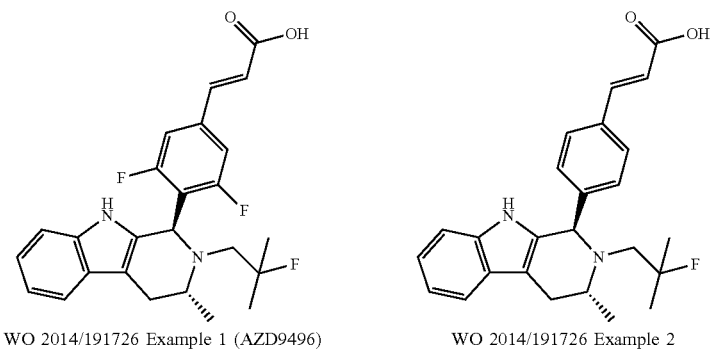

WO 2014/191726 Example 1 (AZD9496)    WO 2014/191726 Example 2

| WO 2014/191726 Example | ER binding $IC_{50}$ value | ER down regulation $IC_{50}$ value |
| --- | --- | --- |
| 1 | <0.64 | 0.14 |
| 2 | 1 | 0.85 |

Further, a published study by De Savi, et al., confirms the significance of the difluorophenyl bridge in the AstraZeneca compounds. See De Savi, et al. "Optimization of a Novel Binding Motif to (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic Acid (AZD9496), a Potent and Orally Bioavailable Selective Estrogen Receptor Downregulator and Antagonist," *J. of Med. Chem.*, 58 (20):8128-8140 (2015) (hereinafter "De Savi"). There, the authors compared compound 30b (corresponding to AZD9496) to a number of compounds including compound 29b (corresponding to Example 2 from WO 2014/191726) to assess ER binding, ER downregulation, PR agonism, PR antagonism, and MCF7 antiproliferation. See De Savi, supra, page 8130, Table 1. There, De Savi reported data illustrating that the presence of the fluoro substitution on the phenyl bridge was necessary for potency in these assays, as shown in an excerpt of Table 1, provided below:

| Entry | ER binding $pIC_{50}$ | ER downregulation $pIC_{50}$ | PR agonist $pIC_{50}$ | PR antagonism $pIC_{50}$ | MCF antiproliferation $pIC_{50}$ |
| --- | --- | --- | --- | --- | --- |
| 29b | 9 (±0.11) | 9.07 (±0.08) | <5.5 | 8.46 (±0.12) | 9.49 (±0.15) |
| 30b | 9.17 (±0.07) | 9.86 (±0.03) | <5.5 | 9.55 (±0.06) | 10.4 (±0.05) | the reported compounds comprise the same difluorophenyl moiety, such as Compounds 102 and 107 (also referred to as "Goodacre Compound 102" and "Goodacre Compound 107," respectively, below). See PCT Application Publication No. WO 2016/097072, Tables 1 and 2 on page 33, et seq. Goodacre Compound 102 is also referred to as "Compound D" above.

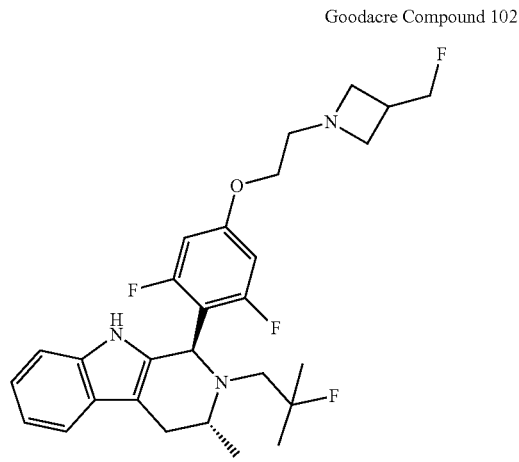

Goodacre Compound 102

Goodacre Compound 107

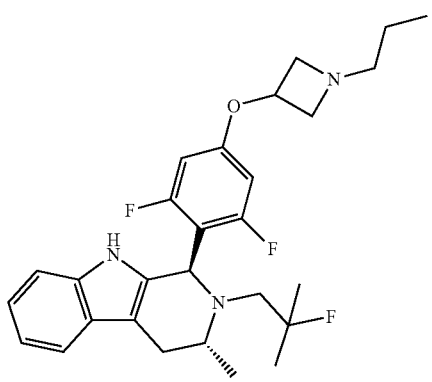

The present disclosure further discloses certain advantageous anti-estrogen activities of Compounds B and C. Advantageous activities of Compound B and Compound C as compared to Fulvestrant, AZD9496, and Goodacre Compounds 102 and 107 are illustrated in Table 2 and Table 3.

Accordingly, the present invention is based on the discovery that specific tetrahydro-1H-pyrido[3,4-b]indole compounds of Formula I (in the form of a mixture of stereoisomers and also the pure enantiomers) have advantageous properties for the treatment of medical disorders that are modulated or affected by an estrogen receptor.

The present invention particularly provides two specific compounds, Compound B ((1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole) and Compound C ((1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole), whose structures are surprisingly different from prior compounds described in the art as being useful estrogen receptor antagonists, and in fact contain specific structural features that teachings in the art affirmatively indicated were undesirable. Specifically, Compounds B and C, unlike AZD9496, and Goodacre Compounds 102 and 107 described above, lack the difluorophenyl bridge, as illustrated below.

TABLE 2

| | Induction of Alkaline Phosphatase (AP) | | | Inhibition of E2-stimulated AP (at 100 nM dose) | | | Inhibition of E2-stimulated transcription in breast cells | | | Inhibition of E2-stimulated proliferation in breast cells | | |
|---|---|---|---|---|---|---|---|---|---|---|---|---|
| | n | % E2 | SD | n | % E2 | SD | n | pIC$_{50}$ | SD | n | pIC$_{50}$ | SD |
| Fulvestrant | 53 | −0.04 | 1.36 | 53 | −0.09 | 1.28 | 41 | 8.72 | 0.24 | 45 | 8.58 | 0.25 |
| AZD-9496 | 14 | 39 | 13 | 12 | 39.1 | 16.7 | 12 | 9.20 | 0.28 | 16 | 8.73 | 0.31 |
| Compound B | 21 | 1.78 | 1.22 | 19 | 1.56 | 1.23 | 20 | 8.36 | 0.25 | 25 | 8.11 | 0.17 |
| Goodacre Compound 107 | 7 | 0.00 | 1.49 | 7 | 1.03 | 0.94 | 5 | 8.36 | 0.25 | 8 | 8.12 | 0.08 |
| Compound C | 10 | 1.71 | 1.71 | 8 | 1.76 | 0.80 | 11 | 8.09 | 0.14 | 14 | 7.93 | 0.13 |
| Goodacre Compound 102 | 5 | 4.45 | 2.95 | 4 | 3.98 | 0.50 | 7 | 8.02 | 0.16 | 7 | 7.98 | 0.06 |

As can be seen from Table 2, Compounds B and C show improved AP antagonist activity (i.e, are more complete antiestrogens) relative to AZD9496 and to Goodacre Compound 102. Of note, Goodacre Compound 102, which structure includes the difluoro substitution taught by AstraZeneca to be essential to activity, shows the worst AP agonist and antagonist activity.

Figure 1B:
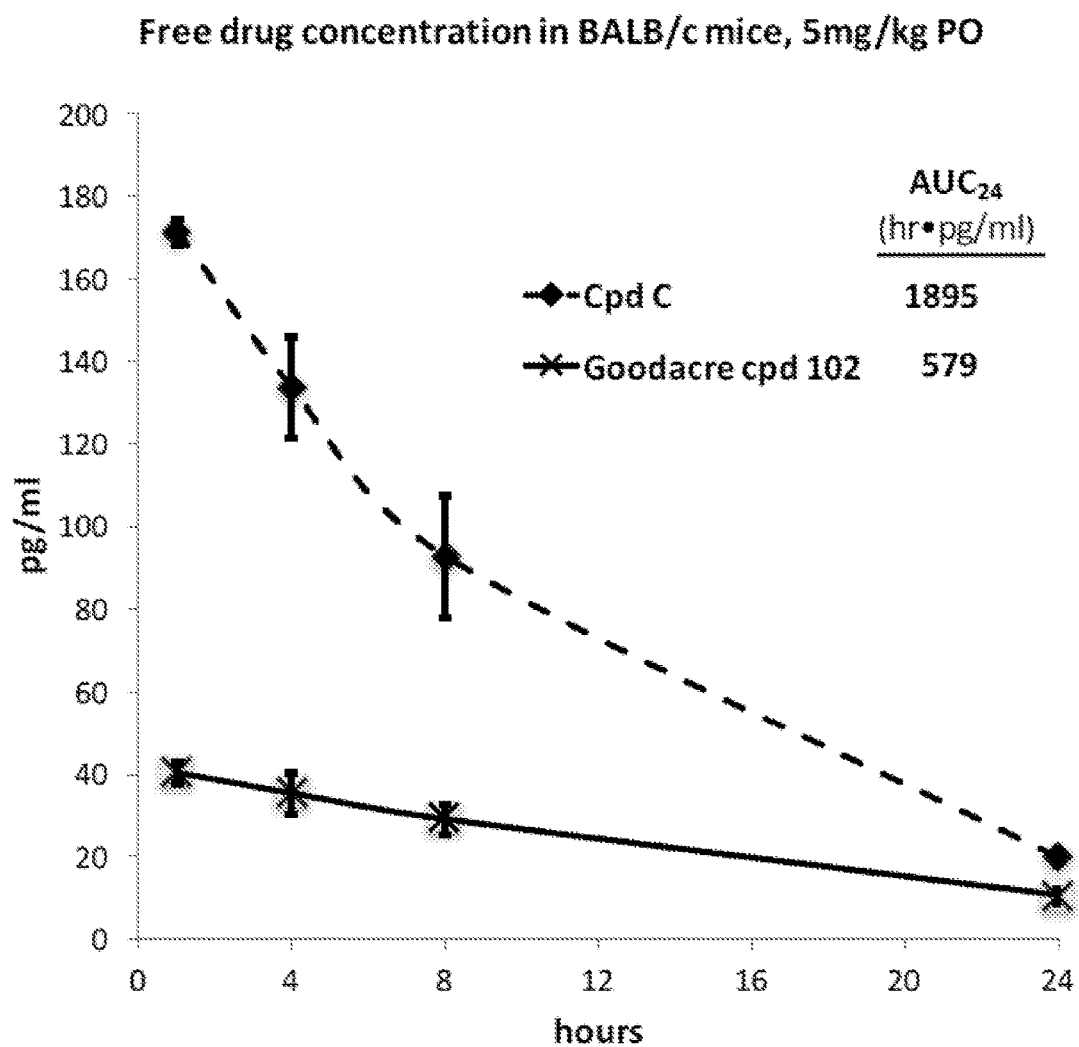
FIG. 1B is a plot of the free drug concentration in BALB/c mice, at a dosage of 5 mg/kg for Compound C and Goodacre Compound 102. The x-axis depicts time in hours, and the y-axis depicts the concentration in pg/ml.
Figure 2:
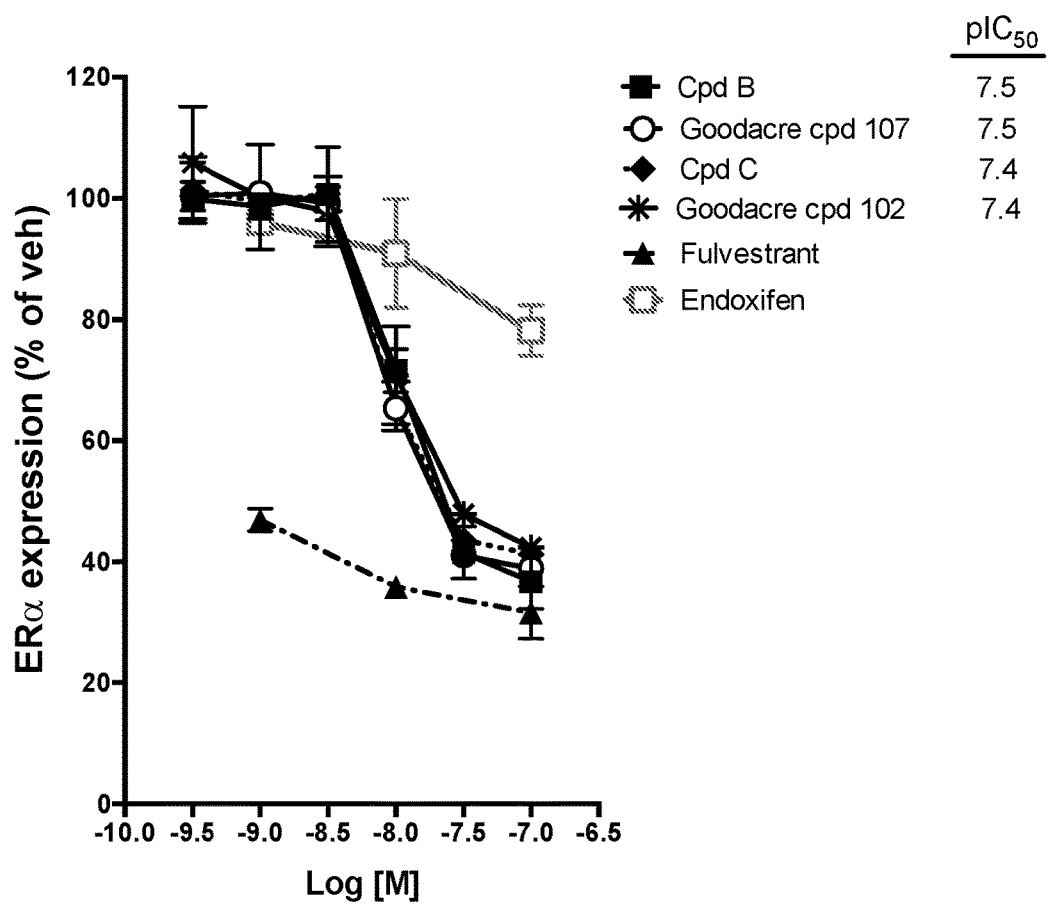
FIG. 2 is a plot of the amount of estrogen-receptor α (ER-α) expression % compared to the concentration of compound provided, measured logarithmically.

Even more importantly, Compounds B and C, which lack the difluorophenyl bridge, exhibit a higher free fraction in mouse and human plasma than Goodacre Compounds 102 and 107, structurally similar compounds that contain the difluorophenyl bridge. When each of these compounds is delivered to mice by oral gavage, and when free fraction is taken into account Compound B and Compound C have a substantially higher oral drug exposure than an equal dose of Compounds 107 and 102 (FIGS. 1A-1B). Compound B and Compound C are of similar potency in binding to isolated estrogen receptor alpha (Table 3), in degrading estrogen receptor alpha (FIG. 2), and in blocking estrogen driven breast cancer cell gene expression (FIG. 3) and proliferation (FIG. 4) when compared to Goodacre Compounds 102 and 107. In total, the observations of equivalent or superior potency of Compounds B and C combined with the observations of superior free drug exposure per identical dose indicate that Compounds B and C are likely to be more effective than Goodacre Compounds 102 and 107 per unit of oral dose in blocking estrogen receptor driven pathological conditions such as estrogen-driven breast cancer.

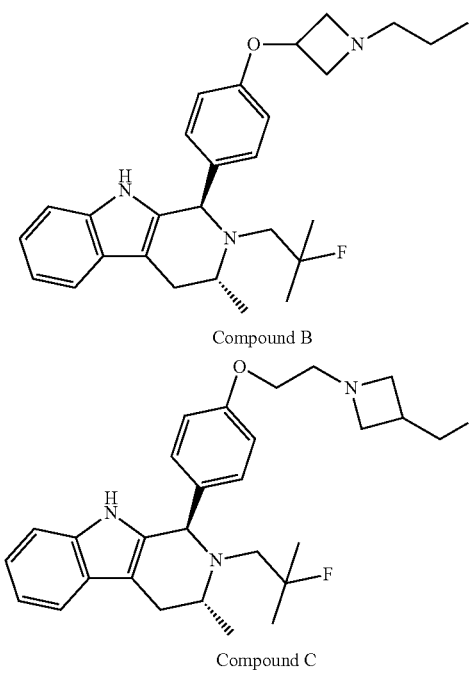

Compound B

Compound C

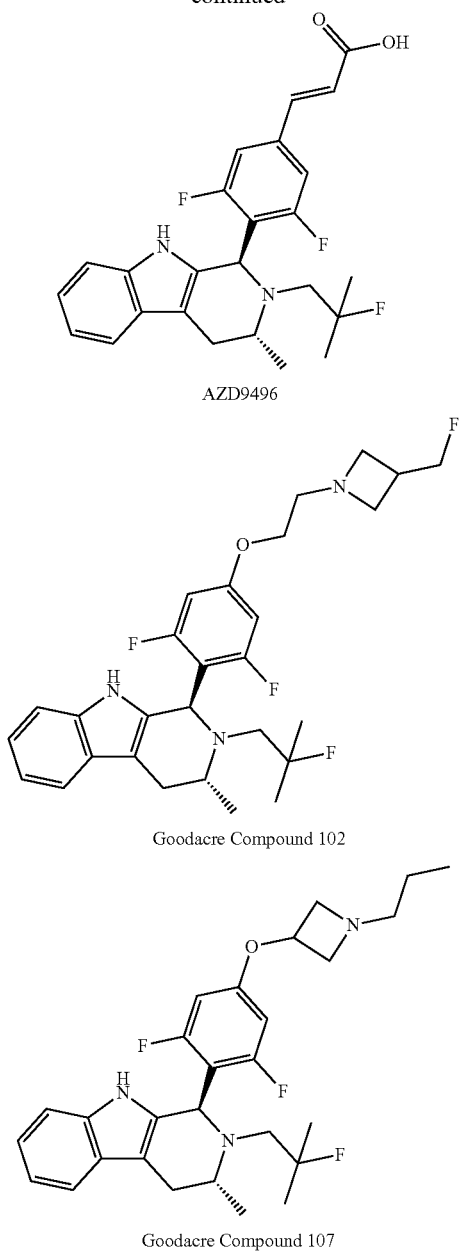

AZD9496

Goodacre Compound 102

Goodacre Compound 107

TABLE 3

|  | Relative change in ERα levels in breast cells | | % free drug in | | ERα binding |
|---|---|---|---|---|---|
|  | % | | plasma | | |
|  | n | Veh | pIC$_{50}$ | human | mouse | pIC$_{50}$ |
| Fulvestrant | 40 | 28 | 8.64 | 0.001 |  | 8.64 |
| AZD-9496 | 15 | 49 | 9.43 | 0.308 | 0.214 | 9.43 |
| Compound B | 13 | 45 | 8.57 | 0.036 | 0.027 | 8.57 |
| Goodacre Compound 107 | 4 | 44 | 8.55 | 0.013 | 0.012 | 8.55 |
| Compound C | 9 | 42 | 8.87 | 0.151 | 0.092 | 8.87 |
| Goodacre Compound 102 | 4 | 46 | 8.79 | 0.044 | 0.036 | 8.79 |

The present disclosure describes these Compounds B and C and various methods and compositions relating thereto. Furthermore, the present disclosure documents certain surprising and unexpected attributes of these compounds, even when compared with structurally similar agents.

Specifically, it has been found that compounds that lack the difluoro substituted phenyl bridge present in the patent applications presented by AstraZeneca (PCT Application Publication No. WO 2014/191726) and Genentech (PCT Application Publication No. WO 2016/097072) are potent in blocking estrogen driven gene induction and estrogen driven human breast cancer proliferation, as illustrated above in Table 1 as well as in FIGS. 5A-5B.

As others have noted, particularly in the field of estrogen receptor antagonists, moieties which have been found to enhance antagonist activity in individual SERMs are not necessarily interchangeable among structurally distinct compound cores. For example, as noted by Blizzard, et al., the use of a specific side chain found to increase potency in their platform was found to have no effect on the potency of other estrogen receptor antagonists. See Blizzard, et al., "Estrogen receptor ligands. Part 14: Application of novel antagonist side chains to existing platforms," *Bioorganic & Medicinal Chemistry Letters*, 15:5124-5128 (2005).

The present disclosure further demonstrates that compounds of the present invention act as complete antiestrogens (e.g., in that they completely block the ability of estrogen to regulate the expression of target genes and cellular responses in all cell types, including uterine cells). Those skilled in the art are aware of assays relied upon in the field to demonstrate or assess degree of antiestrogen activity. For example, the well-established rodent uterine weight gain assay (see, for example, Wakeling et al., 1991, *A Potent Specific Pure Antiestrogen with Clinical Potential, Cancer Research* 51, 3867-3873), is commonly used to assess degree of antiestrogen activity. Also, induction of alkaline phosphatase gene activity in human uterine cells grown in culture correlates well with the rodent uterine weight gain assay and can be used as an in vitro assay to distinguish between partial and complete antiestrogens. See U.S. Pat. No. 9,018,244. Those skilled in the art are also aware that complete antiestrogen activity is typically considered to be desirable in compounds to be utilized as active pharmaceutical ingredients in drug products. For example, fulvestrant, which is currently marketed under the trade name FASLODEX® for treatment of hormone-receptor-positive metastatic breast cancer in postmenopausal women with disease progression following antiestrogen therapy, is heralded as a pure antiestrogen with no intrinsic estrogen-like properties based at least in part on its performance in the rodent uterine weight gain assay. (see, for example, Wakeling et al., 1991, *A Potent Specific Pure Antiestrogen with Clinical Potential, Cancer Research* 51, 3867-3873).

By contrast, however, many other compounds reported to have antiestrogen character or activity, including those described by AstraZeneca as discussed above, and endoxifen, an active metabolite of the well-established breast cancer drug tamoxifen, show only incomplete antiestrogen activity in standard assays.

Figure 3:
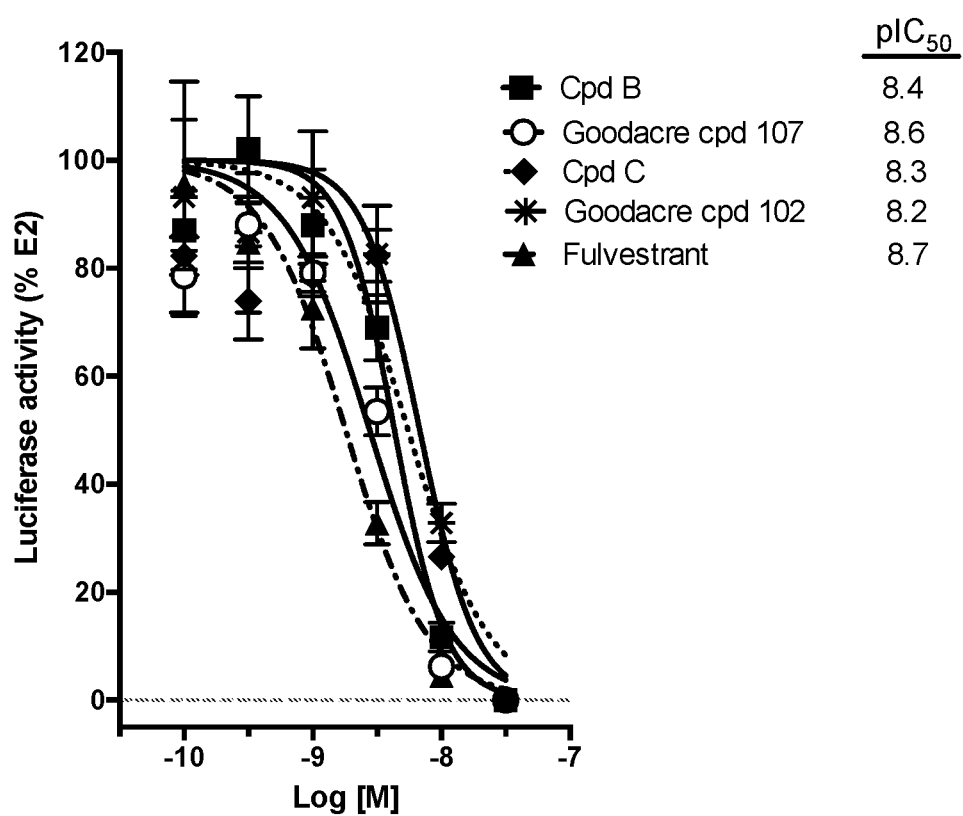
FIG. 3 is a plot of the amount luciferase activity % compared to the concentration of compound provided, measured logarithmically.
Figure 4:
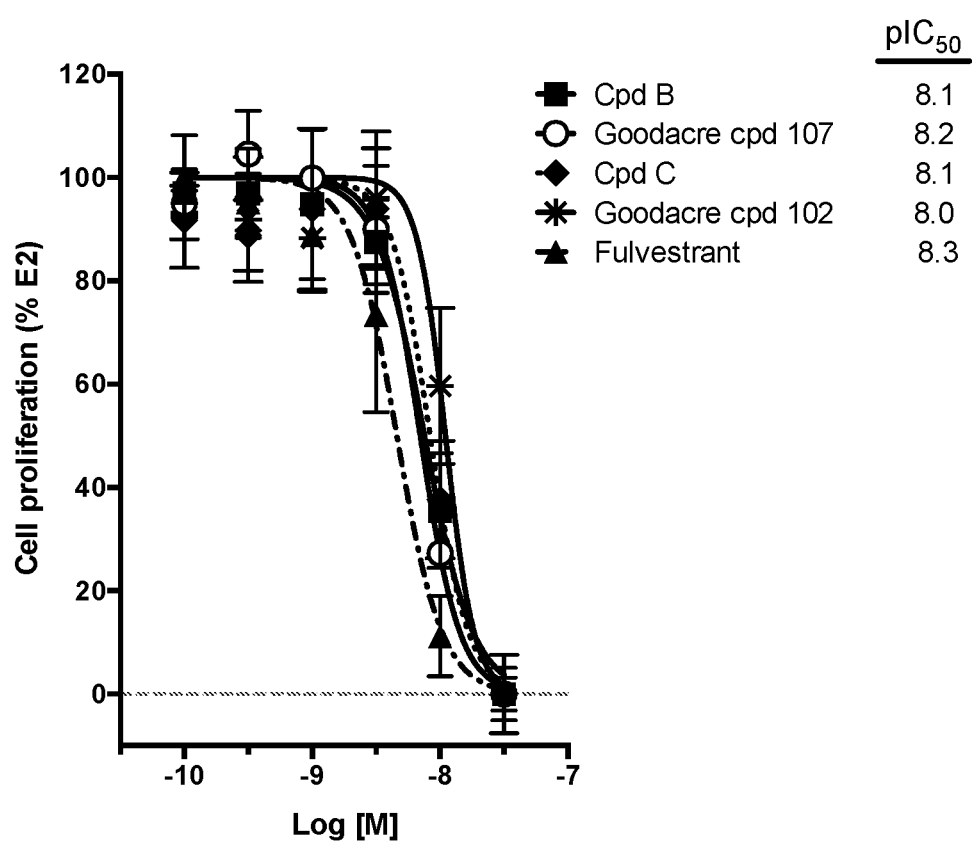
FIG. 4 is a plot of the amount of cell proliferation % compared to the concentration of compound provided, measured logarithmically.
Figure 5A:
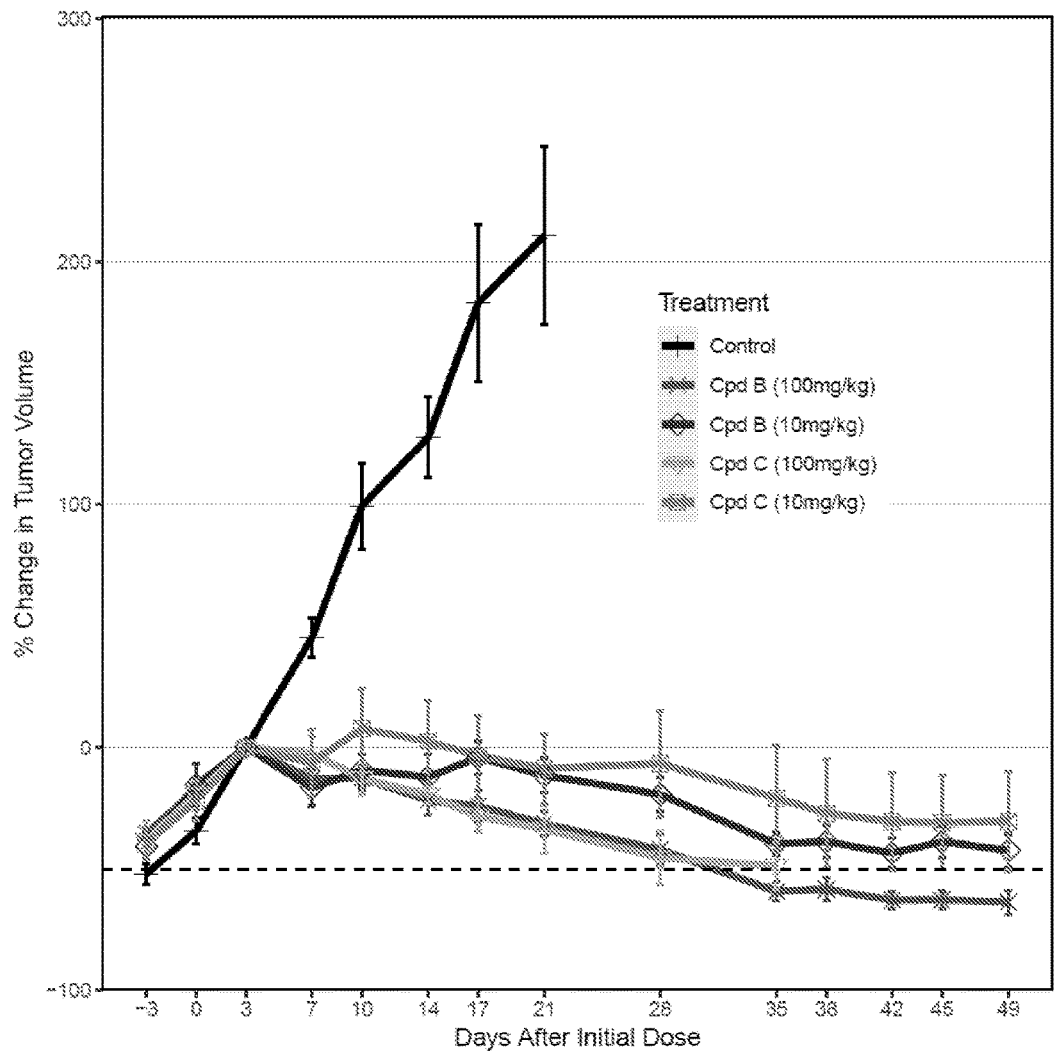
FIG. 5A is a plot measuring the % change in tumor size in xenografted mice after 49 days.
Figure 5B:
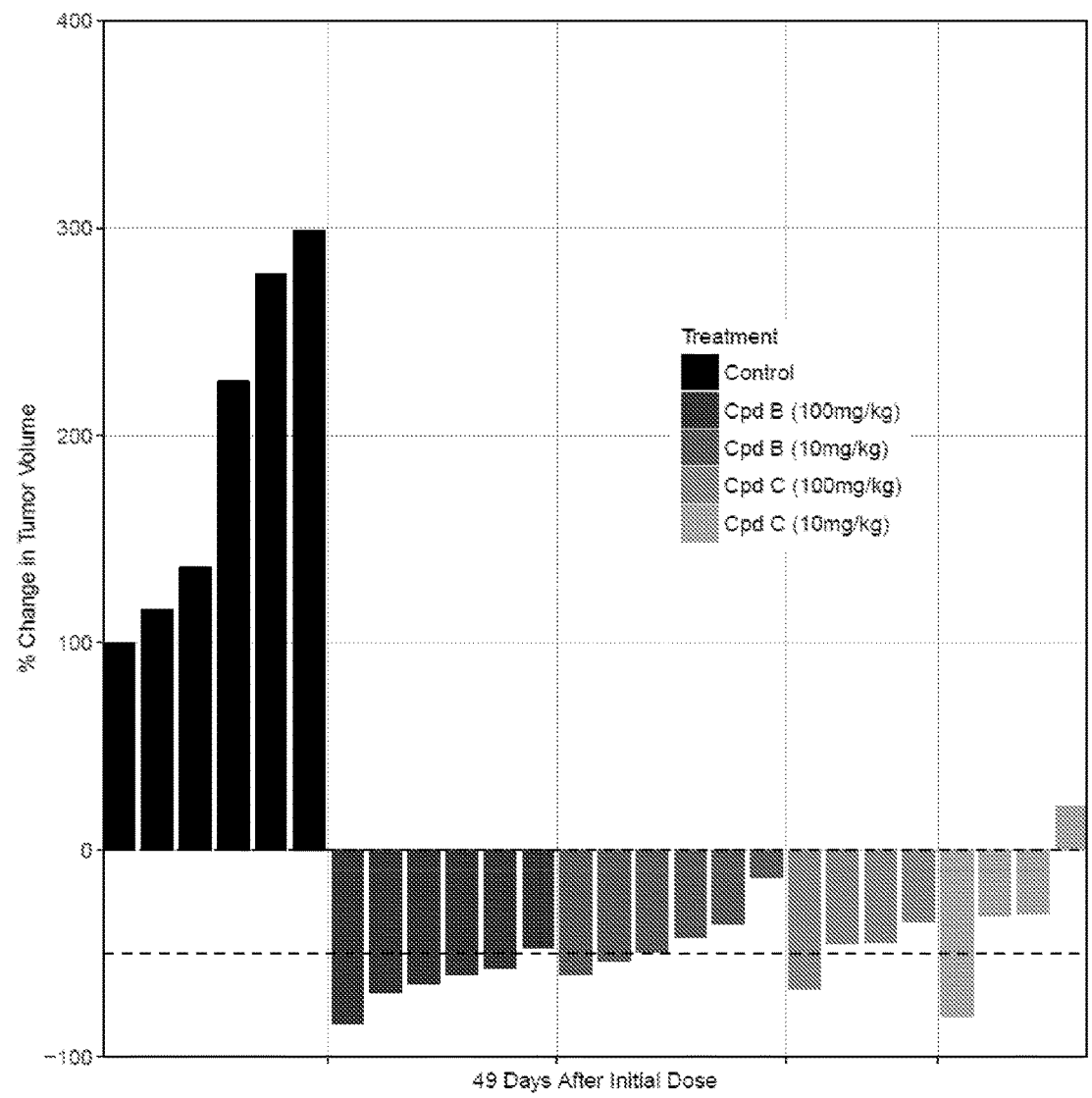
FIG. 5B is a waterfall plot measuring the % change in tumor size in xenografted mice after 49 days.
Figure 6A:
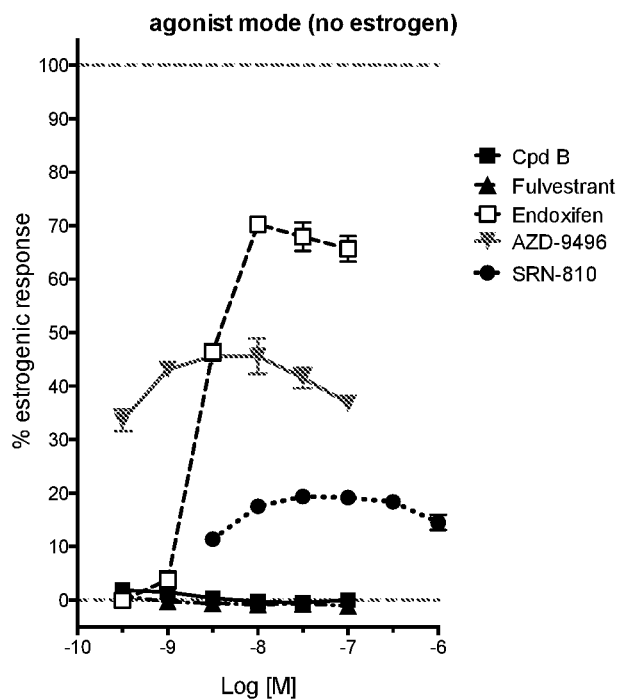
FIG. 6A is a plot of the % estrogenic response in for the compounds depicted within as agonists without the presence of estrogen, as compared to the concentration of the depicted compound, measured logarithmically.
Figure 6B:
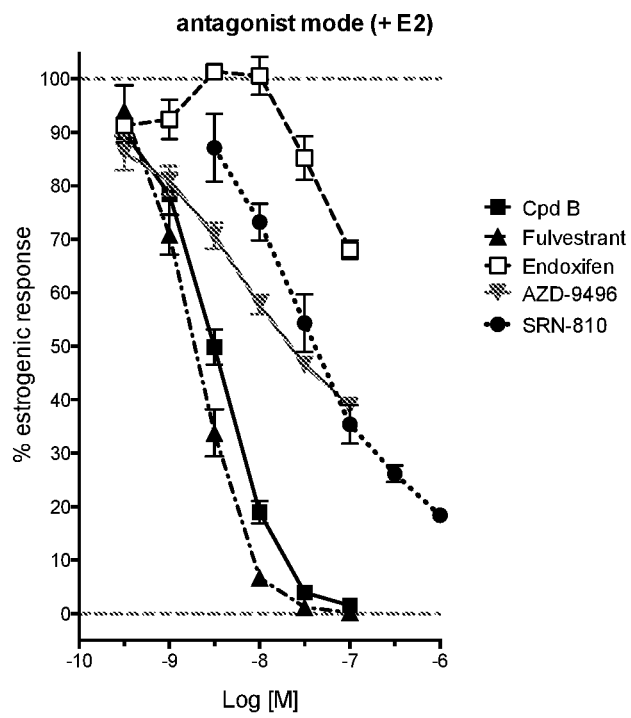
FIG. 6B is a plot of the % estrogenic response in for the compounds depicted within as antagonists in the presence of estrogen, as compared to the concentration of the depicted compound, measured logarithmically.

Further, Compounds B and C show great potential usefulness in treating human estrogen receptor driven pathologies such as breast cancer, as they are comparable in activity and function to fulvestrant, which has been shown to be superior to other hormonal therapies for treating first line metastatic human breast cancer. See PCT Application Publication No. WO2016/097072, page 19, lines 6-9 (noting fulvestrant is used to treat breast cancer in women which have progressed despite therapy with tamoxifen). Fulvestrant is a selective estrogen receptor degrader (SERD) and a pure antiestrogen with no intrinsic estrogen-like properties. Compounds B and C, similarly, are SERDs (FIGS. 1A-1B) and pure antagonists (FIGS. 6A-6B). Compounds B and C, further, have potency similar to fulvestrant in blocking estrogen driven gene expression and proliferation of human breast cancer cells (FIGS. 3 and 4). Compounds B and C are outstandingly potent in shrinking human breast cancer xenografts at the low dose of 10 mg/kg (FIGS. 5A and 5B). Thus compounds B and C demonstrate usefulness as antiestrogens for treating or preventing the recurrence or occurrence of breast cancer.

Figure 6C:
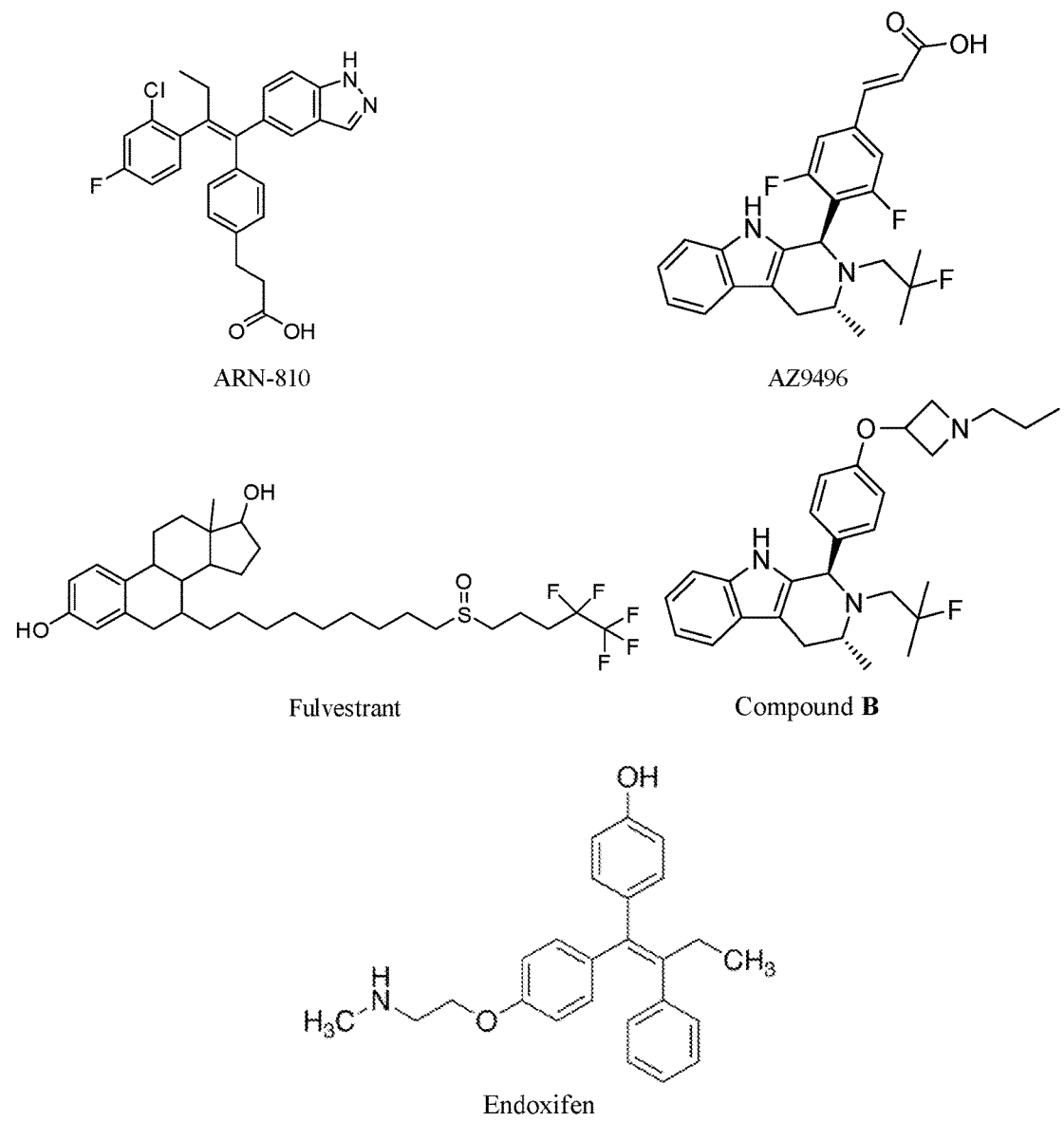
FIG. 6C provides depictions of the compounds examined in FIGS. 6A-6B.

As documented herein, provided compounds show complete antiestrogen activity in relevant assays, underscoring their usefulness in treating breast cancer, and particularly metastatic breast cancer. FIG. 6A-6B provides one illustration of this distinction, comparing an example compound of the present invention, Compound B, to fluvestrant, endoxifen, AZD9496, and ARN-810 (all compounds pictured in FIG. 6C).

Compounds can be provided if desired as a pharmaceutically acceptable salt, solvate, hydrate, prodrug, stereoisomer, tautomer, rotamer, N-oxide and/or substituted derivative optionally in a pharmaceutically acceptable composition to treat a disorder that is modulated or affected by an estrogen receptor, including those treatable with an anti-estrogenic.

The present invention particularly provides two specific compounds, Compound B ((1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole) and Compound C ((1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole), whose structures are surprisingly different from prior compounds described in the art as being useful estrogen receptor antagonists, and in fact contain specific structural features that teachings in the art affirmatively indicated were undesirable.

Specifically, Compounds B and C lack the difluorophenyl bridge that is present in the most active compounds presented by both AstraZeneca and Genentech. Further, as noted above, Compounds B and C incorporate the specific unsubstituted phenyl bridge that AstraZeneca indicated was undesirable due to poor activity as compared to compounds that comprise a difluorophenyl bridge.

It was found, however, that Compounds B and C show comparable activity to fulvestrant, an intramuscularly injected antiestrogen shown to be superior to other hormonal therapies for treating first-line metastatic human breast cancer. Compounds B and C have potency similar to fulvestrant in blocking estrogen driven gene expression and proliferation of human breast cancer cells unlike AZD9496. See FIGS. 2 and 4.

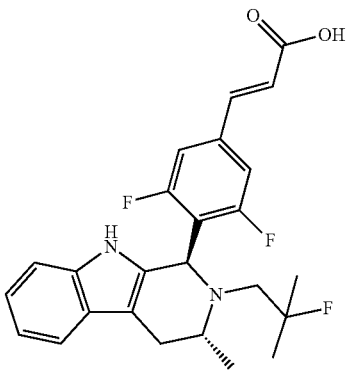 [SMILES: C[C@@H]1Cc2c([nH]c3ccccc23)[C@@H](c2c(F)cc(/C=C/C(=O)O)cc2F)N1CC(C)(C)F]

AZD9496

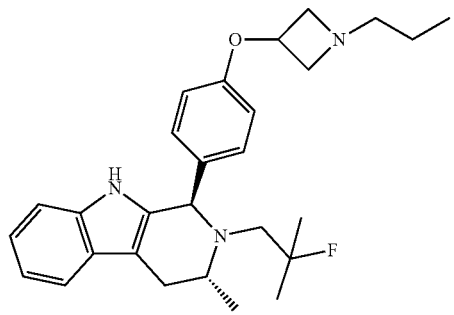

Compound B

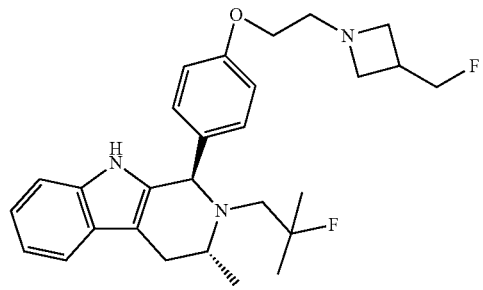

Compound C

The present disclosure exemplifies a variety of additional interesting and desirable activities for Compound B. For example, Compound B inhibited E2-induced transcription in breast cells with an $IC_{50}$=4.35 nM. Compound B also demonstrated inhibition of E2-stimulated proliferation in breast cells with an $IC_{50}$=4.53 nM. When ECC-1 cells were incubated with Compound B, the cells had only 2.18% of the AP activity that the cells would have if AP activity were normalized to the affect that 500 pM 17β-estradiol has on ECC-1 cells. When ECC-1 cells were co-treated with Compound B and 500 pM 17β-estradiol, the ECC-1 cells exhibited only 1.96% of the activity that 17β-estradiol would produce.

As noted above, Compounds B and C are within the scope of Formula I:

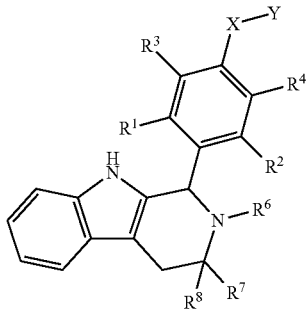

I wherein:
X is —CH$_2$— or —O—;
Y is

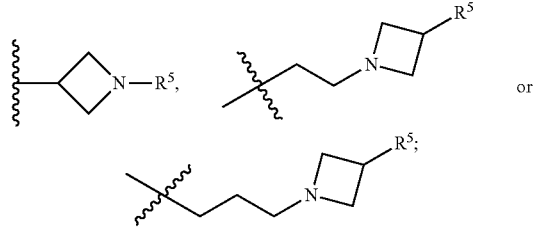

R$^1$, R and R$^4$ are each independently selected from hydrogen or halo;
R$^5$ is hydrogen, C$_1$-C$_6$alkyl, C$_1$-C$_6$haloalkyl, C$_2$-C$_6$alkenyl, C$_1$-C$_4$(C$_3$-C$_6$cycloalkyl) or C$_1$-C$_6$heteroalkyl;
R$^6$ is hydrogen, C$_1$-C$_6$alkyl, C$_1$-C$_6$haloalkyl or C$_1$-C$_4$(C$_3$-C$_6$cycloalkyl);
R$^7$ and R$^8$ are each independently selected from hydrogen or C$_1$-C$_6$alkyl;
or a pharmaceutically acceptable salt or a composition thereof.

The present disclosure defines various useful subgenera within Formula I. For example, in some embodiments, R$^1$, R$^2$, R$^3$, and R$^4$ are each independently selected from hydrogen or halo. In some embodiments, R$^1$, R$^2$, R$^3$, and R$^4$ are each independently selected from hydrogen or fluoro. In some embodiments, R$^1$, R$^2$, R$^3$, and R$^4$ are each hydrogen. As noted above, for Compounds B and C, R$^1$, R$^2$, R$^3$, and R$^4$ are each hydrogen.

In some embodiments, R$^1$ is hydrogen. In some embodiments, R$^2$ is hydrogen. In some embodiments, R$^3$ is hydrogen. In some embodiments, R$^4$ is hydrogen.

In some embodiments, R$^1$ is halo. In some embodiments, R$^2$ is halo. In some embodiments, R$^3$ is halo. In some embodiments, R$^4$ is halo. In some embodiments, R$^1$ is fluoro. In some embodiments, R$^2$ is fluoro. In some embodiments, R$^3$ is fluoro. In some embodiments, R$^4$ is fluoro.

In some embodiments of Formula I, R$^6$ is C$_1$-C$_6$haloalkyl. In some embodiments of Formula I, R$^6$ is C$_1$-C$_4$haloalkyl. In some embodiments of Formula I, R$^6$ is

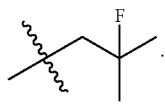 [SMILES: *CC(C)(C)F]

In some embodiments of Formula I, R$^7$ is C$_1$-C$_6$alkyl. In some embodiments of Formula I, R$^7$ is methyl.

In some embodiments, a compound is disclosed having Formula I(a):

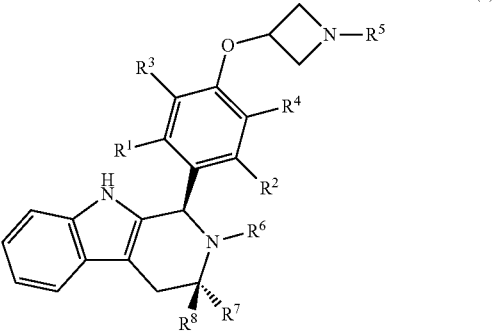

I(a)

wherein:
R$^1$, R$^2$, R$^3$, R$^4$, R$^5$, R$^6$, R$^7$ and R$^8$ are as defined above;
or a pharmaceutically acceptable salt thereof.

In some embodiments of Formula I(a), R$^1$, R$^2$, R$^3$, and R$^4$ are each independently selected from hydrogen or halo. In some embodiments, R$^1$, R$^2$, R$^3$, and R$^4$ are each independently selected from hydrogen or fluoro. In some embodiments, R$^1$, R$^2$, R$^3$, and R$^4$ are each independently selected from hydrogen.

In other embodiments, R$^1$ is hydrogen. In other embodiments, R$^2$ is hydrogen. In other embodiments, R$^3$ is hydrogen. In other embodiments, R$^4$ is hydrogen.

In other embodiments, R$^1$ is halo. In other embodiments, R$^2$ is halo. In other embodiments, R$^3$ is halo. In other embodiments, R$^4$ is halo. In other embodiments, R$^1$ is fluoro. In other embodiments, R$^2$ is fluoro. In other embodiments, R$^3$ is fluoro. In other embodiments, R$^4$ is fluoro. In some embodiments, only one of R$^1$, R$^2$, R$^3$, and R$^4$ is halo (e.g., fluoro).

In some embodiments of Formula I(a), R$^6$ is C$_1$-C$_6$haloalkyl. In some embodiments of Formula I(a), R$^6$ is C$_1$-C$_4$haloalkyl. In some embodiments of Formula I(a), R$^6$ is

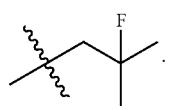 [SMILES: *CC(C)(C)F]

In some embodiments of Formula I(a), R$^7$ is C$_1$-C$_6$alkyl. In some embodiments of Formula I(a), R$^7$ is methyl.

In certain embodiments, a compound is disclosed having Formula I(b):

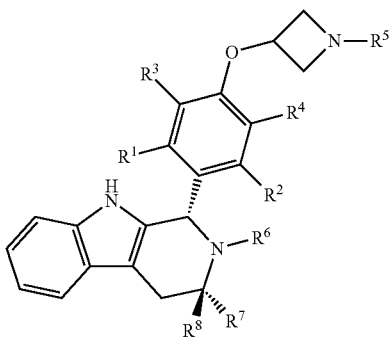

I(b)

wherein:
R$^1$, R$^2$, R$^3$, R$^4$, R$^5$, R$^6$, R$^7$ and R$^8$ are as defined above; or a pharmaceutically acceptable salt thereof.

In some embodiments of Formula I(b), R$^1$, R$^2$, R$^3$, and R$^4$ are each independently selected from hydrogen or halo. In some embodiments, R$^1$, R$^2$, R$^3$, and R$^4$ are each independently selected from hydrogen or fluoro. In some embodiments, R$^1$, R$^2$, R$^3$, and R$^4$ are each independently selected from hydrogen.

In some embodiments, R$^1$ is hydrogen. In some embodiments, R$^2$ is hydrogen. In some embodiments, R$^3$ is hydrogen. In some embodiments, R$^4$ is hydrogen.

In some embodiments, R$^1$ is halo. In some embodiments, R$^2$ is halo. In some embodiments, R$^3$ is halo. In some embodiments, R$^4$ is halo. In some embodiments, R$^1$ is fluoro. In some embodiments, R$^2$ is fluoro. In some embodiments, R$^3$ is fluoro. In some embodiments, R$^4$ is fluoro. In some embodiments, only one of R$^1$, R$^2$, R$^3$, and R$^4$ is halo (e.g., fluoro).

In some embodiments of Formula I(b), R$^6$ is C$_1$-C$_6$haloalkyl. In some embodiments of Formula I(b), R$^6$ is C$_1$-C$_4$haloalkyl. In some embodiments of Formula I(b), R$^6$ is

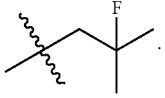 [SMILES: *CC(C)(C)F]

In some embodiments of Formula I(b), R$^7$ is C$_1$-C$_6$alkyl. In some embodiments of Formula I(b), R$^7$ is methyl.

In certain embodiments, a compound is disclosed having Formula I(c):

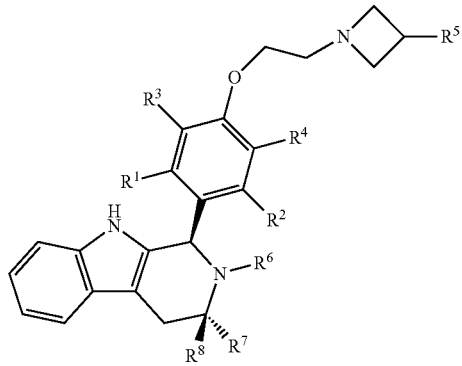

I(c)

wherein:
R$^1$, R$^2$, R$^3$, R$^4$, R$^5$, R$^6$, R$^7$ and R$^8$ are as defined above; or a pharmaceutically acceptable salt thereof.

In some embodiments of Formula I(c), R$^1$, R$^2$, R$^3$, and R$^4$ are each independently selected from hydrogen or halo. In some embodiments, R$^1$, R$^2$, R$^3$, and R$^4$ are each independently selected from hydrogen or fluoro. In some embodiments, R$^1$, R$^2$, R$^3$, and R$^4$ are each independently selected from hydrogen.

In some embodiments, R$^1$ is hydrogen. In some embodiments, R$^2$ is hydrogen. In some embodiments, R$^3$ is hydrogen. In some embodiments, R$^4$ is hydrogen.

In some embodiments, R$^1$ is halo. In some embodiments, R$^2$ is halo. In other embodiments, R$^3$ is halo. In some embodiments, R$^4$ is halo. In some embodiments, R$^1$ is fluoro. In some embodiments, R$^2$ is fluoro. In some embodiments, R$^3$ is fluoro. In some embodiments, R$^4$ is fluoro. In some embodiments, only one of R$^1$, R$^2$, R$^3$, and R$^4$ is halo (e.g., fluoro).

In some embodiments of Formula I(c), R$^6$ is C$_1$-C$_6$haloalkyl. In some embodiments of Formula I(c), R$^6$ is C$_1$-C$_4$haloalkyl. In some embodiments of Formula I(c), R$^6$ is

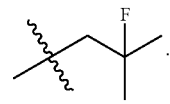 [SMILES: *CC(C)(C)F]

In some embodiments of Formula I(c), R$^7$ is C$_1$-C$_6$alkyl. In some embodiments of Formula I(c), R$^7$ is methyl.

In certain embodiments, a compound is disclosed having Formula I(d):

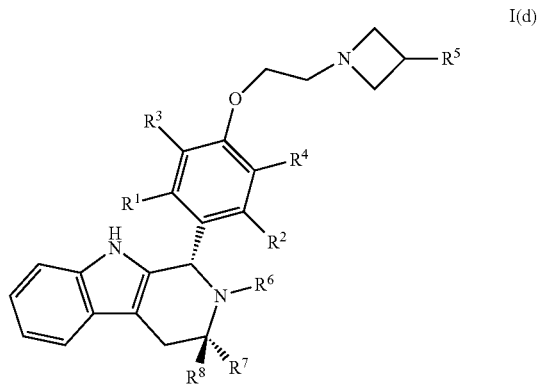

I(d)

wherein:
R$^1$, R$^2$, R$^3$, R$^4$, R$^5$, R$^6$, R$^7$ and R$^8$ are as defined above; or a pharmaceutically acceptable salt thereof.

In some embodiments of Formula I(d), R$^1$, R$^2$, R$^3$, and R$^4$ are each independently selected from hydrogen or halo. In some embodiments, R$^1$, R$^2$, R$^3$, and R$^4$ are each independently selected from hydrogen or fluoro. In some embodiments, R$^1$, R$^2$, R$^3$, and R$^4$ are each independently selected from hydrogen.

In some embodiments, R$^1$ is hydrogen. In some embodiments, R$^2$ is hydrogen. In some embodiments, R$^3$ is hydrogen. In some embodiments, R$^4$ is hydrogen.

In some embodiments, R$^1$ is halo. In some embodiments, R$^2$ is halo. In some embodiments, R$^3$ is halo. In some embodiments, $R^4$ is halo. In some embodiments, $R^1$ is fluoro. In some embodiments, $R^2$ is fluoro. In some embodiments, $R^3$ is fluoro. In some embodiments, $R^4$ is fluoro. In some embodiments, only one of $R^1$, $R^2$, $R^3$, and $R^4$ is halo (e.g., fluoro).

In some embodiments of Formula I(d), $R^6$ is $C_1$-$C_6$haloalkyl. In some embodiments of Formula I(d), $R^6$ is $C_1$-$C_4$haloalkyl. In some embodiments of Formula I(d), $R^6$ is

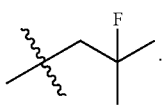

In some embodiments of Formula I(d), $R^7$ is $C_1$-$C_6$alkyl. In some embodiments of Formula I(d), $R^7$ is methyl.

In some embodiments, the present invention provides a compound of formulae I(e)-I(l):

TABLE 2

| Formula No. | Formula | $R^1$ | $R^2$ | $R^3$ | $R^4$ |
|---|---|---|---|---|---|
| I(e) | | — | Halo | Halo | Halo |
| I(f) | | Halo | Halo | — | Halo |
| I(g) | | — | — | Halo | Halo |
| I(h) | | — | Halo | — | Halo |
| I(i) | | — | Halo | Halo | — |
| I(j) | | — | — | — | Halo |
| I(k) | | — | Halo | — | — |

TABLE 2-continued

| Formula No. | Formula | $R^1$ | $R^2$ | $R^3$ | $R^4$ |
|---|---|---|---|---|---|
| I(l) | 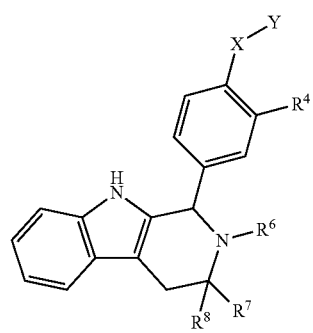 | — | — | — | — | wherein each of X, Y, $R^6$, $R^7$ and $R^8$ is as defined above and described herein.

In some embodiments of Formulae I(e), I(f), I(g), I(h), I(i), I(j), I(k) and I(l), halo is fluoro.

In some embodiments, the present invention provides a compound of formula I(j):

I(j)

wherein
$R^4$ is halo and $R^5$, $R^6$, $R^7$ and $R^8$ are as defined above;
or a pharmaceutically acceptable salt thereof.
In some embodiments of Formula I(j), $R^4$ is fluoro.
In some embodiments of Formula I(j), $R^6$ is $C_1$-$C_6$haloalkyl. In some embodiments of Formula I(j), $R^6$ is $C_1$-$C_4$haloalkyl. In some embodiments of Formula I(j), $R^6$ is

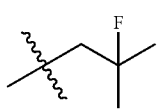

In some embodiments of Formula I(j), $R^7$ is $C_1$-$C_6$alkyl. In some embodiments of Formula I(j), $R^7$ is methyl.

In some embodiments, the present invention provides a compound of formula I(j)-1:

I(j)-1 wherein
$R^4$ is halo and $R^5$, $R^6$, $R^7$ and $R^8$ are as defined above;
or a pharmaceutically acceptable salt thereof.
In some embodiments of Formula I(j)-1, $R^4$ is fluoro.
In some embodiments of Formula I(j)-1, $R^6$ is $C_1$-$C_6$haloalkyl. In some embodiments of Formula I(j)-1, $R^6$ is $C_1$-$C_4$haloalkyl. In some embodiments of Formula I(j)-1, $R^6$ is

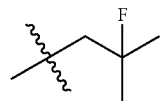

In some embodiments of Formula I(j)-1, $R^7$ is $C_1$-$C_6$alkyl.
In some embodiments of Formula I(j)-1, $R^7$ is methyl.

In some embodiments, the present invention provides a compound of formula I(j)-2:

I(j)-2 wherein
$R^4$ is halo and $R^5$, $R^6$, $R^7$ and $R^8$ are as defined above;
or a pharmaceutically acceptable salt thereof.
In some embodiments of Formula I(j)-2, $R^4$ is fluoro.
In some embodiments of Formula I(j)-2, $R^6$ is $C_1$-$C_6$haloalkyl. In some embodiments of Formula I(j)-2, $R^6$ is $C_1$-$C_4$haloalkyl. In some embodiments of Formula I(j)-2, $R^6$ is

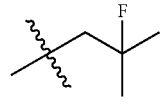

In some embodiments of Formula I(j)-2, $R^7$ is $C_1$-$C_6$alkyl.
In some embodiments of Formula I(j)-2, $R^7$ is methyl.

In some embodiments, the present invention provides a compound of formula I(j)-3:

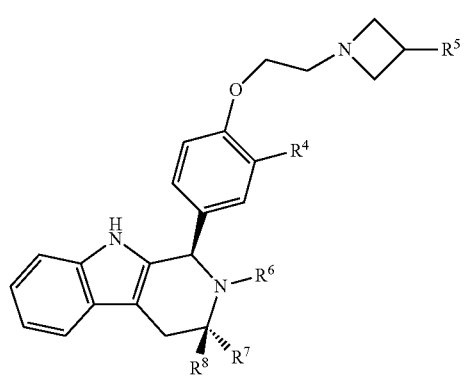

I(j)-3 wherein
$R^4$ is halo and $R^5$, $R^6$, $R^7$ and $R^8$ are as defined above;
or a pharmaceutically acceptable salt thereof.
In some embodiments of Formula I(j)-3, $R^4$ is fluoro.
In some embodiments of Formula I(j)-3, $R^6$ is $C_1$-$C_6$haloalkyl. In some embodiments of Formula I(j)-3, $R^6$ is $C_1$-$C_4$haloalkyl. In some embodiments of Formula I(j)-3, $R^6$ is

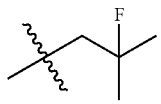

In some embodiments of Formula I(j)-3, $R^7$ is $C_1$-$C_6$alkyl.
In some embodiments of Formula I(j)-3, $R^7$ is methyl.

In some embodiments a compound is disclosed having formula I(j)-4:

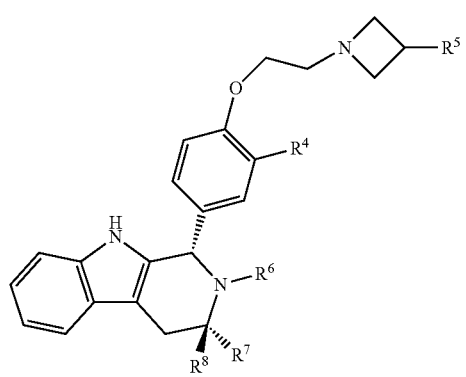

I(j)-4 wherein
$R^4$ is halo and $R^5$, $R^6$, $R^7$ and $R^8$ are as defined above;
or a pharmaceutically acceptable salt thereof.
In some embodiments of Formula I(j)-4, $R^4$ is fluoro.
In some embodiments of Formula I(j)-4, $R^6$ is $C_1$-$C_6$haloalkyl. In some embodiments of Formula I(j)-4, $R^6$ is $C_1$-$C_4$haloalkyl. In some embodiments of Formula I(j)-4, $R^6$ is

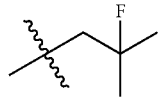

In some embodiments of Formula I(j)-4, $R^7$ is $C_1$-$C_6$alkyl.
In some embodiments of Formula I(j)-4, $R^7$ is methyl.

In some embodiments, a compound is disclosed having formula I(l):

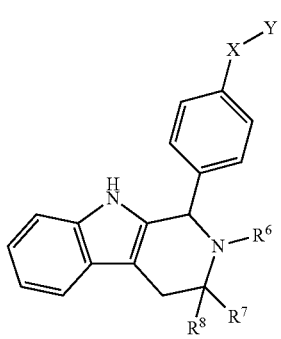

I(l)

wherein
$R^5$, $R^6$, R and $R^8$ are as defined above;
or a pharmaceutically acceptable salt thereof.
In some embodiments of Formula I(l), $R^6$ is $C_1$-$C_6$haloalkyl. In some embodiments of Formula I(l), $R^6$ is $C_1$-$C_4$haloalkyl. In some embodiments of Formula I(l), $R^6$ is

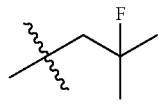

In some embodiments of Formula I(l), $R^7$ is $C_1$-$C_6$alkyl.
In some embodiments of Formula I(l), $R^7$ is methyl.

In some embodiments, a compound is disclosed having formula I(l)-1:

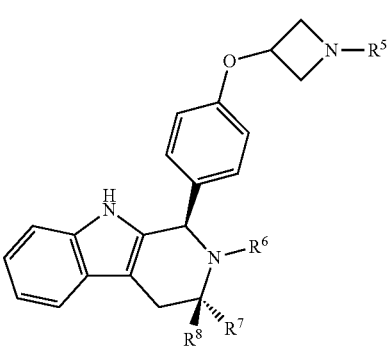

I(l)-1 wherein
$R^5$, $R^6$, $R^7$ and $R^8$ are as defined above;
or a pharmaceutically acceptable salt thereof.
In some embodiments of Formula I(l)-1, $R^6$ is $C_1$-$C_6$haloalkyl. In some embodiments of Formula I(l)-1, $R^6$ is $C_1$-$C_4$haloalkyl. In some embodiments of Formula I(l)-1, R is

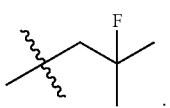

In some embodiments of Formula I(l)-1, $R^7$ is $C_1$-$C_6$alkyl. In some embodiments of Formula I(l)-1, $R^7$ is methyl.

In some embodiments, a compound is disclosed having formula I(l)-2:

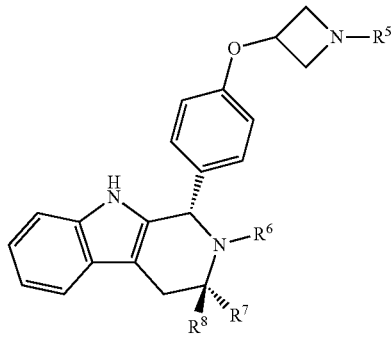

I(l)-2 wherein
$R^5$, $R^6$, $R^7$ and $R^8$ are as defined above;
or a pharmaceutically acceptable salt thereof.

In some embodiments of Formula I(l)-2, $R^6$ is $C_1$-$C_6$haloalkyl. In some embodiments of Formula I(l)-2, $R^6$ is $C_1$-$C_4$haloalkyl. In some embodiments of Formula I(l)-2, $R^6$ is

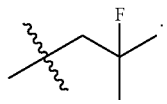 [SMILES: *CC(C)(C)F]

In some embodiments of Formula I(l)-2, $R^7$ is $C_1$-$C_6$alkyl. In some embodiments of Formula I(l)-2, $R^7$ is methyl.

In some embodiments, a compound is disclosed having formula I(l)-3:

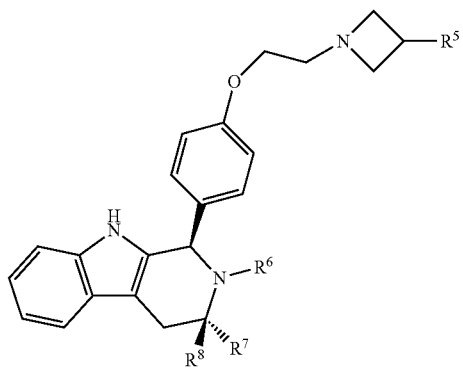

I(l)-3 wherein
$R^5$, $R^6$, $R^7$ and $R^8$ are as defined above;
or a pharmaceutically acceptable salt thereof.

In some embodiments of Formula I(l)-3, $R^6$ is $C_1$-$C_6$haloalkyl. In some embodiments of Formula I(l)-3, $R^6$ is $C_1$-$C_4$haloalkyl. In some embodiments of Formula I(l)-3, $R^6$ is

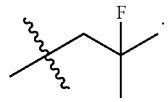 [SMILES: *CC(C)(C)F]

In some embodiments of Formula I(l)-3, $R^7$ is $C_1$-$C_6$alkyl. In some embodiments of Formula I(l)-3, $R^7$ is methyl.

In some embodiments, a compound is disclosed having formula I(l)-4:

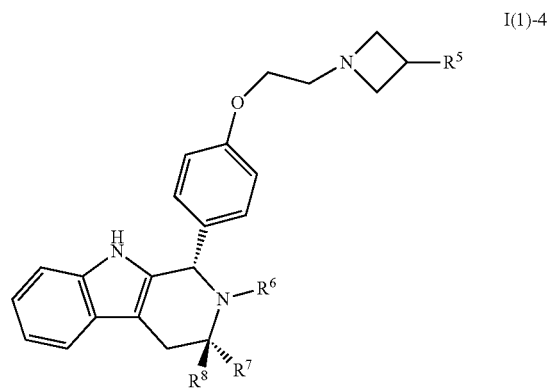

I(l)-4 wherein
$R^5$, $R^6$, $R^7$ and $R^8$ are as defined above;
or a pharmaceutically acceptable salt thereof.

In some embodiments of Formula I(l)-4, $R^6$ is $C_1$-$C_6$haloalkyl. In some embodiments of Formula I(l)-4, $R^6$ is $C_1$-$C_4$haloalkyl. In some embodiments of Formula I(l)-4, $R^6$ is

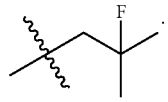 [SMILES: *CC(C)(C)F]

In some embodiments of Formula I(l)-4, $R^7$ is $C_1$-$C_6$alkyl. In some embodiments of Formula I(l)-4, $R^7$ is methyl.

In some embodiments, the present invention provides a compound of Formula I(m):

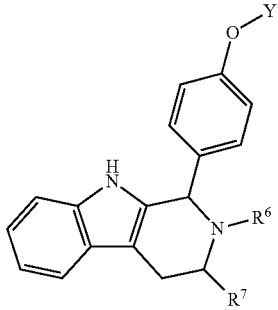

I(m)

wherein

R⁶, R⁷, and Y are as defined above.

In some embodiments of Formula I(m), R⁶ is $C_1$-$C_6$haloalkyl. In some embodiments of Formula I(m), R⁶ is $C_1$-$C_4$haloalkyl. In some embodiments of Formula I(m), R⁶ is

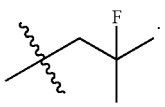 [SMILES: *CC(C)(C)F]

In some embodiments of Formula I(m), R⁷ is $C_1$-$C_6$alkyl. In some embodiments of Formula I(m), R⁷ is methyl.

In some embodiments, the present invention provides a compound of Formula I(n)

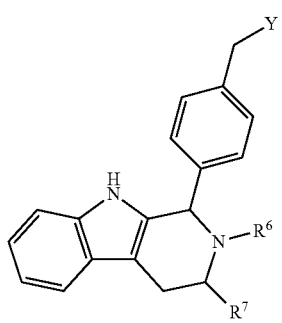

I(n)

wherein

R⁶, R⁷, and Y are as defined above.

In some embodiments of Formula I(n), R⁶ is $C_1$-$C_6$haloalkyl. In some embodiments of Formula I(n), R⁶ is $C_1$-$C_4$haloalkyl. In some embodiments of Formula I(n), R⁶ is

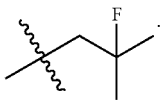 [SMILES: *CC(C)(C)F]

In some embodiments of Formula I(n), R⁷ is $C_1$-$C_6$alkyl. In some embodiments of Formula I(n), R⁷ is methyl.

In some embodiments of any of the Formulae described herein (e.g., Formulae I, I(a), I(b), I(c), I(d), I(e), I(f), I(g), I(h), I(i), I(j), I(j)-1, I(j)-2, I(j)-3, I(j)-4, I(k), I(l), I(l)-1, I(l)-2, I(l)-3, I(l)-4, I(m), and I(n)), R⁵ is $C_1$-$C_6$alkyl. In some embodiments of any of the Formulae described herein, R⁵ is $C_1$-$C_5$alkyl. In some embodiments of any of the Formulae described herein, R⁵ is $C_1$-$C_4$alkyl. In some embodiments of any of the Formulae described herein, R⁵ is $C_1$-$C_3$alkyl. In some embodiments of any of the Formulae described herein, R⁵ is $C_1$-$C_2$alkyl. In some embodiments of any of the Formulae described herein, R⁵ is chosen from methyl, ethyl, propyl, isopropyl, butyl, isobutyl, tert-butyl, sec-butyl, pentyl, isopentyl, neopentyl, or hexyl. In some embodiments of any of the Formulae described herein, R⁵ is methyl. In some embodiments of any of the Formulae described herein, R⁵ is ethyl. In some embodiments of any of the Formulae described herein, R⁵ is propyl.

In some embodiments of any of the Formulae desired herein, R⁵ is $C_1$-$C_6$haloalkyl. In some embodiments of any of the Formulae described herein, R⁵ is —CH₂F. In some embodiments of any of the Formulae described herein, R⁵ is —CHF₂. In some embodiments of any of the Formulae described herein, R⁵ is —CF₃.

In some embodiments of any of the Formulae described herein, R⁶ is selected from hydrogen, $C_1$-$C_6$alkyl, $C_1$-$C_6$haloalkyl or $C_1$-$C_4$($C_3$-$C_6$cycloalkyl). In some embodiments of any of the Formulae described herein, R⁶ is $C_1$-$C_6$haloalkyl. In some embodiments of any of the Formulae described herein, R⁶ is —CH₂CF(CH₃)₂. In some embodiments of any of the Formulae described herein, R⁶ is $C_1$-$C_5$alkyl or haloalkyl. In some embodiments of any of the Formulae described herein, R⁶ is $C_1$-$C_4$alkyl or haloalkyl. In some embodiments of any of the Formulae described herein, R⁶ is $C_1$-$C_3$alkyl or haloalkyl. In some embodiments of any of the Formulae described herein, R⁶ is $C_1$-$C_2$alkyl. In some embodiments of any of the Formulae described herein, R⁶ is selected from methyl, ethyl, propyl, isopropyl, butyl, isobutyl, tert-butyl, sec-butyl, pentyl, isopentyl, neopentyl, or hexyl. In some embodiments of any of the Formulae described herein, R⁶ is methyl or halomethyl. In some embodiments of any of the Formulae described herein, R⁶ is ethyl or haloethyl.

In some embodiments of any of the Formulae described herein, R⁷ and R⁸ are each independently selected from hydrogen or $C_1$-$C_6$alkyl (which can be in any subembodiment as described above for R⁵ or R⁶). In some embodiments of any of the Formulae described herein, R⁷ is methyl and R⁸ is hydrogen.

Moreover, the present disclosure reports Compound B ((1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole):

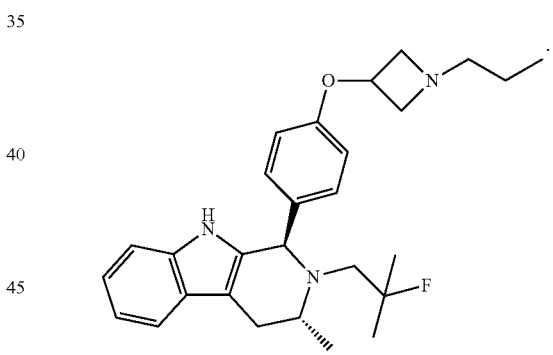

Further, the present discloses reports Compound C ((1R, 3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole):

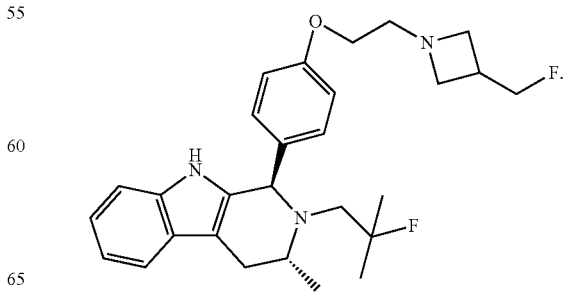

Terminology

The foregoing general description and the following detailed description are exemplary and explanatory only and are not restrictive of the invention. Other features and benefits of any one or more of the embodiments will be apparent from the following detailed description, and from the claims.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). Unless otherwise stated, the invention encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group that in one embodiment has from 1 to 6 carbon atoms ("$C_{1-6}$alkyl"). In some embodiments, an alkyl group has 1 to 5 carbon atoms ("$C_{1-5}$alkyl"). In some embodiments, an alkyl group has 1 to 4 carbon atoms ("$C_{1-4}$alkyl"). In some embodiments, an alkyl group has 1 to 3 carbon atoms ("$C_{1-3}$alkyl"). In some embodiments, an alkyl group has 1 to 2 carbon atoms ("$C_{1-2}$alkyl"). In some embodiments, an alkyl group has 1 carbon atom ("$C_1$alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-6}$ alkyl (e.g., —$CH_3$). In certain embodiments, the alkyl group is substituted $C_{1-6}$ alkyl.

"Alkenyl" refers to a radical of a straight-chain or branched hydrocarbon group that in one embodiment has from 2 to 6 carbon atoms, one or more carbon-carbon double bonds, and no triple bonds ("$C_{2-6}$alkenyl"). In some embodiments, an alkenyl group has 2 to 5 carbon atoms ("$C_{2-5}$alkenyl"). In some embodiments, an alkenyl group has 2 to 4 carbon atoms ("$C_{2-4}$alkenyl"). In some embodiments, an alkenyl group has 2 to 3 carbon atoms ("$C_{2-3}$alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-6}$ alkenyl. In certain embodiments, the alkenyl group is substituted $C_{2-6}$ alkenyl.

"Carbocyclyl", "cycloalkyl" or "carbocyclic" refers to a radical of a non-aromatic cyclic hydrocarbon group having from 3 to 8 ring carbon atoms ("$C_{3-8}$carbocyclyl") and zero heteroatoms in the non-aromatic ring system. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. As the foregoing examples illustrate, in certain embodiments, the carbocyclyl group is either monocyclic ("monocyclic carbocyclyl") or contains a fused, bridged or spiro ring system such as a bicyclic system ("bicyclic carbocyclyl") and can be saturated or can be partially unsaturated. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-8}$ carbocyclyl. In certain embodiments, the carbocyclyl group is a substituted $C_{3-8}$ carbocyclyl.

"Halo" or "halogen" refers to fluorine (fluoro, —F), chlorine (chloro, —Cl), bromine (bromo, —Br) or iodine (iodo, —I).

"Haloalkyl" is a substituted $C_1$-$C_6$alkyl group as defined herein wherein one or more of the hydrogen atoms of the $C_1$-$C_6$alkyl group are independently replaced by a halogen, e.g., fluoro, bromo, chloro, or iodo. In some embodiments, the alkyl moiety has 1 to 6 carbon atoms ("$C_1$-$C_6$alkyl"). In some embodiments, the alkyl moiety has 1 to 4 carbon atoms ("$C_1$-$C_4$haloalkyl"). In some embodiments, the alkyl moiety has 1 to 3 carbon atoms ("$C_1$-$C_3$haloalkyl"). In some embodiments, the alkyl moiety has 1 to 2 carbon atoms ("$C_1$-$C_2$haloalkyl"). In some embodiments, the alkyl moiety has 1 carbon atom ("$C_1$haloalkyl"). In some embodiments, all of the hydrogen atoms are replaced with fluoro. Examples of haloalkyl groups include $CH_2F$, $CHF_2$, —$CF_3$, —$CH_2CH_2F$, $CH_2CHF_2$, —$CH_2CF_3$ and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl and the like having from 1 to 3, and typically one heteroatom.

"Heterocyclyl," "heterocycle" or "heterocyclic" refers to a radical of a 3- to 6-membered nonaromatic ring system having ring carbon atoms and 1 to 2 ring heteroatoms, wherein each heteroatom is independently selected from nitrogen, oxygen, and sulfur ("3-6 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is unsubstituted 3-6 membered heterocyclyl. In certain embodiments, the heterocyclyl group is substituted 3-6 membered heterocyclyl. In one embodiment, the heterocyclyl group is substituted 4-membered heterocyclyl. In one embodiment, the heterocyclyl group is substituted azetidine.

Alkyl, alkenyl, carbocyclyl, heteroalkyl and heterocyclyl groups, as defined herein, are optionally substituted (e.g., "substituted" or "unsubstituted" alkyl, "substituted" or "unsubstituted" alkenyl, "substituted" or "unsubstituted" carbocyclyl, "substituted" or "unsubstituted" heteroalkyl). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. Exemplary carbon and nitrogen atom substituents include, but are not limited to, halogen, hydroxyl, amino, cyano, —COOH, —$CONH_2$, $C_1$-$C_6$alkyl, $C_1$-$C_6$alkenyl, $C_1$-$C_6$alkoxy, $C_2$-$C_6$acyl, $C_1$-$C_6$alkylester, (mono- and di-$C_1$-$C_6$alkylamino)$C_0$-$C_2$alkyl-, $C_1$-$C_4$haloalkyl, and $C_1$-$C_4$haloalkoxy.

"Agent" or "anti-cancer agent," as used herein, refers to chemotherapeutic agents, targeted therapies, and hormonal therapies. Suitable examples of anti-cancer agents are, for example, the chemotherapy agent gemcitibine, the targeted therapies palbociclib and everolimus, and the hormonal therapies for breast cancer such as tamoxifen, fulvestrant, steroidal aromatase inhibitors, and non-steroidal aromatase inhibitors.

Purity and Stereochemistry of Compounds

As used herein the term "enantiomerically pure" or "pure enantiomer" denotes that the compound comprises at least 95% by weight of a single enantiomer. In alternative embodiments, when specified, the term may refer to at least 96% by weight, at least 97% by weight, at least 98% by weight, at least 98.5% by weight, at least 99% by weight, at least 99.2% by weight, at least 99.5% by weight, at least 99.6% by weight, at least 99.7% by weight, at least 99.8% by weight or at least 99.9% by weight, of the enantiomer. The weights are based upon total weight of all enantiomers or stereoisomers of the compound.

As used herein and unless otherwise indicated, the term "enantiomerically pure (1R,3R) compound" refers to at least 95% by weight (1R,3R)-compound and at most about 5% by weight of the (1S,3R), (1R,3S), and (1S,3S) compounds. In alternative embodiments, when specified, the term can refer to at least about 99% by weight (1R,3R)-compound and at most about 1% by weight of the (1S,3R), (1R,3S), and (1S,3S) compounds or at least about 99.9% by weight (1R,3R)-compound or at most about 0.1% by weight of the (1S,3R), (1R,3S), and (1S,3S) compounds. In certain embodiments, the weights are based upon total weight of compound.

As used herein the term "diastereomerically pure" or "pure diastereomer" denotes that the compound in the specific diastereomer, comprises approximately 95% or more by weight. In alternative embodiments, the term may refer to more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight of the diastereomer. The weights are based upon total weight of all stereoisomers of the compound.

In one embodiment, the compounds are provided generally in any state of purity. In another embodiment, the compounds of the Formulas are substantially pure. By use of the term "substantially pure", it is meant that the compounds of Formula I are at least about 80% by weight pure. In another embodiment, the compounds of Formula I are at least about 85% by weight pure, while in another embodiment, it is at least about 90% by weight pure. In still another embodiment, the term "substantially pure" means that the compounds of Formula I are at least about 95% pure by weight. In another embodiment, it is at least about 97% pure by weight, and in another embodiment, it is at least about 98% and in still another embodiment, it is at least about 99% pure by weight. Unless otherwise indicated, the term substantially pure means at least about 90% by weight. The compounds of Formula I include stereoisomers thereof, including, without limitation, enantiomers, diastereomers and racemic mixtures thereof, unless the chemical structure depicts a certain stereo configuration. In that case, the corresponding enantiomer, diastereomer or racemic mixture may be used in an alternative embodiment.

In particular, it is noted that the carbon atoms at the 1 and 3-positions of the tetrahydro-1H-pyrido[3,4-b]indole core of the compounds of Formula I which are bonded to a phenyl group; and $R^7$ and $R^8$ groups respectively, are chiral carbons; thus, the compounds may exist in either the R or S configuration at these positions. The present disclosure includes all of the possible stereoisomers at the 1 and 3-positions of the tetrahydro-1H-pyrido[3,4-b]indole, or a mixture thereof in any ratio, including a racemic mixture. In one embodiment, the carbon atoms at the 1 and 3-positions of the tetrahydro-1H-pyrido[3,4-b]indole bonded to a phenyl group; and $R^7$ and $R^8$ groups respectively have the (1R,3R) configuration. In another embodiment, the carbon atoms at the 1 and 3-positions of the tetrahydro-1H-pyrido[3,4-b]indole bonded to a phenyl group; and $R^7$ and $R^8$ groups respectively have the (1S,3S) configuration. In another embodiment, the carbon atoms at the 1 and 3-positions of the tetrahydro-1H-pyrido[3,4-b]indole bonded to a phenyl group; and $R^7$ and $R^8$ groups respectively have the (1R,3S) configuration. In another embodiment, the carbon atoms at the 1 and 3-positions of the tetrahydro-1H-pyrido[3,4-b]indole bonded to a phenyl group; and $R^7$ and $R^8$ groups respectively have the (1S,3R) configuration.

Compounds of the present disclosure include diastereomerically or enantiomerically pure compounds of Formula I. These diastereomerically or enantiomerically pure compounds of Formula I provided herein may be prepared according to techniques known to those of skill in the art. For instance, they may be prepared by chiral or asymmetric synthesis from a suitable optically pure precursor or obtained from a racemate or mixture of enantiomers or diastereomers by any conventional technique, for example, by chromatographic resolution using a chiral column, TLC or by the preparation of diastereoisomers, separation thereof and regeneration of the desired enantiomer or diastereomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, Tetrahedron, 2725 (1977); E. L. Eliel Stereochemistry of Carbon Compounds (McGraw-Hill, N Y, 1962); and S. H. Wilen Tables of Resolving Agents and Optical Resolutions 268 (E. L. Eliel ed., Univ. of Notre Dame Press, Notre Dame, Ind., 1972, Stereochemistry of Organic Compounds, Ernest L. Eliel, Samuel H. Wilen and Lewis N. Manda (1994 John Wiley & Sons, Inc.), and Stereoselective Synthesis A Practical Approach, Mihály Nógradi (1995 VCH Publishers, Inc., NY, N.Y.).

In certain embodiments, a diastereomerically pure compound of Formula I may be obtained by reaction of the racemate or mix of diastereomers with a suitable optically active acid or base. Suitable acids or bases include those described in Bighley et al., 1995, Salt Forms of Drugs and Adsorption, in Encyclopedia of Pharmaceutical Technology, vol. 13, Swarbrick & Boylan, eds., Marcel Dekker, New York; ten Hoeve & H. Wynberg, 1985, Journal of Organic Chemistry 50:4508-4514; Dale & Mosher, 1973, J. Am. Chem. Soc. 95:512; and CRC Handbook of Optical Resolution via Diastereomeric Salt Formation, the contents of which are hereby incorporated by reference in their entireties.

Enantiomerically or diastereomerically pure compounds can also be recovered either from the crystallized diastereomer or from the mother liquor, depending on the solubility properties of the particular acid resolving agent employed and the particular amine enantiomer or diastereomer used. The identity and optical purity of the particular compound so recovered can be determined by polarimetry or other analytical methods known in the art. The diastereoisomers can then be separated, for example, by chromatography or fractional crystallization, and the desired enantiomer or diastereomer regenerated by treatment with an appropriate base or acid. The other enantiomer or diastereomer may be obtained from the racemate or mix of diastereomers in a similar manner or worked up from the liquors of the first separation.

In certain embodiments, an enantiomerically or diastereomerically pure compound can be separated from racemic compound or a mixture of diastereomers by chiral chromatography. Various chiral columns and eluents for use in the separation of the enantiomers or diastereomers are available and suitable conditions for the separation can be empirically determined by methods known to one of skill in the art. Exemplary chiral columns available for use in the separation of the enantiomers provided herein include, but are not limited to, CHIRALPAK® IA-3, CHIRALPACK® IC, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Isotopic Substitution

The present invention includes the compounds of Formula I and the use of compounds with desired isotopic substitutions of atoms, at an amount above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom can be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby an H-isotope, i.e., hydrogen/protium ($^1H$), is replaced by an H-isotope, i.e., deuterium ($^2H$). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. In certain embodiments, deuterium in place of a hydrogen at one or more of the positions of Formula I are provided.

Compounds of Formula I

In one embodiment, the compound is selected from the group consisting of:

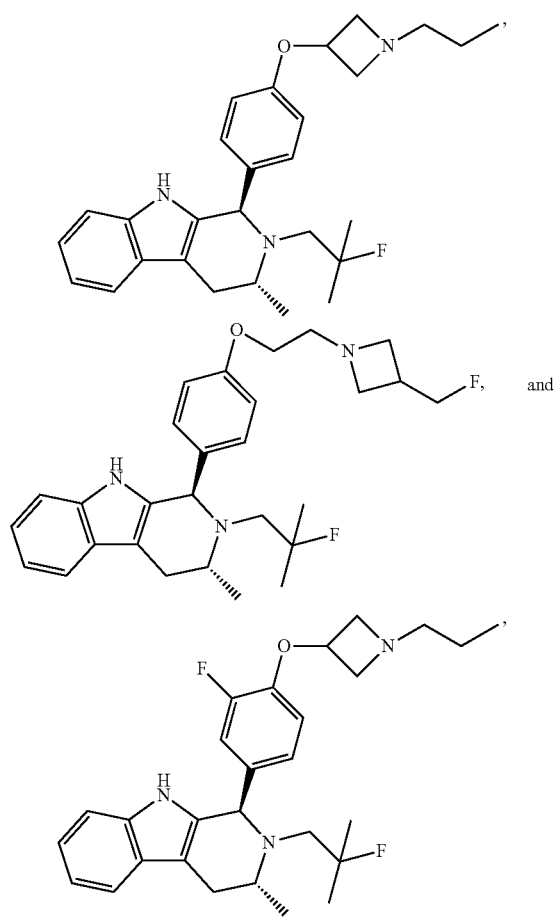

or a pharmaceutically acceptable salt thereof.

In one embodiment, a compound of Formula I is provided as a prodrug, for example, a methyl dihydrogen phosphate, see, US 2012/0238755.

In some embodiments, the present invention provides a compound:

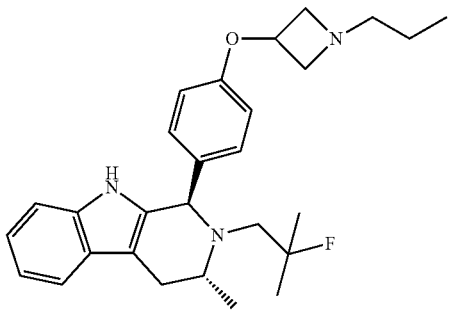 [SMILES: CCCN1CC(Oc2ccc([C@@H]3c4[nH]c5ccccc5c4C[C@@H](C)N3CC(C)(C)F)cc2)C1]

or a pharmaceutically acceptable salt thereof.

In some embodiments the present invention provides a compound:

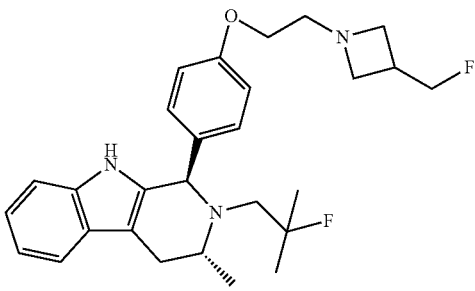 [SMILES: C[C@@H]1Cc2c([nH]c3ccccc23)[C@@H](c2ccc(OCCN3CC(CF)C3)cc2)N1CC(C)(C)F]

or a pharmaceutically acceptable salt thereof.

In some embodiments, the present invention provides a compound:

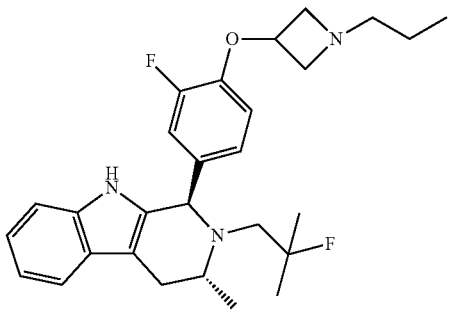 [SMILES: CCCN1CC(Oc2ccc([C@@H]3c4[nH]c5ccccc5c4C[C@@H](C)N3CC(C)(C)F)cc2F)C1]

or a pharmaceutically acceptable salt thereof.

Compounds of the present invention provide surprising advantages over the compounds reported by AstraZeneca (PCT Application Publication No. WO 2014/191726) and Genentech (PCT Application Publication No. WO 2016/097072) in that they lack the difluorophenyl bridge found in almost all compounds reported by AstraZeneca and Genetech, yet provide improved biological activity as inhibitors of the estrogen receptor over the compounds reported by either AstraZeneca or Genentech, as discussed above and illustrated further in the Examples below.

Pharmaceutical Compositions

A "dosage form" means a unit of administration of an active agent. Non-limiting examples of dosage forms include tablets, capsules, injections, suspensions, liquids, intravenous fluids, emulsions, creams, ointments, suppositories, inhalable forms, transdermal forms, and the like.

"Pharmaceutical compositions" are compositions comprising at least one active agent, such as a compound or salt of one of the active compounds disclosed herein, and at least one other substance, such as a carrier. Pharmaceutical compositions optionally contain more than one active agents. "Pharmaceutical combinations" or "combination therapy" refers to the administration of at least two active agents, and in one embodiment, three or four or more active agents which may be combined in a single dosage form or provided together in separate dosage forms optionally with instructions that the active agents are to be used together to treat a disorder as described herein.

The compounds of the invention can be administered in an effective amount in a pharmaceutical composition and dosage form suitable for oral delivery to the patient, typically a human for any of the conditions described herein. Alternatively, the compounds can be delivered in a carrier suitable for topical, transdermal (including by patch), intravenous, intra-arterial, vaginal, rectal, buccal, sublingual, parenteral, intraaortal, subcutaneous or other desired delivery route, including any method of controlled delivery, for example, using degradable polymers, or with nano or microparticles, liposomes, layered tablets or other structural frameworks which slow delivery.

In one aspect, the active compound of the invention can be used to prevent a disorder modulated through the estrogen receptor, which comprises administering to a patient in need of such prevention, a prophylactically effective amount of a compound or pharmaceutical composition.

"Pharmaceutically acceptable salt" refers to a salt of a compound of the invention that is pharmaceutically acceptable and that possesses the desired pharmacological activity of the parent compound. In particular, such salts have low toxicity and may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like. A counterion or anionic counterion can be used in a quaternary amine to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, and the like), and carboxylate ions (e.g., acetate, ethanoate, propanoate, benzoate, glycerate, lactate, tartrate, glycolate, and the like).

"Pharmaceutically acceptable carrier" refers to a diluent, adjuvant, excipient or other carrier in which a compound of the invention is administered.

A "pharmaceutically acceptable excipient" means an excipient that is useful in preparing a pharmaceutical composition/combination that is generally safe, is sufficiently nontoxic, and neither biologically nor otherwise undesirable. A "pharmaceutically acceptable excipient" as used in the present application includes both one and more than one such excipient.

A "prodrug" as used herein, means a compound which when administered to a host in vivo is converted into a parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups.

"Solvate" refers to forms of the compound that are associated with a solvent or water (also referred to as "hydrate"), usually by a solvolysis reaction. This physical association can include hydrogen bonding. Conventional solvents include water, ethanol, acetic acid and the like. The compounds of the invention may be prepared e.g. in crystalline or liquid form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "host" or "subject" to which administration is contemplated includes any host that responds to anti-estrogenic therapy or therapy that modulates estrogen receptor activity and is typically a human (i.e., a female or male of any age group, e.g., a pediatric subject (e.g., infant, child, adolescent)) or adult subject (e.g., young adult, middle-aged adult or senior adult)). In an alternative embodiment, the host is a non-human animal, e.g., a mammal such as primates (e.g., cynomolgus monkeys, rhesus monkeys), cattle, pigs, horses, sheep, goats, rodents, cats, and/or dogs.

In some embodiments, the pharmaceutical composition is a tablet, a pill, a capsule, a liquid, a suspension, a gel, a dispersion, a suspension, a solution, an emulsion, an ointment, or a lotion.

Effective amounts of a compound of Formula I or its pharmaceutically acceptable salt etc., in the composition will typically be determined by a physician, in the light of the relevant circumstances, including the condition to be treated, the chosen route of administration, the compound or salt administered, the age, weight, and response of the individual patient, the severity of the patient's symptoms, and the like.

For oral dosing, any dose is appropriate that achieves the desired goals. In one example, suitable daily dosages are between about 0.1-4,000 mg, more typically between 5 mg and 1 gram, more typically between 10 mg and 500 mg, and administered orally once-daily, twice-daily or three times-daily, continuous (every day) or intermittently (e.g., 3-5 days a week). For example, when used to treat any disorder described herein, the dose of the compounds of Formula I or their pharmaceutically acceptable salt, solvate, hydrate, prodrug, stereoisomer, rotamer or tautomer is provided in a dosage of at least about 0.1, 0.5, 1, 5, 25, 50, 75, 100, 150, 200, 300, 400, 500, 600, 700, 800, 1000, 1200, 1500 or 2000 mg per day. In one embodiment, the dose of the compounds of Formula I or their pharmaceutically acceptable salt, solvate, hydrate, prodrug, stereoisomer, rotamer or tautomer is provided in a dosage of at least about 10, 50, 100, 200, 250, 1,000 or up to about 2,000 mg per day. Alternatively, nonlimiting dosages can range from about 0.01 to about 20 mg/kg of the compound of Formula I or its pharmaceutically acceptable salt, solvate, hydrate, prodrug, stereoisomer or tautomer provided herein, with typical doses providing from about 0.1 to about 10 mg/kg and especially about 1 to about 5 mg/kg.

Described herein below are various nonlimiting examples of pharmaceutically acceptable compositions that include a compound of Formula I or its pharmaceutically acceptable salt, etc., in a pharmaceutically acceptable carrier. The formulation includes the active ingredient, either as a weight ratio or as a weight amount. It is to be understood, unless indicated to the contrary, that the weight amount and weight ratios are based upon the molecular weight of the compound of Formula I, even if the formulation contains the salt form thereof.

Compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material of the compound of Formula I or its pharmaceutically acceptable salt calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound of Formula I or its pharmaceutically acceptable salt may be present as a minor component (as a nonlimiting example, from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions comprised of a compound of Formula I or its pharmaceutically acceptable salts are contemplated within the present disclosure. These injectable solutions use injectable carriers known within the art, such as injectable sterile saline or phosphate-buffered saline carriers and the like.

Injection dose levels of injectable solutions comprised of compounds of Formula I or their pharmaceutically acceptable salts are provided in any desired dosage, for example, from about 0.1 mg/kg/hour to at least 10 mg/kg/hour, all for from about 1 to about 120 hours and especially 24 to 96 hours. In one embodiment, a preloading bolus of from about 0.1 mg/kg to about 10 mg/kg or more comprised of the compounds of Formula I or their pharmaceutically acceptable salts may also be administered to achieve adequate steady state levels. The maximum total dose is not expected to exceed about 2-5 g/day for a 40 to 80 kg human patient.

Transdermal doses are generally selected to provide similar or lower blood levels than are achieved using injection doses. Transdermal compositions are typically formulated as a topical ointment or cream containing the compound of Formula I or its pharmaceutically acceptable salt, for example in an amount ranging from about 0.01 to about 20% by weight, in another embodiment, from about 0.1 to about 20% by weight, in still another embodiment, from about 0.1 to about 10% by weight, and in still a different embodiment from about 0.5 to about 15% by weight. When formulated as an ointment, the compound of Formula I or its pharmaceutically acceptable salt will typically be combined with either a suitable delivery polymeric composition, or a paraffinic or a water-miscible ointment base. Alternatively, the compound of Formula I or its pharmaceutically acceptable salt may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compound of Formula I or its pharmaceutically acceptable salt can be administered by a transdermal device. Transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compound of Formula I or its pharmaceutically acceptable salt can also be administered in sustained release forms or from sustained release drug delivery systems. A description of representative sustained release materials can be found in *Remington's Pharmaceutical Sciences.*

In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water). In a more particular embodiment, the formulation comprises Captisol®.

The following formulation examples illustrate non-limiting representative pharmaceutical compositions that may be prepared in accordance with this disclosure for the purpose of illustration only. The present invention is specifically not limited to the following pharmaceutical compositions. Although the examples in the formulations herein refer to compounds of Formula I it is understood that the pharmaceutically acceptable salt, solvate, hydrate, prodrug, stereoisomer, tautomer, rotamer, N-oxide and/or substituted derivative salt, solvate, hydrate, prodrug, stereoisomer, tautomer, rotamer, N-oxide and/or substituted derivative thereof may be used in their stead. Thus, for example, if the compound of Formula I is present in the formulation as its salt, the weight ratio is to be based upon the weight of the compound of Formula I present in the formulation without taking into account the weight attributable to the salt thereof.

Formulation 1—Tablets

A compound of Formula I may be admixed as a dry powder with a dry gelatin binder in an approximate 1:2 weight ratio. A minor amount of magnesium stearate is added as a lubricant. The mixture is formed into 240-270 mg tablets (80-90 mg of a compound of Formula I per tablet) in a tablet press.

Formulation 2—Capsules

A compound of Formula I may be admixed as a dry powder with a starch diluent in an approximate 1:1 weight ratio. The mixture is filled into 250 mg capsules (125 mg of a compound of Formula I per capsule).

Formulation 3—Liquid

A compound of Formula I (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of Formula I can be admixed as a dry powder with a dry gelatin binder in an approximate 1:2 weight ratio. A minor amount of magnesium stearate is added as a lubricant. The mixture is formed into 450-900 mg tablets (150-300 mg of a compound of Formula I) in a tablet press. In other embodiments, there is between 10 and 500 mg of a compound of Formula I in the oral tablet.

Formulation 5—Injection

A compound of Formula I can be dissolved or suspended in a buffered sterile saline injectable aqueous medium to a concentration of approximately 5, or 10, or 15, or 20, or 30 or 50 mg/mL.

Formulation 6—Tablets

A compound of Formula I may be admixed as a dry powder with a dry gelatin binder in an approximate 1:2 weight ratio. A minor amount of magnesium stearate is added as a lubricant. The mixture is formed into 90-150 mg tablets (30-50 mg of a compound of Formula I per tablet) in a tablet press.

Formulation 7—Tablets

A compound of Formula I may be admixed as a dry powder with a dry gelatin binder in an approximate 1:2 weight ratio. A minor amount of magnesium stearate is added as a lubricant. The mixture is formed into 30-90 mg tablets (10-30 mg of a compound of Formula I per tablet) in a tablet press.

Formulation 8—Tablets

A compound of Formula I may be admixed as a dry powder with a dry gelatin binder in an approximate 1:2 weight ratio. A minor amount of magnesium stearate is added as a lubricant. The mixture is formed into 0.3-30 mg tablets (0.1-10 mg of a compound of Formula I per tablet) in a tablet press.

Formulation 9—Tablets

A compound of Formula I may be admixed as a dry powder with a dry gelatin binder in an approximate 1:2 weight ratio. A minor amount of magnesium stearate is added as a lubricant. The mixture is formed into 150-240 mg tablets (50-80 mg of a compound of Formula I per tablet) in a tablet press.

Formulation 10—Tablets

A compound of Formula I may be admixed as a dry powder with a dry gelatin binder in an approximate 1:2 weight ratio. A minor amount of magnesium stearate is added as a lubricant. The mixture is formed into tablets (5-1000 mg of a compound of Formula I per tablet) in a tablet press.

Methods of Use in Medical Therapy

A compound of Formula I described herein or its salt or derivative as described herein or a pharmaceutically acceptable composition thereof has anti-estrogenic activity useful to treat any disorder modulated, mediated or affected by the estrogen receptor or as otherwise described herein. Nonlimiting examples of disorders are estrogen and/or progesterone negative or positive breast cancer, ovarian, endometrial, vaginal cancer, endometriosis, lung cancer, bone cancer, colorectal endometrial cancer, prostate cancer, uterine cancer and an estrogen receptor-α dysfunction associated with cancer. They can be used in the treatment of lung and bronchial cancers that express estrogen receptors.

Compounds described herein can also be used as adjunctive therapy or combination therapy with another active agent. For example, a therapeutically effective amount of the compound can be used in combination with another anti-cancer agent, especially for estrogen receptor positive breast cancer, but in some embodiments, for estrogen receptor negative breast cancer.

In some embodiments, compounds of Formula I or pharmaceutically acceptable salts thereof are used in combination or alternation with another anti-cancer agent for the treatment of cancer, as described more fully herein. In some embodiments, compounds of Formula I or its pharmaceutically acceptable salts thereof are used in combination or alternation with estrogen or a partial estrogen receptor antagonist for the treatment of a postmenopausal disorder.

In some embodiments, a compound of Formula I or its pharmaceutically acceptable salt is used to treat local, advanced or metastatic breast cancer that is positive for expression of estrogen receptors, progesterone receptors or both (receptor positive advanced breast cancer). In an alternative embodiment, the compound of Formula I or its pharmaceutically acceptable salt is used to treat estrogen or progesterone receptor negative breast cancer. A compound of Formula I or its pharmaceutically acceptable salt can be used as the initial treatment of advanced breast cancer in patients who have never received previous hormonal therapy for advanced breast cancer, either by itself or in combination with one or more other anti-cancer agents or otherwise known to those skilled in the art. It is also useful for second line therapy for treatment after a previous anti-hormonal therapy has failed, either by itself or in combination with another anticancer agent, for example, a targeted therapy such as an mTOR inhibitor such as everolimus, or a CDK4/6 inhibitor such as palbociclib, abemaciclib, or ribociclib.

Compounds of Formula I or their pharmaceutically acceptable salts are also useful as adjunctive therapy after or instead of chemotherapy, radiation or surgery. Such adjuvant use is often used for several years, perhaps up to 5 years or more, after chemotherapy or other therapies have been concluded, but may optimally be continued for additional years.

Compounds of Formula I or their pharmaceutically acceptable salts are also useful for the prevention of breast cancer in women at high risk and can be taken for any desired time period, including indefinitely. For example, a patient, typically a woman, with a family history of breast cancer, or who has been determined to carry a mutation in the BRACA1 or BRACA2 gene or other genes that predispose a patient to breast cancer may choose to use such preventative treatment instead of a mastectomy or other intervention. The compounds of Formula I or their pharmaceutically acceptable salts described herein are also useful as neoadjuvants to shrink large tumors prior to surgical removal, both to enable breast conservative surgery and to reduce the risk of recurrence.

Selective estrogen receptor modulators (SERMs) such as tamoxifen, raloxifene, lasofoxifene, and bazedoxifene additionally have application as hormone replacement therapy to prevent osteoporosis and other disorders such as hot flashes, etc. in post-menopausal women, a use that depends on their partial estrogen like action, for example, on bone. The compound of Formula I or its pharmaceutically acceptable salts described herein can be employed in combination with an estrogen or a selective estrogen receptor modulator to block the unwanted estrogenic activity of the therapy. The complete anti-estrogen is dosed in the amount to prevent the adverse action of the estrogen or estrogen receptor modulator on the uterus and mammary gland yet allowing the beneficial action of estrogen on bone and vasomotor symptoms.

Compounds of Formula I or their pharmaceutically acceptable salts can be administered for the treatment of cancer, and in particular breast cancer in combination or association with Herceptin, Tykerb, a CDK4/6 inhibitor such as palbociclib (originally known as PD-0332991), abemaciclib, ribociclib, an mTOR inhibitor such as Novartis' everolimus and other rapamycin analogs such rapamycin and temsirolimus, Millennium's MLN0128 TORC1/2 inhibitor, an EFGR-family inhibitor such as trastuzumab, pertuzumab, ado-trastuzumab emtansine, erlotinib, gefitinib, neratinib and similar compounds, a PI3 Kinase Inhibitor such as perifosine, CAL101, BEZ235, XL147, XL765, GDC-0941, and IPI-145, a histone deacetylase inhibitor such as vorinostat, romidepsin, panobinostat, valproic acid, etinostat, and belinostat.

In some embodiments, compounds of any of the Formulae described herein can be administered in combination with targeted anti-cancer immune therapies including PD-1 inhibitors such as nivolumab, pembrolizumab, pidilizumab, or BMS 936559, and/or PD-L1 inhibitors such as atezolizumab, avelumab, or durvalumab.

In another method of treatment aspect, provided herein is a method of treating a mammal susceptible to or afflicted with a condition influenced by estrogen receptor by administering to a subject in need thereof a compound of Formula I or its pharmaceutically acceptable salt thereof.

Given the central role of ER-α in breast cancer development and progression, compounds disclosed herein are useful in the treatment of breast cancer, either alone or in combination with other agents that can modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agents used to treat breast cancer, including but not limited to aromatase inhibitors, anthracyclines, platins, nitrogen mustard alkylating agents, and taxanes. I(l)lustrative agents used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

Generally, ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used in the treatment of an estrogen receptor dependent or estrogen receptor mediated disease or condition in a mammal.

In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects.

In some embodiments, the estrogen receptor dependent or estrogen receptor mediated disease or condition is selected from bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, and infertility.

In some embodiments, the cancer is an estrogen-sensitive cancer or an estrogen receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors-resistant.

In some embodiments, compounds disclosed herein are used to treat hormone receptor positive metastatic breast cancer in a postmenopausal woman with disease progression following anti-estrogen therapy.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naive.

In some embodiments, compounds disclosed herein are used to treat cancer in a mammal, wherein the mammal is being treated for cancer with at least one anti-cancer agent.

In one embodiment, the cancer is a hormone refractory cancer.

Accordingly, in some embodiments, the present invention provides a compound of Formula I:

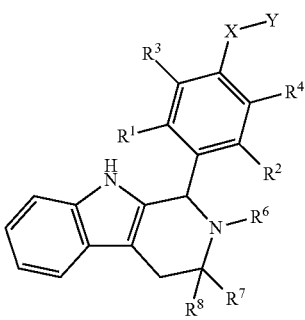

I wherein:
X is —CH$_2$— or —O—;
Y is

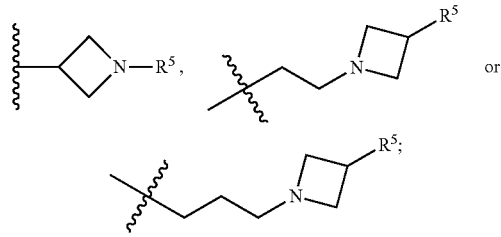

R$^1$, R$^2$, R$^3$, and R$^4$ are each independently selected from hydrogen or halo;
R$^5$ is hydrogen, C$_1$-C$_6$alkyl, C$_1$-C$_6$haloalkyl, C$_2$-C$_6$alkenyl, C$_1$-C$_4$(C$_3$-C$_6$cycloalkyl) or C$_1$-C$_6$heteroalkyl;
R$^6$ is hydrogen, C$_1$-C$_6$alkyl, C$_1$-C$_6$haloalkyl or C$_1$-C$_4$(C$_3$-C$_6$cycloalkyl);
R$^7$ and R$^8$ are each independently selected from hydrogen or C$_1$-C$_6$alkyl;
or a pharmaceutically acceptable salt thereof.

In some embodiments, X is —O—. In some embodiments, wherein X is —CH$_2$—.

In some embodiments, Y is

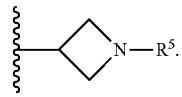

In some embodiments, Y is

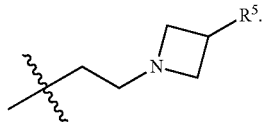

In some embodiments, X is —O— and Y is

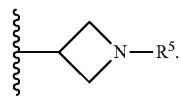

In some embodiments, X is —O— and Y is

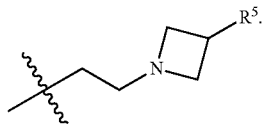

In some embodiments, R$^5$ is C$_1$-C$_6$alkyl. In some embodiments, R$^5$ is selected from the group consisting of methyl, ethyl, propyl and butyl. In some embodiments, R$^5$ is propyl. In some embodiments, R$^5$ is C$_1$-C$_6$alkyl or C$_1$-C$_6$haloalkyl. In some embodiments, R$^5$ is C$_1$-C$_6$haloalkyl. In some embodiments, R$^5$ is selected from the group consisting of —CH$_2$F, CHF$_2$ or CF$_3$. In some embodiments, R$^5$ is CH$_2$F.

In some embodiments, R$^6$ is hydrogen, C$_1$-C$_6$alkyl or C$_1$-C$_6$haloalkyl. In some embodiments, R$^6$ is C$_1$-C$_6$haloalkyl. In some embodiments, R$^6$ is —CH$_2$CF(CH$_3$)$_2$.

In some embodiments, R$^7$ and R$^8$ are each independently selected from hydrogen or C$_1$-C$_6$alkyl. In some embodiments, R$^7$ is methyl and R$^8$ is hydrogen.

In some embodiments, the present invention provides a compound of Formula I(a):

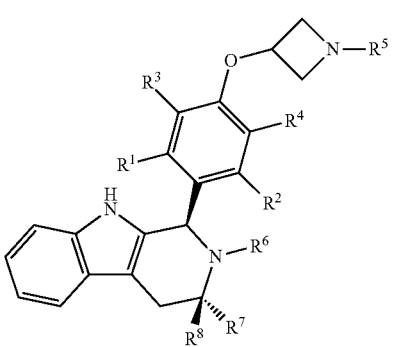

I(a)

or a pharmaceutically acceptable salt thereof.

In some embodiments, R$^1$, R$^2$, R$^3$, and R$^4$ are each independently selected from hydrogen or halo. In some embodiments, R$^1$, R$^2$, R$^3$ and R$^4$ are hydrogen. In some embodiments, R$^1$, R$^2$, R$^3$ and R$^4$ are hydrogen or fluoro.

In some embodiments, R$^5$ is C$_1$-C$_6$alkyl. In some embodiments, R$^5$ is selected from the group consisting of methyl, ethyl, propyl and butyl. In some embodiments, R$^5$ is propyl.

In some embodiments, $R^6$ is hydrogen, $C_1$-$C_6$alkyl or $C_1$-$C_6$haloalkyl. In some embodiments, $R^6$ is $C_1$-$C_6$haloalkyl. In some embodiments, $R^6$ is —$CH_2CF(CH_3)_2$.

In some embodiments, $R^7$ and $R^8$ are each independently selected from hydrogen or $C_1$-$C_6$alkyl. In some embodiments, $R^7$ is methyl and $R^8$ is hydrogen.

In some embodiments, the present invention provides a compound of Formula I(b):

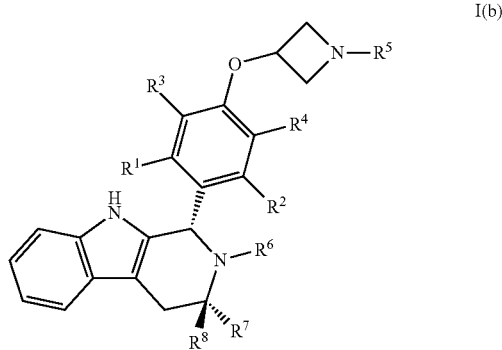

I(b)

or a pharmaceutically acceptable salt thereof.

In some embodiments, $R^1$, $R^2$, $R^3$, and $R^4$ are each independently selected from hydrogen or halo. In some embodiments, $R^1$, $R^2$, $R^3$ and $R^4$ are hydrogen. In some embodiments, $R^1$, $R^2$, $R^3$ and $R^4$ are hydrogen or fluoro.

In some embodiments, $R^5$ is $C_1$-$C_6$alkyl. In some embodiments, $R^5$ is selected from the group consisting of methyl, ethyl, propyl and butyl. In some embodiments, $R^5$ is propyl.

In some embodiments, $R^6$ is hydrogen, $C_1$-$C_6$alkyl or $C_1$-$C_6$haloalkyl. In some embodiments, $R^6$ is $C_1$-$C_6$haloalkyl. In some embodiments, $R^6$ is —$CH_2CF(CH_3)_2$.

In some embodiments, $R^7$ and $R^8$ are each independently selected from hydrogen or $C_1$-$C_6$alkyl. In some embodiments, $R^7$ is methyl and $R^8$ is hydrogen.

In some embodiments, the present invention provides a compound of Formula I(c):

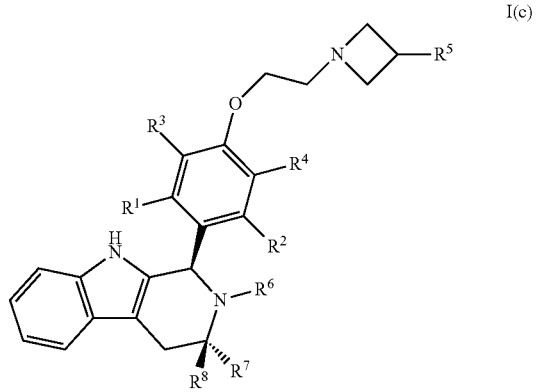

I(c)

or a pharmaceutically acceptable salt thereof.

In some embodiments, $R^1$, $R^2$, $R^3$, and $R^4$ are each independently selected from hydrogen or halo. In some embodiments, $R^1$, $R^2$, $R^3$ and $R^4$ are hydrogen. In some embodiments, $R^1$, $R^2$, $R^3$ and $R^4$ are hydrogen or fluoro.

In some embodiments, $R^5$ is $C_1$-$C_6$alkyl or $C_1$-$C_6$haloalkyl. In some embodiments, $R^5$ is $C_1$-$C_6$haloalkyl. In some embodiments, $R^5$ is selected from the group consisting of —$CH_2F$, $CHF_2$ or $CF_3$. In some embodiments, $R^5$ is $CH_2F$.

In some embodiments, $R^6$ is hydrogen, $C_1$-$C_6$alkyl or $C_1$-$C_6$haloalkyl. In some embodiments, $R^6$ is $C_1$-$C_6$haloalkyl. In some embodiments, $R^6$ is —$CH_2CF(CH_3)_2$.

In some embodiments, $R^7$ and $R^8$ are each independently selected from hydrogen or $C_1$-$C_6$alkyl. In some embodiments, $R^7$ is methyl and $R^8$ is hydrogen.

In some embodiments, the present invention provides a compound of Formula I(d):

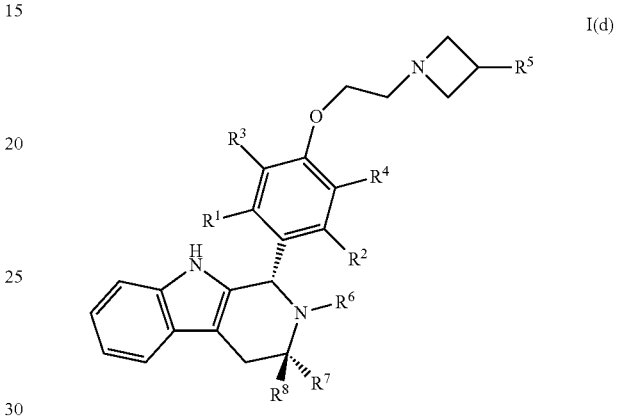

I(d)

or a pharmaceutically acceptable salt thereof.

In some embodiments, $R^1$, $R^2$, $R^3$, and $R^4$ are each independently selected from hydrogen or halo. In some embodiments, $R^1$, $R^2$, $R^3$ and $R^4$ are hydrogen. In some embodiments, $R^1$, $R^2$, $R^3$ and $R^4$ are hydrogen or fluoro.

In some embodiments, $R^5$ is $C_1$-$C_6$alkyl or $C_1$-$C_6$haloalkyl. In some embodiments, $R^5$ is $C_1$-$C_6$haloalkyl. In some embodiments, $R^5$ is selected from the group consisting of —$CH_2F$, $CHF_2$ or $CF_3$. In some embodiments, $R^5$ is $CH_2F$.

In some embodiments, $R^6$ is hydrogen, $C_1$-$C_6$alkyl or $C_1$-$C_6$haloalkyl. In some embodiments, $R^6$ is $C_1$-$C_6$haloalkyl. In some embodiments, $R^6$ is —$CH_2CF(CH_3)_2$.

In some embodiments, $R^7$ and $R^8$ are each independently selected from hydrogen or $C_1$-$C_6$alkyl. In some embodiments, $R^7$ is methyl and $R^8$ is hydrogen.

In some embodiments, the present invention provides a compound which has the chemical structure:

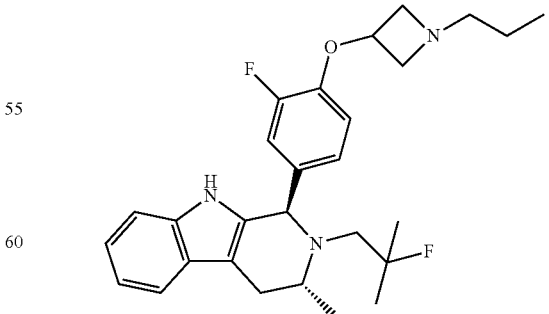

or a pharmaceutically acceptable salt thereof.

In some embodiments, the present invention provides a compound which has the chemical structure:

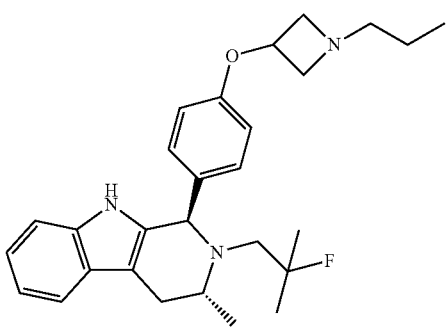 [SMILES: CCCN1CC(Oc2ccc([C@@H]3c4[nH]c5ccccc5c4C[C@@H](C)N3CC(C)(C)F)cc2)C1]

or a pharmaceutically acceptable salt thereof.

In some embodiments, the present invention provides a compound which has the chemical structure:

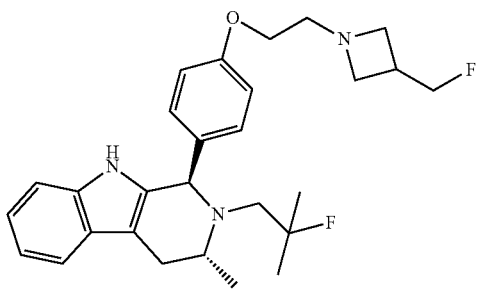 [SMILES: C[C@@H]1Cc2c([nH]c3ccccc23)[C@@H](c2ccc(OCCN3CC(CF)C3)cc2)N1CC(C)(C)F]

or a pharmaceutically acceptable salt thereof.

In some embodiments, the present invention provides a compound which has the chemical structure:

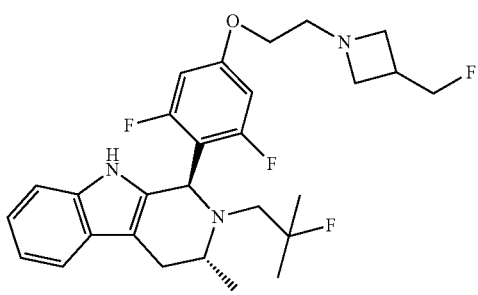 [SMILES: C[C@@H]1Cc2c([nH]c3ccccc23)[C@@H](c2c(F)cc(OCCN3CC(CF)C3)cc2F)N1CC(C)(C)F]

or a pharmaceutically acceptable salt thereof.

In some embodiments, the present invention provides a composition comprising a compound of any of the Formulae described herein and a pharmaceutically acceptable carrier. In some embodiments, the carrier is suitable for oral delivery.

In some embodiments, the present invention provides a method for treating a disorder mediated by the estrogen receptor in a patient, which comprises administering to the patient a therapeutically effective amount of any of the Formulae described herein, optionally in a pharmaceutically acceptable carrier. In some embodiments, the disorder is breast cancer.

In some embodiments, the disorder is selected from the group consisting of ovarian cancer, endometrial cancer, vaginal cancer, lung cancer, bone cancer, uterine cancer and endometriosis.

In some embodiments, the method further comprises administering a compound of the present invention in combination or alternation with another anti-cancer agent for the treatment of cancer.

In some embodiments, the method further comprises administering the compound in combination or alternation with an estrogen or a partial estrogen receptor antagonist for the treatment of a postmenopausal disorder. In some embodiments, the patient is a human.

As used herein, the term "combination" means simultaneous or sequential administration of two or more therapeutic agents. In some embodiments, a compound of any of the Formulae described herein can be administered before, during or after administration of an additional therapeutic agent, for example, an estrogen or a partial estrogen receptor antagonist.

In some embodiments, the present invention provides a compound of any of the Formulae described herein for use in medical treatment.

In some embodiments, the present invention provides a compound of any of the Formulae described herein for use in treating a disorder selected from the group consisting of ovarian cancer, endometrial cancer, vaginal cancer, lung cancer, bone cancer, uterine cancer and endometriosis. In some such embodiments, the disorder is breast cancer.

In some embodiments, the present invention provides a compound of any of the Formulae described herein for use in combination with an estrogen or a partial estrogen receptor antagonist for the treatment of a postmenopausal disorder.

In some embodiments, the present invention provides a compound of any of the Formulae described herein for use in the manufacture of a medicament for treating a disorder selected from the group consisting of ovarian cancer, endometrial cancer, vaginal cancer, lung cancer, bone cancer, uterine cancer and endometriosis. In some such embodiments, the disorder is breast cancer.

In some embodiments, the present invention provides a compound of any of the Formulae described herein for use in the manufacture of a medicament for treating a disorder selected from the group consisting of ovarian cancer, endometrial cancer, vaginal cancer, lung cancer, bone cancer, uterine cancer and endometriosis, wherein the medicament is formulated for use in combination with an estrogen or a partial estrogen receptor antagonist for the treatment of a postmenopausal disorder.

Preparation of Compounds

Compounds provided herein can be prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M.

Wuts, *Protecting Groups in Organic Synthesis*, Second Edition, Wiley, New York, 1991, and references cited therein.

Compounds provided herein may be isolated and purified by known standard procedures. Such procedures include (but are not limited to) recrystallization, column chromatography or HPLC. The following schemes are presented with details as to the preparation of representative compounds of Formula I that have been listed herein. The compounds provided herein may be prepared from known or commercially available starting materials and reagents by one skilled in the art of organic synthesis.

The following non-limiting Schemes and Examples for the preparation of representative compounds are exemplary of the methods used to prepare the compounds of Formula I. General processes for preparing compounds of the instant invention are provided as further embodiments of the invention and are illustrated in the following Schemes. In the Schemes, unless indicated to the contrary, X, Y, $R^1$, $R^2$, $R^3$, $R^4$, $R^5$, $R^6$, $R^7$ and $R^8$ are as defined hereinabove.

The following abbreviations may be used in the Examples below: aq. (aqueous); ACN (acetonitrile); CSA (camphorsulfonic acid); d (day or days); DCM (dichloromethane); DEA (diethylamine); DHP (dihydropyran); DMF (N,N-dimethylformamide); DIPEA (N,N-diisopropylethylamine); DMAP (4-dimethylaminopyridine); DMSO (dimethyl sulphoxide); EA (ethyl acetate); ee (enantiomeric excess); equiv. (equivalent); ethanol (EtOH); h (hour or hours); Hex (hexanes); HPLC (high-performance liquid chromatography); IPA (isopropyl alcohol); KHMDS (potassium bis(trimethylsilyl)amide); LAH (lithium aluminum hydride); LCMS (liquid chromatography-mass spectrometry); LDA (lithium diisopropylamide); LiHMDS (lithium bis(trimethylsilyl)amide); MeOH (methanol); min (minute or minutes); NMR (nuclear magnetic resonance); Pd/C (palladium on carbon); $PPh_3O$ (triphenylphosphine oxide); Pt/C (platinum on carbon); rb (round-bottomed); Rf (retention factor); rt or RT (room temperature); SM (starting material); TEA (triethylamine); THF (tetrahydrofuran); THP (tetrahydropyran); TLC (thin layer chromatography); TsOH (p-toluenesulfonic acid or tosylic acid); and UV (ultraviolet).

Additional embodiments within the scope provided herein are set forth in non-limiting fashion elsewhere herein and in the examples herein below. It should be understood that these examples are for illustrative purposes only and are not to be construed as limiting in any manner.

The following non-limiting Schemes and examples are illustrative of the present disclosure:

SCHEME A

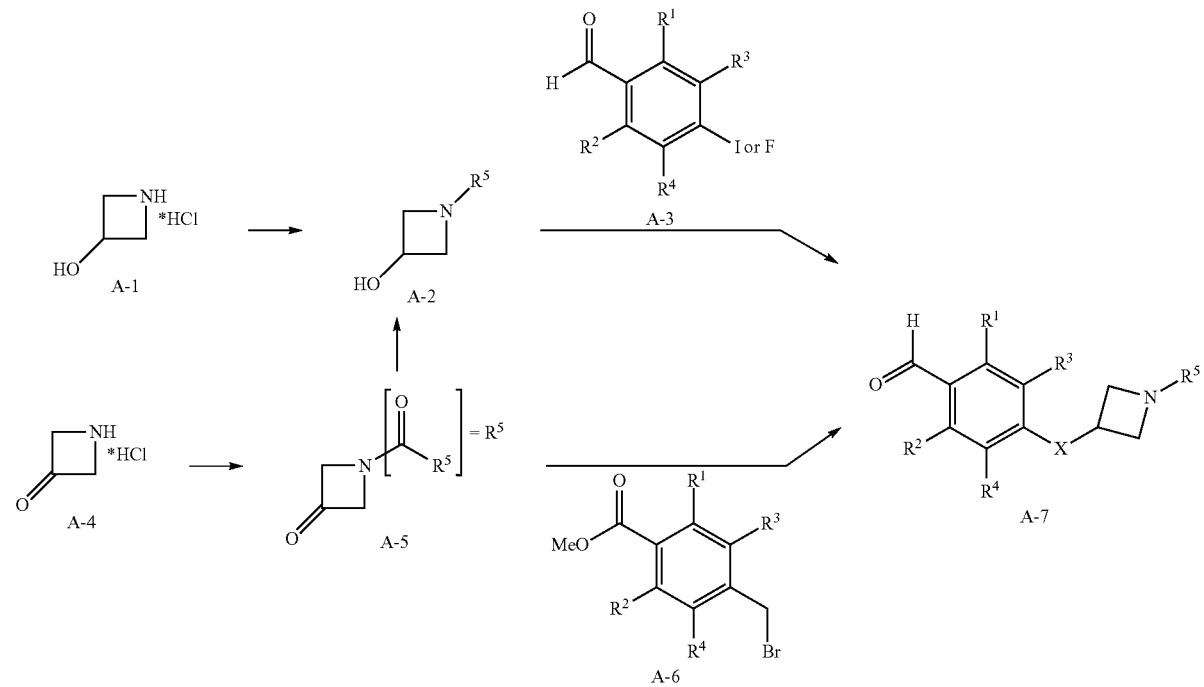

As exemplified in Scheme A, key intermediates for the synthesis of compounds of Formula I can be synthesized from readily available functionalized azetidines A-1 and A-4.

Compound A-2 can be prepared by direct alkylation of A-1 or its O-protected analog using a suitably functionalized alkylating agent containing a moiety, such as $LCH_2R^5$ under amine alkylation conditions, wherein L is a leaving group, such as halide (e.g., Br, Cl, I) or other leaving group, such as OTs, OBs, ONs, OMs, triflate, nonaflate, tresylate and the like. Compound A-2 can also be prepared by reductive amination of A-1 with $HC(O)R^5$ in the presence of hydrogen and a hydrogenation catalyst, such as Pt, Pd and the like or in the presence of weak acid such as AcOH and a reducing agent such as $NaHB(OAc)_3$ and the like. Alternatively, A-2 is prepared by reacting $XC(O)R^5$, where X is a leaving group, with A-4 under amide forming conditions to form the amidoketone, A-5, followed by reduction of the resulting amidoketone A-5 using reducing agents known in the art, such as LAH and the like. Nucleophilic aromatic substitution by A-2 of a halide on a functionalized benzaldehyde A-3 by either aryl nucleophilic substitution (for fluoro-substituted A-3) or via Ullman coupling conditions (for iodo-substituted A-3) under conditions known in the art gives rise to a key intermediate A-7, wherein X is O. Similarly, the corresponding intermediate A-7 where X is S can be prepared by preparing the halides from a azetidine A-1 under nucleophilic substitution reaction conditions, using, for example, hydrochloric acid or hydrobromic acid or hydroiodic acid to form the corresponding chloride, bromide or iodide, respectively, or by reacting azetidine A-1 with an inorganic acid halide, such as $SOCl_2$, $PCl_5$, $PCl_3$, $POCl_3$, and the like to form the corresponding chloride. The product thereof is reacted with a sulfide, such as sodium hydrogen sulfide or sodium thioacetate and the like to form the corresponding thiol or thio ester. The thiol or thio ester is reacted with suitably functionalized alkylating agent containing a moiety, such as $LCH_2R^5$ under amine alkylation conditions, wherein L is a leaving group, such as halide (e.g., Br, Cl, I) or another leaving group, such as OTs, OBs, ONs, OMs, triflate, nonaflate, tresylate and the like, and the resulting product is reacted with A-3 to form the compound of A-7, wherein X is S.

To form compounds wherein X is $CH_2$, amidoketone A-5 can be coupled to ester A-6 via the phosphonium salt of A-6 in a Wittig reaction under Wittig forming conditions to form the alkene A-6.1.

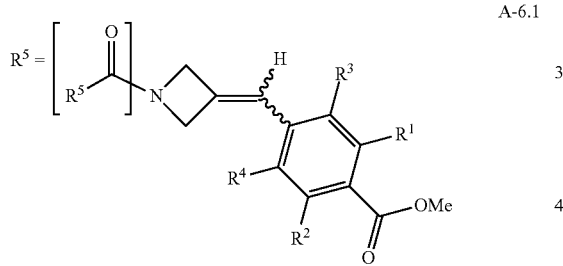

A-6.1

Reduction of the resulting alkene followed by reduction of the amide and ester functions under reducing conditions known in the art provides the benzylic alcohol A-6.2.

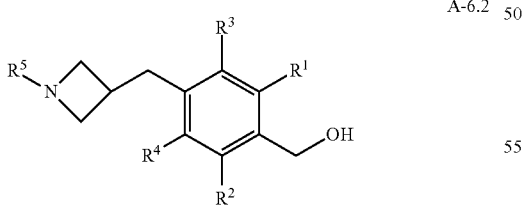

A-6.2

Oxidation of the benzyl alcohol using oxidizing agents known in the art such as copper chromite; DMSO; Collins' reagent; Corey's reagent; pyridinium dichromate; sodium dichromate in water; and the like or DMSO, dicyclohexylcarbodiimide and anhydrous phosphoric acid under Moffatt oxidation conditions or anhydrous phosphoric acid and oxalyl chloride under Swern oxidation conditions and the like furnishes the aldehyde A-7, wherein X is $CH_2$.

SCHEME B

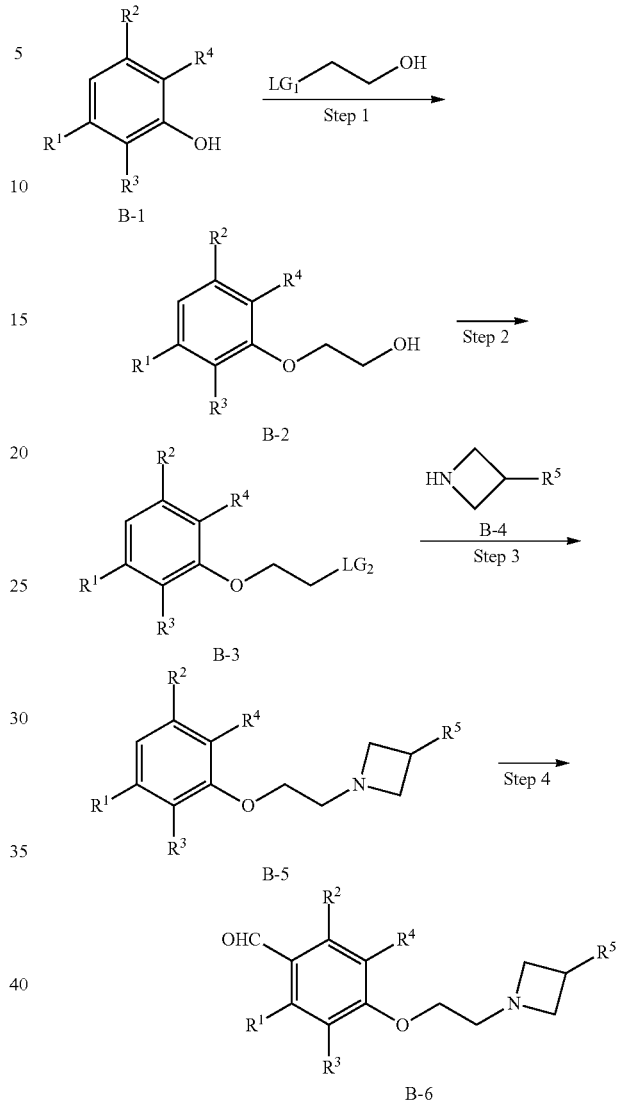

As exemplified in Scheme B, key intermediates for the synthesis of compounds of Formula I can be synthesized from a readily available functionalized phenol B-1. In Step 1, compound B-2 can be prepared by direct alkylation of B-1 by using a suitably functionalized alkylating agent containing a moiety, such as $LG_1CH_2CH_2OH$ under phenol alkylation conditions, wherein $LG_1$ is a leaving group, such as a halide (e.g., Br, Cl, I) or other leaving group, such as OTs, OBs, ONs, OMs, triflate, nonaflate, tresylate and the like. In one embodiment, the phenol alkylating conditions include the use of a base and an organic solvent optionally at an elevated temperature. In one embodiment, the base is cesium carbonate. In one embodiment, the organic solvent is N,N-dimethylformamide. In Step 2, the B-2 alcohol group can be converted to a leaving group $LG_2$ by using conditions known to one skilled in the art. The leaving group, $LG_2$, can be a halide (e.g., Br, Cl, I) or other leaving group, such as OTs, OBs, ONs, OMs, triflate, nonaflate, tresylate and the like. In one embodiment, B-2 is treated with methanesulfonyl chloride; a base, such as triethylamine; an organic solvent, such as dichloromethane, at a reduced temperature of about 0° C.

In Step 3, an amine, B-4, is treated with B-3, a base and an organic solvent at an elevated temperature to generate the amine, B-5, according to conditions known to those skilled in the art. In one embodiment, the base is potassium carbonate. In one embodiment, the organic solvent is acetonitrile. In one embodiment, the amine, B-4, is in the form of a salt. In one embodiment, B-4 is a hydrochloride salt. In Step 4, compound B-5 is formylated according to conditions known to those of skill in the art. In one embodiment, B-5 is treated with a base and tetramethylethylenediamine at a reduced temperature followed by N,N-dimethylformamide at room temperature to generated B-6. In one embodiment, the base is n-butyllithium. In one embodiment, the reduced temperature is about −78° C. See, WO 2005/080380.

using conditions known to one skilled in the art. The leaving group, $LG_3$, can be a halide (e.g., Br, Cl, I) or other leaving group, such as OTs, OBs, ONs, OMs, triflate, nonaflate, tresylate and the like. In one embodiment, C-4 is treated with trifluoromethanesulfonic anhydride; a base, such as 2,6-lutidine; an organic solvent, such as dichloromethane, at a reduced temperature of about 0° C. In Step 4, amine C-3 is treated with C5, a base, and an organic solvent according to methods known to one skilled in the art. In one embodiment, C-3 is treated with C-5, a base such as diisopropylethylamine and organic solvents such as dichloromethane and 1,4-dioxanes at an elevated temperature of about 90° C. to generate C-6.

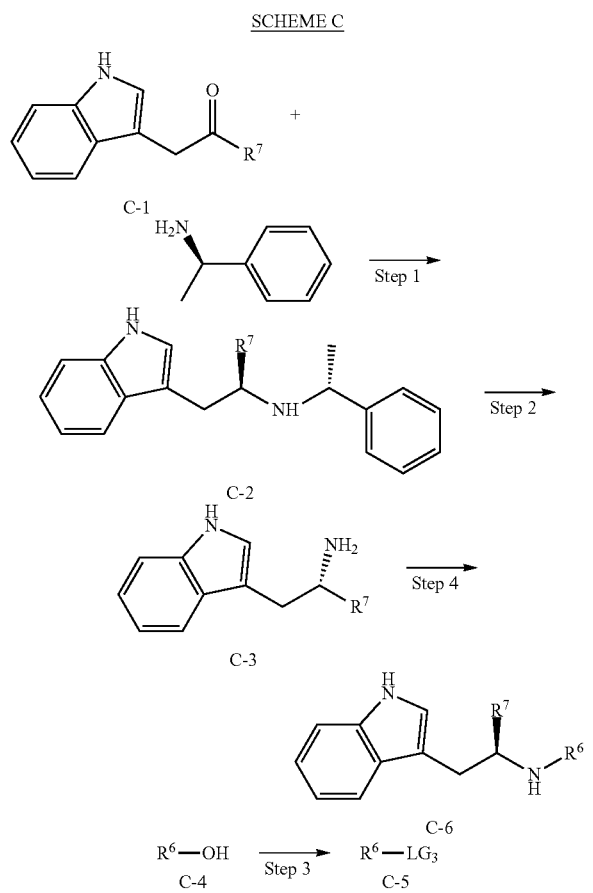

SCHEME C

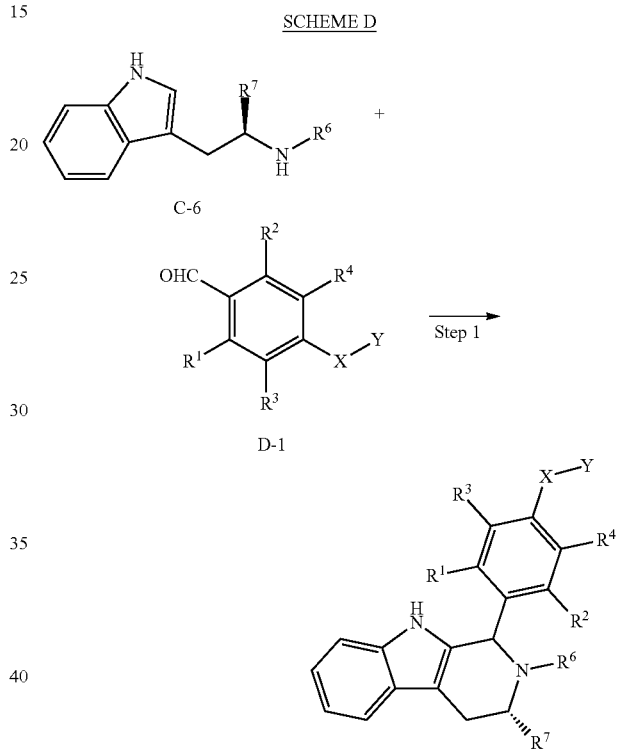

SCHEME D

As exemplified in Scheme D, compounds of Formula I can be synthesized from amine C-6 and an aldehyde such as D-1 using Pictet-Spengler reaction conditions known to those of skill in the art. For example, amine C-6 is treated with aldehyde D-1 in an anhydrous solvent such as toluene; an acid such as glacial acetic acid; molecular sieves, a nitrogen atmosphere in the dark at an elevated temperature of about 80° C. to generate compounds of Formula I.

Section 1: Preparation of Aldehydes

Example 1. Preparation of 2,6-difluoro-4-(2-(3-(fluoromethyl)azetidin-1-yl)ethoxy)-benzaldehyde As exemplified in Scheme C, key intermediates for the synthesis of compounds of Formula I can be synthesized from a readily available ketone C-1. In Step 1, C-1 is treated with an amine, such as (R)-(+)-1-phenylethylamine; an organic solvent such as dichloromethane and a reducing reagent, such as sodium triacetoxyborohydride optionally at a reduced temperature to generate amine, C-2. In Step 2, amine C-2 is deprotected according to methods known to those skilled in the art. In Step 2, C-2 is treated with a catalyst such as 20% Pd(OH)$_2$ on carbon wet with water; an organic solvent, such as methanol and hydrogen gas at about 50 psi to generate the indole C-3.

As also exemplified in Scheme C, key intermediates for the synthesis of compounds of Formula I can be synthesized from a readily available alcohol C-4. In Step 3, the C-4 alcohol group can be converted to a leaving group $LG_3$ by

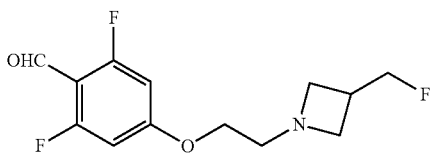 [SMILES: O=Cc1c(F)cc(OCCN2CC(CF)C2)cc1F]

Step 1. Preparation of 2-(3,5-difluorophenoxy)ethanol

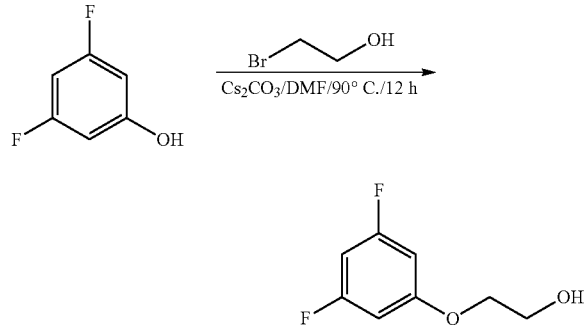

A suspension of 3,5-difluorophenol (5.07 g, 39.0 mmol, 1.0 equiv.), 2-bromoethanol (4.14 mL, 58.5 mmol, 1.5 equiv.) and cesium carbonate (19.05 g, 58.5 mmol, 1.5 equiv.) in DMF (100 mL) was heated to 90° C. for 12 h. TLC (10% EA/Hex) indicated the reaction was nearly complete. The reaction was diluted with EA (200 mL) and washed with water (3×100 mL), brine, dried over anhydrous sodium sulfate, filtered and concentrated to afford the product (4.86 g, 71.6%).

$^1$H NMR (300 MHz, CDCl$_3$), δ 6.46-6.40 (m, 3H), 4.05 (t, J=4.2 Hz, 2H), 3.99-3.94 (m, 2H), 1.94 (t, J=6.0 Hz, 1H).

Step 2. Preparation of 2-(3,5-difluorophenoxy)ethyl methanesulfonate

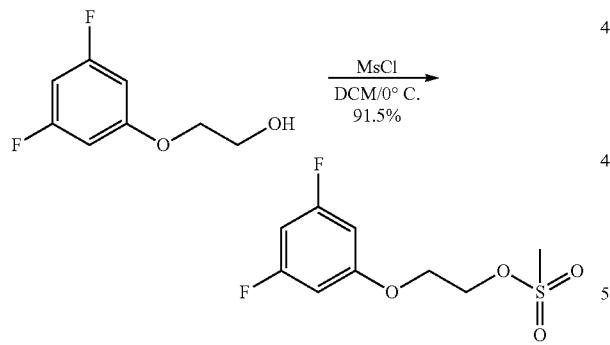

Mesyl chloride (0.77 mL, 9.9 mmol, 1.0 equiv.) was added over 10 minutes to a solution of 2-(3,5-difluorophenoxy)ethanol (1.66 g, 9.5 mmol, 1.0 equiv.) and triethylamine (1.80 mL, 12.9 mmol, 1.4 equiv.) in DCM (120 mL.) at 0° C. The reaction was stirred at 0° C. for 1 h. TLC (5% MeOH/DCM) indicated the reaction was complete. Saturated sodium bicarbonate solution was added to the reaction and stirred at 0° C. for 30 minutes. The organic layer was washed with brine, dried over anhydrous sodium sulfate, filtered and concentrated. The residue was used directly without purification.

$^1$H NMR (300 MHz, CDCl$_3$), δ 6.50-6.43 (m, 3H), 4.56 (t, J=4.8 Hz, 2H), 4.22 (t, J=4.8 Hz, 2H), 3.08 (s, 3H).

Step 3. Preparation of 1-(2-(3,5-difluorophenoxy)ethyl)-3-(fluoromethyl)azetidine

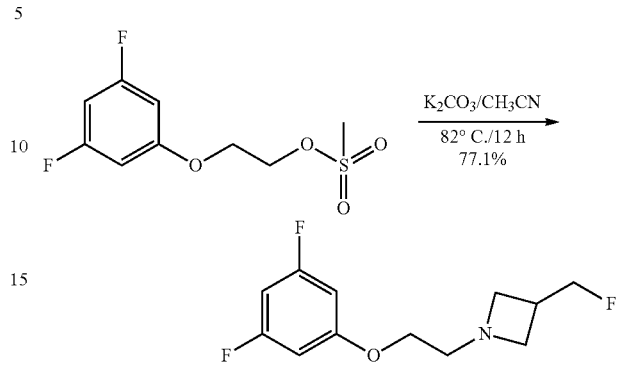

A suspension of 2-(3,5-difluorophenoxy)ethyl methanesulfonate (2.20 g, 8.7 mmol, 1.0 equiv.), potassium carbonate (2.65 g, 19.2 mmol, 2.2 equiv.), 3-(fluoromethyl)azetidine hydrochloride (1.11 g, 8.8 mmol, 1.0 equiv.) in CH$_3$CN was heated at 82° C. with vigorous stirring overnight. TLC (5% MeOH/DCM) indicated a new spot and a spot that has the same Rf as the mesylate. LCMS indicated that the desired mass was present. The solid was filtered off and the filtrate was concentrated to afford a semi-solid, which was dissolved in DCM and loaded onto a silica gel column (25 g cartridge, 50-100% EA/Hex) to afford the title compound as a pale yellow oil (1.65 g, 77.1%).

$^1$H NMR (300 MHz, CDCl$_3$), δ 6.45-6.37 (m, 3H), 4.50 (dd, J=47.7, 5.4 Hz, 2H), 3.92 (t, J=5.7 Hz, 2H), 3.48 (t, J=7.2 Hz, 2H), 3.14 (t, J=4.2 Hz, 2H), 2.93-2.80 (m, 3H).

Step 4. Preparation of 2,6-difluoro-4-(2-(3-(fluoromethyl)azetidin-1-yl)ethoxy)benzaldehyde

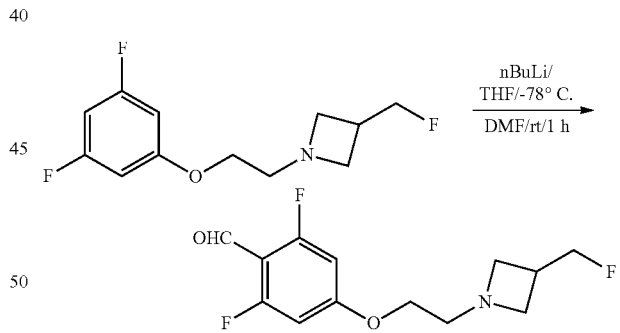

A solution of 1-(2-(3,5-difluorophenoxy)ethyl)-3-(fluoromethyl)azetidine (0.60 g, 2.4 mmol, 1.0 equiv.) in dry THF (5 mL) was cooled to −78° C. under a nitrogen atmosphere tetramethyl-ethylenediamine (3.0 mL, 20.0 mmol, 8.2 equiv.) and n-butyllithium (1.70 mL, 2.5 equiv., 1.0 equiv.) were added to the mixture and stirred at −78° C. for 30 minutes. N,N-Dimethylformamide (6.0 mL, 3.0 mmol, 1.2 equiv.) was added and the reaction was stirred at RT for 60 min. LCMS indicated the presence of the desired mass and TLC (5% MeOH/DCM) indicated there was a faint spot that has the same Rf as starting material. The reaction was quenched with water at 0° C. and extracted with EA (80 mL). The organic layer was washed with water (3×50 mL), brine, dried over anhydrous sodium sulfate, filtered and concentrated to a light yellow residue. The residue was dissolved in DCM and loaded onto a silica gel column (25 g cartridge, 0-5% MeOH/DCM) to afford the titled compound as a pale yellow thick oil. The general reference for this procedure is WO 2005/080380 pp 44; (PCT/US2005/000024 pp 44).

¹H NMR (300 MHz, CDCl₃), δ 10.19 (s, 1H), 6.48 (d, J=10.5 Hz, 2H), 4.50 (dd, J=47.7, 5.4 Hz, 2H), 3.98 (t, J=5.4 Hz, 2H), 3.48 (t, J=6.9 Hz, 2H), 3.15 (t, J=6.9 Hz, 2H), 2.91-2.80 (m, 3H).

Example 2. Preparation of 4-(2-(3-(fluoromethyl)azetidin-1-yl)ethoxy)benzaldehyde

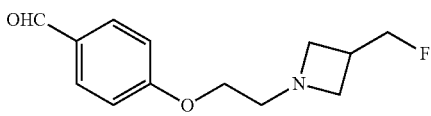 [SMILES: O=Cc1ccc(OCCN2CC(CF)C2)cc1]

Step 1. Preparation of 2-(4-formylphenoxy)ethyl methanesulfonate

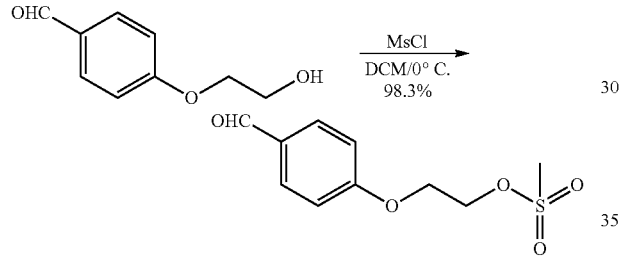

Mesyl chloride (0.50 mL, 6.5 mmol, 1.1 equiv.) was added to the solution of 4-(2-hydroxyethoxy)benzaldehyde (1.01 g, 6.1 mmol, 1.0 equiv.) and triethylamine (1.1 mL, 7.9 mmol, 1.3 equiv.) in DCM (20 mL) at 0° C. After stirring for 30 minutes, TLC (5% MeOH/DCM) indicated that the reaction was complete. Saturated sodium bicarbonate solution was added to the reaction and stirred at 0° C. for 30 minutes. The organic layer was washed with brine, dried over anhydrous sodium sulfate, filtered and concentrated. The residue was used directly without purification ¹H NMR (300 MHz, CDCl₃), δ 9.91 (s, 1H), 7.86 (d, J=8.7 Hz, 2H), 7.03 (d, J=8.1 Hz, 2H), 4.60 (t, J=4.5 Hz, 2H), 4.34 (t, J=4.5 Hz, 2H), 3.10 (s, 3H).

Step 2. Preparation of 4-(2-(3-(fluoromethyl)azetidin-1-yl)ethoxy)benzaldehyde

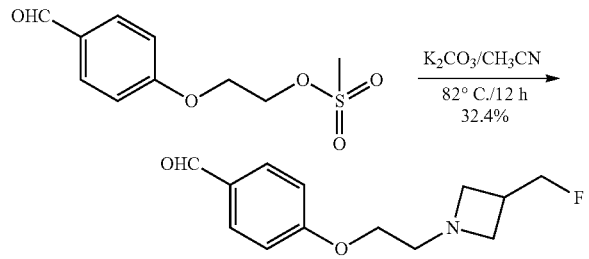

A suspension of 2-(4-formylphenoxy)ethyl methanesulfonate (1.46 g, 6.0 mmol, 1.0 equiv.), potassium carbonate (1.90 g, 13.7 mmol, 2.4 equiv.), 3-(fluoromethyl)azetidine hydrochloride (0.73 g, 5.8 mmol, 1.0 equiv.) in CH₃CN was heated at 82° C. with vigorous stirring overnight. TLC (5% MeOH/DCM) indicated a major new spot and a faint new spot less polar than the product. The reaction was cooled to ambient temperature and concentrated in vacuo. The residue was diluted with EA (100 mL) and water (50 mL). The organic layer was washed with brine, dried over anhydrous sodium sulfate, filtered and concentrated to afford a yellow residue which was dissolved in DCM and loaded onto a silica gel column (25 g cartridge, 0-5% MeOH/DCM) to afford the titled compound as a pale yellow oil (0.45 g, 32.4%). Early fractions gave recovered starting mesylate (0.35 g).

¹H NMR (300 MHz, CDCl₃), δ 9.88 (s, 1H), 7.82 (d, J=8.1 Hz, 2H), 6.98 (d, J=8.7 Hz, 2H), 4.51 (dd, J=47.4, 5.7 Hz, 2H), 4.05 (t, J=5.4 Hz, 2H), 3.50 (t, J=7.4 Hz, 2H), 3.17 (t, J=7.4 Hz, 2H), 2.89-2.85 (m, 3H).

Example 3. Preparation of 4-((1-propylazetidin-3-yl)oxy)benzaldehyde

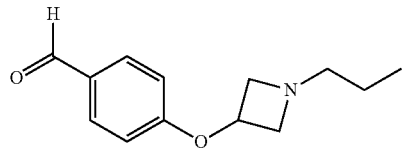 [SMILES: CCCN1CC(Oc2ccc(C=O)cc2)C1]

Step 1: Preparation of 1-propionylazetidin-3-one

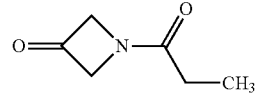

The compound 3-azetidinone hydrochloride (10.000 g, 93.0 mmol, 1.0 equiv.), anhydrous 1,2-dichloroethane (200 mL) and diisopropylethylamine (38.9 mL, 223 mmol, 2.4 equiv.) were added to a round bottom flask (500 mL) to provide a light yellow suspension. The suspension was sonicated for 1 h and then cooled to −10° C. (dry-ice/MeOH) for 10 min. Propionyl chloride (9.8 mL, 112 mmol, 1.2 equiv.) was added dropwise to the cooled suspension to provide an orange solution. The reaction was removed from the bath and stirred at room temperature for 16 h. The solvent was removed to provide a semi-solid. The semi-solid was suspended into EA (300 mL) and the suspension was filtered. The solid was rinsed with EA (2×100 mL). TLC analysis (10% MeOH/DCM, KMnO₇ stain/Heat) indicated there were three spots: Rf: 0.2, 0.5, 0.7. TLC (50% EA/Hex, KMnO₇ stain/Heat) indicated there were two spots: Rf: 1, 0.3. The filtrate was concentrated, adsorbed onto silica gel (25 g) and chromatographed through silica gel (100 g cartridge) with DCM (5 min) then 0-10% MeOH over 15 min. The product came off early from the column in DCM and continued to elute from the column with up to 10% MeOH. TLC in both solvent systems was carried out to determine if any propionyl chloride was present in early fractions. Fractions containing product were pooled and concentrated to afford the title compound as a yellow liquid (11.610 g, 98.2%).

$^1$H NMR (300 MHz, CDCl$_3$) δ: 4.80 (d, J=5.6 Hz, 4H), 2.29 (q, J=7.5 Hz, 2H), 2.01 (s, 3H), 1.18 (t, J=7.5 Hz, 3H).

Step 2. Preparation of 1-propylazetidin-3-ol

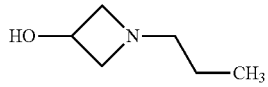

Lithium aluminum hydride (10.397 g, 273.9 mmol, 3.0 equiv.) was suspended into THF (200 mL) and cooled in an ice bath. A solution of 1-propionylazetidin-3-one (11.610 g, 91.3 mmol, 1.0 equiv.) in THF (100 mL) was added dropwise to the reaction mixture via a pressure equalizing addition funnel over 30 min. The addition funnel was removed. The flask was then fitted with a condenser and the reaction was heated at reflux in an oil bath at 75° C. for 16 h. The reaction was cooled in an ice bath for 20 min and sodium sulfate decahydrate (Glauber's salt, 25 g) was added in small portions over 20 min. After complete addition, the mixture was stirred at room temperature for 2 h. The mixture was filtered through a bed of Celite® (2 cm) and the solids rinsed with EA (2×250 mL). The clear solution was concentrated to a pale yellow liquid (9.580 g, 91.1%). NMR indicated the presence of THF and EA. This material was used without further purification in the preparation of the compounds of the examples below.

$^1$H NMR (300 MHz, CDCl$_3$) δ: 4.39 (pent, J=6 Hz, 1H), 3.62-3.56 (m, 2H), 2.90-2.85 (m, 2H), 2.41 (t, J=7.5 Hz, 2H), 1.34 (hextet, J=7.2 Hz, 2H), 0.87 (t, J=7.8 Hz, 3H).

Step 3. Preparation of 4-((1-propylazetidin-3-yl)oxy)benzaldehyde

4-Fluorobenzaldehyde (15.00 g, 120.9 mmol, 0.9 equiv.), 1-propylazetidin-3-ol (15.00 g, 130.2 mmol, 1.0 equiv.), cesium carbonate (88.40 g, 271.3 mmol, 2.1 equiv.) and N,N-dimethylformamide (284 mL) were mixed together with a Teflon™ stir bar in a 500 mL round bottomed flask. The flask was sealed and heated in a heat block at 95° C. for 6 h. The reaction was analyzed by LCMS to indicate the aldehyde was consumed. The suspension was filtered through a sintered glass funnel and the solid was washed with ethyl acetate (100 mL). The filtrate was concentrated to an orange suspension. The suspension was mixed with water (200 mL) and ethyl acetate (200 mL) and the organic layer was washed with water (3×200 mL), brine, dried over anhydrous magnesium sulfate, filtered and concentrated to an orange liquid (21.74 g, 76.1%). The material was used without further purification.

$^1$HNMR (300 MHz, CDCl$_3$), δ 9.87 (s, 1H), 7.82 (d, J=9.0 Hz, 2H), 6.86 (d, J=8.7 Hz, 2H), 4.86 (quintet, J=5.7 Hz, 1H), 3.85-3.80 (m, 2H), 3.13-3.08 (m, 2H), 2.48 (t, J=7.2 Hz, 2H), 1.46-1.34 (m, 2H), 0.91 (t, J=7.2 Hz, 3H).

Example 4: Preparation of 3-fluoro-4-((1-propylazetidin-3-yl)oxy)benzaldehyde

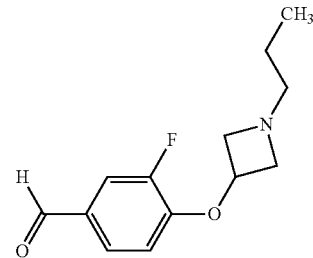 [SMILES: CCCN1CC(Oc2ccc(C=O)cc2F)C1]

A solution of 3-fluoro-4-iodobenzaldehyde (0.800 g, 3.2 mmol, 1.0 equiv.), 95.0% 1-propylazetidin-3-ol (1.261 g, 10.4 mmol, 3.3 equiv.) in butyronitrile (1 mL), 1,10-phenanthroline (0.058 g, 0.3 mmol, 0.1 equiv.), and cesium carbonate (2.294 g, 7.0 mmol, 2.2 equiv.) were added to a 48 mL glass pressure bottle. The mixture was degassed and blanketed with argon (3 times), then Cu(I) iodide (0.616 g, 3.2 mmol, 1.0 equiv.) was added. The mixture was degassed and blanketed with argon an additional 3 times. The reaction mixture was heated at 120° C. for 40 h. TLC (20% EA/Hex) indicated there was still starting material present. TLC (5% MeOH/DCM) indicated there was a new spot less polar than the starting aldehyde. The reaction was cooled to room temperature and diluted with EA and the mixture was sonicated. The mixture was filtered through a Celite® pad. The resulting dark brown residue was purified on a silica gel column (12 g, 0-10% MeOH/DCM) to provide a dark oil that contained impure product. The material was dissolved in acetonitrile and further purified on preparative HPLC (10-90% acetonitrile/H$_2$O, 20 min) to provide the title compound as a light brown oil (0.073 g, 9.6%).

$^1$H NMR (CDCl$_3$, 300 MHz) δ: 9.85 (s, 1H), 7.64-7.58 (m, 2H), 6.83 (t, J=7.9 Hz, 1H), 4.90 (t, J=5.8 Hz, 1H), 3.90-3.85 (m, 2H), 3.18-3.13 (m, 2H), 2.50 (t, J=7.5 Hz, 2H), 1.45-1.37 (m, 2H), 0.92 (t, J=7.6 Hz, 3H). LCMS: [M+1]$^+$, 238.5.

Section 2: Preparation of Compounds of Formula I

Example 5. Preparation of (R)-1-(1H-indol-3-yl)-N—((R)-1-phenylethyl)propan-2-amine

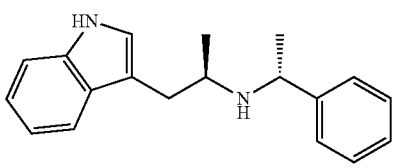 [SMILES: C[C@H](Cc1c[nH]c2ccccc12)N[C@H](C)c1ccccc1]

Indole-3-acetone (25.0 g, 144 mmol, 1.0 equiv.) was added to a solution of (R)-(+)-1-phenylethylamine (23.0 mL, 181 mmol, 1.3 equiv.) in dichloromethane (600 mL) under N$_2$ at 25° C. and the mixture was allowed to stir for 1 hr. The reaction was cooled to 0-5° C. and sodium triacetoxyborohydride (100 g, 472 mmol, 3.3 equiv.) was added over 30 minutes via powder addition funnel to the ice cooled solution. The orange solution was stirred for 1 h at 0° C. and then was allowed to warm to RT. The reaction was stirred at RT for 19 h. At this time, ESI+ indicated that no indole starting material was present. Saturated NaHCO₃ solution (100 mL) was added in 5 mL portions over 15 min at 10° C. with vigorous stirring. The solution was stirred for 15 min and sat. Na₂CO₃ solution (200 mL) was added over 15 minutes. Solid K₂CO₃ (9 g) was added in 3 g portions at which point the aqueous layer was pH 12 and bubbles had stopped forming. The layers were filtered and separated. The red organic layer was washed with sat. aq. NaHCO₃ (2×100 mL). The aqueous layers were combined and extracted with DCM (2×100 mL). The combined organic layers were dried over Na₂SO₄, filtered and concentrated to give the crude product (49 g). TLC (90:10 DCM:MeOH) showed four spots (Rf=0.63, 0.50, 0.16, 0.26), two of which were the separated diastereomeric major products (Rf=0.16 and 0.26). The crude was adsorbed onto silica gel and purified via flash chromatography (330 g cartridge, 0-100% EA:Hex). Fractions containing the R,R diastereomer were pooled and purified a second time with the same flash chromatography conditions to afford 24 g of product (~82% ee). Previous successful separation was achieved by a silica gel:crude ratio of 40:1, so the mixture was divided into 3 portions and separated on 3×330 g silica gel cartridges (0-40% EA/Hex for 20 min, isocratic 40% EA/Hex 40 min). All fractions containing the desired product were >99% diastereomerically pure. Pure fractions were concentrated and pooled to yield (R)-1-(1H-indol-3-yl)-N—((R)-1-phenylethyl)-propan-2-amine as an orange semi-solid (11.91 g, 29.6%).

¹H NMR (CDCl₃, 300 MHz) R,R diastereomer: δ 0.96 (d, J=6.6 Hz, 3H), 1.30 (d, J=6.6 Hz, 3H), 2.68 (q, J=7.2 Hz, 1H), 2.97 (m, 2H) 4.00 (q, J=6.3 Hz, 1H), 7.43-6.97 (m, 10H), 7.96 (br s, 1H). R,S diastereomer: δ 1.11 (d, J=5.7 Hz, 3H), 1.30 (d, J=5.4 Hz, 3H) 2.80 (m, 3H), 3.92 (q, J=6.9 Hz, 1H), 6.93-7.40 (m, 10H), 8.13 (br s, 1H); the aromatic region was difficult to distinguish from the R,R diastereomer due to lack of purity.

LCMS: ES+ [M+H]+ 279.0.

Example 6. Preparation of (2R)-1-(1H-indol-3-yl)propan-2-amine

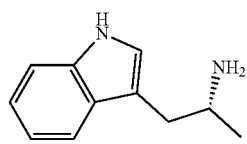

The compound (R)-1-(1H-indol-3-yl)-N—((R)-1-phenylethyl)propan-2-amine (11.91 g, 42.8 mmol, 1.0 equiv.) was dissolved in methanol (250 mL) and added to a 2 L Parr bottle and the solution was sparged with N₂ for 10 min. 20% Pd(OH)₂ on carbon wet with water (10.71 g, 76.3 mmol, 1.8 equiv.) was added and the bottle was pressurized with 50 psi of hydrogen and shaken in a Parr apparatus for 22 h, LCMS analysis indicated that the reaction was completed. The suspension was filtered through Celite® and concentrated to remove MeOH. The crude was dissolved into DCM and washed with saturated Na₂CO₃ solution (50 mL) and the aqueous layer was extracted with DCM (2×50 mL). The organic layers were combined, dried, and concentrated to yield (2R)-1-(1H-indol-3-yl)propan-2-amine as a light brown solid that did not require further purification (6.68 g, 89.6%).

¹H NMR (CDCl₃, 300 MHz) δ 1.17 (d, J=6.6 Hz, 3H), 2.66 (dd, J=8.4, 14.7 Hz, 1H), 2.88 (dd, J=5.4, 14.1 Hz, 1H), 3.27 (sextet, J=1.5 Hz, 1H), 7.05-7.22 (m, 3H), 7.37 (d, J=7.5 Hz, 1H), 7.62 (d, J=8.7 Hz, 1H), 8.00 (br s, 1H).

LCMS: ES+ [M+H]+ 174.9.

Example 7. Preparation of 2-fluoro-2-methylpropanol

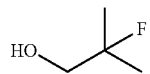

Methyl 2-fluoro-2-methylpropionate (5.01 g, 40.5 mmol, 1.0 equiv.) was added dropwise over 15 min to a stirred suspension of lithium aluminum hydride (2.50 g, 65.9 mmol, 1.6 equiv.) in anhydrous diethyl ether (100 mL) cooled in an ice bath. After 2 hours, 2.0 mL water, 2.0 mL 15% w/v NaOH, and 5.0 mL water were added sequentially dropwise. After 15 min, the white suspension was diluted with DCM, gravity filtered through Celite®, and the solids were washed with DCM. The filtrate was concentrated (200 mbar, 25° C.) to afford 2-fluoro-2-methylpropanol as a colorless oil (2.09 g, 56.1%).

¹H NMR (300 MHz, CDCl₃) δ 1.34 (d, J=21.3 Hz, 6H), 1.95 (br t, 1H), 3.56 (dd, J=6.6, 20.7 Hz, 2H).

Example 8. Preparation of 2-fluoro-2-methylpropyl trifluoromethanesulfonate

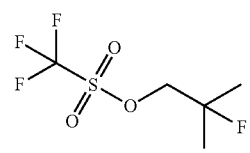

Trifluoromethanesulfonic anhydride (5.0 mL, 29.7 mmol, 1.3 equiv.) was added dropwise to a 0° C. solution of 2-fluoro-2-methylpropanol (2.090 g, 22.7 mmol, 1.0 equiv.) and 2,6 lutidine (3.40 mL, 29.4 mmol, 1.3 equiv.) in DCM (25 mL) over 30 minutes. After 2 hours, the red solution had turned light brown. TLC (20:80 EA:Hex, KMnO₄ stain) indicated that the starting material was not present. The reaction mixture was washed with 1M HCl solution (2×20 mL) and sat. NaHCO₃ solution (2×20 mL). The aqueous layers were each back extracted with DCM (20 mL). The combined organic layers were dried with Na₂SO₄, filtered and concentrated under reduced pressure (150 mbar, 25° C.) to afford 2-fluoro-2-methylpropyl trifluoromethanesulfonate as a red oil (4.39 g, 86.3%).

¹H NMR (300 MHz, CDCl₃) δ 1.46 (d, J=20.4 Hz, 6H), 4.41 (d, J=18.6 Hz, 2H). ¹⁹F NMR (282 MHz, CDCl₃) δ −147.1, −74.5.

Example 9. Preparation of (R)—N-(1-(1H-indol-3-yl)propan-2-yl)-2-fluoro-2-methylpropan-1-amine

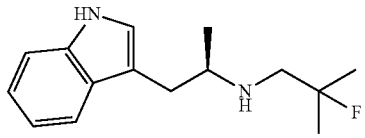 [SMILES: C[C@H](Cc1c[nH]c2ccccc12)NCC(C)(C)F]

The compound 2-fluoro-2-methylpropyl trifluoromethanesulfonate (9.587 g, 42.8 mmol, 1.1 equiv.) (solution in DCM, 16% DCM by wt %, 11.4384 g) was added to a solution of (2R)-1-(1H-indol-3-yl)propan-2-amine (6.680 g, 38.3 mmol, 1.0 equiv.), anhydrous 1,4-dioxanes (60.000 ml, 701.4 mmol, 18.3 equiv.), and freshly-distilled diisopropylethylamine (8.500 ml, 48.8 mmol, 1.3 equiv.). The dark brown solution was heated at 90° C. for 3 hours. After 3 h, LCMS indicated that a small amount of indolamine starting material was still present. TLC (10% MeOH/DCM) indicated triflate (Rf=0.54) had been used up. NMR of unused triflate SM (286-30) indicated the triflate had not decomposed overnight, so another 0.1 equiv (0.9883 g, 13% DCM wt %, 0.8563 g triflate SM) was added and the reaction was heated for 2 h at 90° C. LCMS indicated the reaction had completed and TLC (10% MeOH/DCM) showed one spot (Rf=0.24) (TLC with 50% EA/Hex, 1 streaked spot Rf<=0.12, another spot at Rf=0). EtOAc (50 mL) was added and the solution was washed with NaHCO$_3$ (2×50 mL) and the combined aqueous layer was washed with EtOAc (50 mL). The combined organic extracts were dried over Na$_2$SO$_4$ and concentrated under reduced pressure. The crude (brown oil, 14.8 g) was purified via flash silica chromatography (240 g cartridge, 0-100% EA/Hex). The desired product eluted as a long tailing peak. Pure fractions were concentrated to yield (R)—N-(1-(1H-indol-3-yl)propan-2-yl)-2-fluoro-2-methylpropan-1-amine (4.211 g, 17.0 mmol) as a dark yellow oil.

$^1$H NMR (300 MHz, CDCl$_3$) δ 1.10 (d, J=6.3 Hz, 3H), 1.34 (dd, J=3.0, 21.9 Hz, 6H), 2.68-2.95 (m, 4H), 3.02 (sextet, J=6.6 Hz, 1H), 7.05 (d, J=2.4 Hz, 1H), 7.26-7.11 (m, 2H), 7.36 (d, J=6.9 Hz, 1H), 7.62 (d, J=7.5 Hz, 1H), 8.18 (br s, 1H). $^{19}$F NMR (282 MHz, CDCl$_3$) δ -144.2. m/z: ES+ [M+H]+ 249.0.

Example 10. General Procedure for Preparation of the tetrahydro-1H-pyrido[3,4-b]indole Series 4-(2-(3-(Fluoromethyl)azetidin-1-yl)ethoxy)benzaldehyde (0.087 g, 0.4 mmol, 1.3 equiv.) was added to a solution of (R)—N-(1-(1H-indol-3-yl)propan-2-yl)-2-fluoro-2-methylpropan-1-amine (0.070 g, 0.3 mmol, 1.0 equiv.) in anhydrous toluene (1.50 mL) and glacial acetic acid (0.100 mL, 1.7 mmol, 6.2 equiv.). Molecular sieves were added and the solution was stirred under N$_2$ in the dark at 80° C. for 8 hours. The reaction solution was diluted in DCM, filtered, and washed with saturated Na$_2$CO$_3$ solution. The aqueous layer was extracted with DCM and the combined organic layers were dried over Na$_2$SO$_4$. The solution was filtered and concentrated. The residue was dissolved into acetonitrile (2 mL) and filtered through a syringe filter before purification via prep LC (40 to 90% ACN:H$_2$O over 18 min, followed by isocratic 90% ACN for 7 min). Pure fractions were concentrated and dried to afford (1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole as a white powder (32 mg, 24.3%).

Yields:

| Compound Name | % Yield |
| --- | --- |
| (1R,3R)-2-(2-fluoro-2-methylpropyl)-1-(3-fluoro-4-((1-propylazetidin-3-yl)oxy)phenyl)-3-methyl-2,3,4,9-tetrahydro-1H-pyrido[3,4-b]indole | 15.4% |
| (1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole | 21.5% |
| (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole | 11.1% |
| (1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole | 24.3% |

Analytical Data:

(1R,3R)-2-(2-fluoro-2-methylpropyl)-1-(3-fluoro-4-((1-propylazetidin-3-yl)oxy)phenyl)-3-methyl-2,3,4,9-tetrahydro-1H-pyrido[3,4-b]indole $^1$H NMR (300 MHz, CDCl$_3$) δ 0.90 (t, J=7.8 Hz, 3H), 1.10 (d, J=7.2 Hz, 3H), 1.27-1.52 (m, 8H), 2.45-2.73 (m, 6H), 3.08 (t, J=6.6 Hz, 2H), 3.29 (m, 1H), 3.78 (q, J=7.5 Hz, 2H), 4.66 (quin, J=6.0 Hz, 1H), 5.03 (s, 1H), 6.58 (t, J=8.1 Hz, 1H), 6.90 (d, J=8.1 Hz, 1H), 7.11-7.30 (m, 4H), 7.53 (d, J=7.5 Hz, 1H), 8.08 (br s, 1H). m/z: ES+ [M+H]+ 468.3.

(1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole $^1$H NMR (300 MHz, CDCl$_3$) δ 0.90 (t, J=7.5 Hz, 3H), 1.09 (d, J=7.2 Hz, 3H), 1.26-1.50 (m, 8H), 2.45-2.77 (m, 6H), 3.01 (t, J=7.2 Hz, 2H), 3.34 (m, 1H), 3.77 (m, 2H), 4.60 (quin, J=5.7 Hz, 1H), 5.03 (s, 1H), 6.64 (d, J=8.1 Hz, 2H), 7.10-7.21 (m, 5H), 7.54 (d, J=7.5 Hz, 1H), 8.19 (br s, 1H). m/z: ES+ [M+H]+ 450.2.

(1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole $^1$HNMR (300 MHz, CDCl$_3$) δ 1.10 (d, J=6.3 Hz, 3H), 1.17 (d, J=10.5 Hz, 3H), 1.24 (d, J=10.5 Hz, 3H), 2.38 (dd, J=14.7, 25.8 Hz, 1H), 2.60 (dd, J=3.9, 15.3 Hz, 1H), 2.80-2.917 (m, 4H), 3.07-3.16 (m, 3H), 3.48 (t, J=8.1 Hz, 2H), 3.67 (m, 1H), 3.90 (t, J=6.0 Hz, 2H), 4.50 (dd, J=5.7, 41.7 Hz, 2H), 5.19 (s, 1H), 6.39 (d, J=10.5 Hz, 2H), 7.09 (m, 2H), 7.22 (m, 1H), 7.50 (m, 2H). m/z: ES+ [M+H]+ 503.8.

(1R,3R)-2-(2-fluoro-2-methylpropyl)-1-(4-(2-(3-(fluoromethyl)azetidin-1-yl)ethoxy)phenyl)-3-methyl-2,3,4,9-tetrahydro-1H-pyrido[3,4-b]indole ¹HNMR (300 MHz, CDCl₃) δ 1.08 (d, J=6.6 Hz, 3H), 1.29 (d, J=21.0 Hz, 3H), 1.43 (d, J=21.6 Hz, 3H), 2.51-2.89 (m, 7H), 3.14 (t, J=6.9 Hz, 2H), 3.38 (m, 1H), 3.48 (t, J=6.9 Hz, 2H), 3.92 (t, J=5.7 Hz, 2H), 4.50 (dd, J=5.7, 47.4 Hz, 2H), 4.99 (s, 1H), 6.79 (d, J=8.1 Hz, 2H), 7.08-7.28 (m, 5H), 7.54 (d, J=6.9 Hz, 1H), 7.72 (br s, 1H). m/z: ES+ [M+H]+ 467.9.

Example 11: Preparation of 3-(4-bromo-3,5-difluorophenoxy)-1-propylazetidine

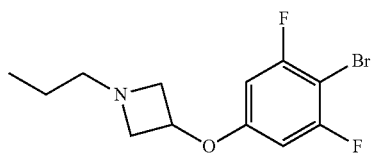 [SMILES: CCCN1CC(Oc2cc(F)c(Br)c(F)c2)C1]

To a tetrahydrofuran (10 mL) solution of 1-propylazetidin-3-ol (1.479 g, 12.8 mmol, 1.0 equiv.), 4-bromo-3,5-difluorophenol (3.220 g, 15.4 mmol, 1.2 equiv.) were added triphenylphosphine (4.042 g, 15.4 mmol, 1.2 equiv.), and diisopropyl azodicarboxylate (3.034 ml, 15.4 mmol, 1.2 equiv.) at 0 C. The resulting mixture was stirred at room temperature for 3 h. TLC analysis (5% MeOH/DCM) indicated that the starting phenol still was present with strong UV absorbance. The mixture was stirred at room temp. for an additional 12 h. The mixture was concentrated and dissolved in DCM and loaded on to a silica gel column (40 g, 0-5% MeOH/DCM). Fractions 7-13 were collected and concentrated under reduced pressure to give a white solid. 1HNMR indicated product along with triphenylphosphine oxide. The residue was dissolved in EA (100 mL) and 4 N HCl in dioxane (10 mL) was added. The mixture was stirred at room temperature overnight. The mixture was concentrated to an oil. This oil was cooled in an ice water bath and diethylether (100 mL) was added at which point a white solid formed. The mixture was sonicated and stirred. The white solid was filtered and rinsed with diethylether. The resulting solid was added sat'd sodium bicarbonate solution and EA and stirred at room temperature for 30 min and layers were separated. Organic layer was washed with brine, dried over any. sodium sulfate, filtered and concentrated to afford the title compound as a pale yellow oil.

1HNMR (300 MHz, CDCl3), δ 6.40 (d, J=7.5 Hz, 2H), 4.74-4.67 (m, 1H), 3.78 (t, J=7.2 Hz, 2H), 3.07 (dt, J=7.4, 3.0 Hz, 2H), 2.46 (t, J=7.5 Hz, 2H), 1.45-1.33 (m, 2H), 0.90 (t, J=7.5 Hz, 3H).

Example 12: Preparation of 2,6-difluoro-4-((1-propylazetidin-3-yl)oxy)benzaldehyde

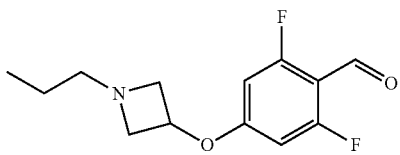 [SMILES: CCCN1CC(Oc2cc(F)c(C=O)c(F)c2)C1]

A solution of 3-(3,5-difluorophenoxy)-1-propylazetidine (0.689 g, 3.0 mmol, 1.0 equiv.) in dry THF (5 mL) was cooled to −78 C under nitrogen atmosphere. Tetramethylethylenediamine (3.451 ml, 23.1 mmol, 7.6 equiv.) and n-Butyllithium (2.000 ml, 3.0 mmol, 1.0 equiv.) were added sequentially by syringe. The mixture was allowed to stir at −78 C for 30 min. Anhydrous N,N-Dimethylformamide (7.000 ml, 3.5 mmol, 1.2 equiv.) was then added and the mixture stirred as the it warmed to room temperature over 60 min. LCMS indicated desired mass and TLC (5% MeOH/DCM) indicated the reaction was complete. The reaction mixture was cooled in an ice bath and the reaction was quenched with water. The resulting mixture was extracted with EA (80 mL). The phases were separated and the organic layer was washed with water (3×50 mL), brine, dried over any. sodium sulfate, filtered and concentrated. The light yellow residue (half) was dissolved in DCM and loaded to a silica gel plate (20×20×2 mm, 5% MeOH/DCM) to afford the title compound as a light yellow oil (0.22 g, 28.4%). The second half was dissolved in methanol and purified on a prep-HPLC to afford the title compound as a light yellow oil (161 mg).

1HNMR (300 MHz, CDCl3), δ 10.19 (s, 1H), 6.36 (d, J=9.9 Hz, 2H), 4.82-4.76 (m, 1H), 3.79 (dt, J=7.4, 2.4 Hz, 2H), 3.11 (dt, J=7.4, 2.4 Hz, 2H), 2.48 (t, J=7.5 Hz, 2H), 1.46-1.34 (m, 2H), 0.91 (t, J=7.5 Hz, 3H).

Example 13: Preparation of (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole

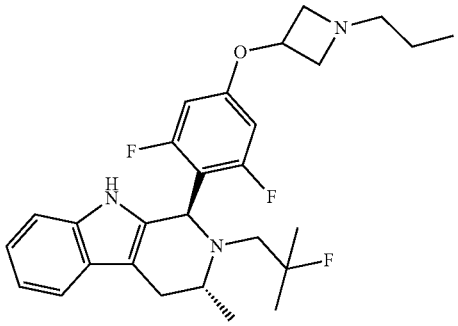 [SMILES: CCCN1CC(Oc2cc(F)c([C@@H]3c4[nH]c5ccccc5c4C[C@@H](C)N3CC(C)(C)F)c(F)c2)C1]

See Example 10, above, for the general coupling process of 2,6-difluoro-4-((1-propylazetidin-3-yl)oxy)benzaldehyde to prepare the tetrahydro-1H-pyrido[3,4-b]indole pictured above. (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole (0.030 g, 0.1 mmol) was a white solid.

1H NMR (300 MHz, CDCl3) δ 0.91 (t, J=7.5 Hz, 3H), 1.10 (d, J=6.9 Hz, 3H), 1.17 (d, J=11.7 Hz, 3H), 1.25 (d, J=11.7 Hz, 3H), 1.39 (sex, J=7.5 Hz, 2H), 2.39 (dd, J=15.3 Hz, 25.2 Hz, 1H), 2.46 (t, J=7.5 Hz, 2H), 2.61 (dd, J=3.9 Hz, 15 Hz, 1H), 2.86 (dd, J=14.7 Hz, 19.5 Hz, 1H), 3.06 (m, 3H), 3.67 (sex, J=6.3 Hz, 1H), 3.77 (dt, J=6.0 Hz, 6.3 Hz, 2H), 4.70 (quin, J=5.7 Hz, 1H), 5.20 (s, 1H), 6.27 (d, J=9.9 Hz, 2H), 7.06-7.14 (m, 2H), 7.19-7.24 (m, 1H), 7.517 (d, J=9 Hz, 1H), 7.51 (s, 1H).

| Compound Name | % Yield |
|---|---|
| (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole | 15.3% |

Demonstration of the Activity of the Compounds of the Present Invention Using Sensitive In Vitro Estrogenicity Assays Example 12

Representative compounds were tested for their inhibitory activity of estrogen according to the assay methods described in Hodges-Gallagher, L., Valentine, C. V., El Bader, S. and Kushner, P. J. (2007) "Histone Deacetylase Inhibitors Enhance the Efficacy of Hormonal Therapy Agents on Breast Cancer Cells and Blocks Anti-estrogen-Driven Uterine Cell Proliferation" Breast Cancer Res Treat, November; 105(3):297-309. Specifically, MCF-7 cells were transiently transfected with an estrogen-responsive reporter gene, ERE-tk109-Luc. Transfected cells were treated with antiestrogens in hormone-depleted medium in the presence of 100 pM 17β-estradiol (E2) for 22 hours. Luciferase activity was normalized to activity of E2 alone and $IC_{50}$'s were calculated using the least squares fit method.

A representative result for inhibition of E2-induced transcription in breast cells (nM) is shown below in tabular form:

| Compound | $IC_{50}$ |
|---|---|
| A | 2.96 |
| B | 4.35 |
| C | 10.7 |
| D | 10.0 |
| AZD9496 | 0.2 |
| Lasofoxifene | 4.6 |
| Fulvestrant | 1.4 |

Example 13

Proliferation of MCF-7 breast cancer cells was measured using Cyquant, a fluorescent DNA-binding dye (Thermo Fisher Scientific). MCF-7 cells were treated with antiestrogens in triplicate in hormone-depleted medium for 5-7 days in the presence of 100 pM E2. Fluorescent activity was normalized to the activity of E2 alone and $IC_{50}$'s were calculated using the least squares fit method.

A representative result for inhibition of E2-stimulated proliferation in breast cells (nM) is shown below in tabular form:

| Compound | $IC_{50}$ |
|---|---|
| A | 7.58 |
| B | 4.53 |
| C | 1.3 |
| D | 8.4 |
| AZD9496 | 1.3 |
| Lasofoxifene | 11 |
| Fulvestrant | 2.1 |

Example 14

Method for performing the alkaline phosphatase (AP) assay. ECC-1 cells were trypsinized and resuspended in hormone-depleted media and plated at a density of 15 k cells per well into a 96-well plate for at least 4 hours. Cells were treated with antiestrogens for 3 days and plates were subsequently frozen at −80° C. Thawed plates were incubated with a chromogenic substrate of AP, p-nitrophenyl phosphate (Thermo Fisher Scientific), for 40 minutes at 40° C. and absorbances were read at 405 nm. AP activity was normalized to the activity of E2 alone. This assay was shown to correlate with the in vivo studies comparing uterine wet weight in ovariectomized rats following treatment with a number of anti-estrogens. A representative result for induction of AP activity in uterine cells (% E2) is shown below in tabular form:

| Compound | % E2 |
|---|---|
| A | 3.96 |
| B | 2.18 |
| C | 3.1 |
| D | 3.37 |
| AZD9496 | 35 |
| Lasofoxifene | 86 |
| Fulvestrant | −0.13 |

Example 15

AP activity was assayed as in Example 13 but cells were co-treated with 500 pM E2. A representative result for inhibition of AP activity in uterine cells (% E2) observed with 100 nM antiestrogen is shown below in tabular form:

| Compound | % E2 |
|---|---|
| A | 3.15 |
| B | 1.96 |
| C | 2.5 |
| D | 4.07 |
| AZD9496 | 33 |
| Lasofoxifene | 83 |
| Fulvestrant | −2.2 |

Example 16—Detecting ER Degradation

MCF-7 cells were treated with 100 nM anti-estrogen for 24 hours in serum-free medium and protein extracts immunoblotted with D12 antibody to ERα and β-actin (Santa Cruz Biotechnology). The numbers below the blots represent the optical density of ERα bands of each treatment relative to percent vehicle after normalization to β-actin.

Figure 7:
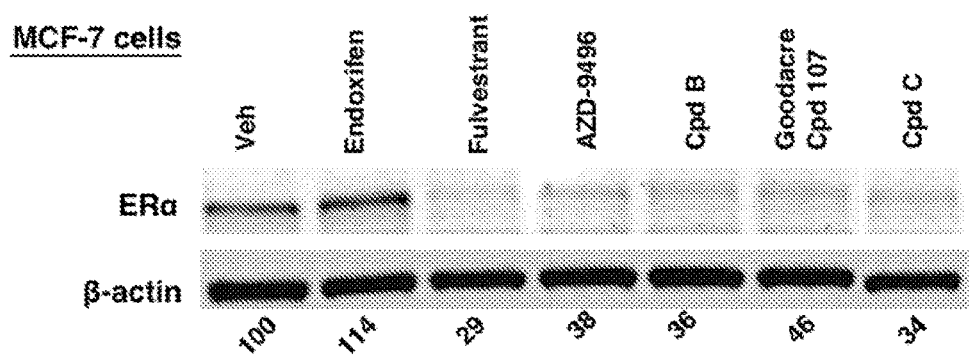
FIG. 7 is the product of an estrogen degradation assay, measuring the ability of specific compounds to degrade the estrogen receptor in MCF-7 cells.

Compound B degrades the estrogen receptor in MCF-7 Cells. See FIG. 7.

In-cell westerns were performed by treating cells as above in 96-well plates for 24 hours and immunostained with MA5-14501 antibody to ERα using the Colorimetric In-Cell ELISA kit (Thermo Fisher Scientific) according to manufacturer's instructions. $IC_{50}$'s were calculated using the least squares fit method. Error bars represent S.E.M from triplicate wells.

Compound B degrades the estrogen receptor in MCF-7 Cells. See FIG. 2.

Example 17—Xenograft Study

Xenograft studies were conducted by the Preclinical Therapeutics Core at the University of California, San Francisco in accordance with the Institutional Animal Care and Use Committee (IACUC) guidelines. Clone 18 cells (MCF7/Her2/neu) cells were grown in culture and implanted into athymic ovariectomized nu/nu mice. To stimulate tumor growth 0.36 mg estradiol 90 day release pellets (Innovative Research, Saratoga, Fla.) were implanted along with cells. When tumors reached 150-250 cubic millimeters the pellets were exchanged for 0.18 mg estradiol 90 day release pellets and divided into groups of six mice per treatment group. One of those groups received vehicle only (0.5% CMC+8% DMSO), and Compound B and Compound C each had 2 groups treated with either 10 or 100 mg/kg compound. Compounds were administered by oral gavage twice daily, except once daily on weekends/holidays for the first 21 days, and once daily after day 21. Tumors and bodyweight were measured twice weekly.

Compound B shrinks MCF-7 (HER2/neu) tumors at doses as low as 10 mg/kg. See FIGS. 5A-B.

Example 18—Pharmacokinetics

Pharmacokinetics were studied in BALB/c female mice. For each arm, three BALB/c female mice were given 5 mg/kg of compound in 0.5% CMC formulation by oral gavage. Concentration of compounds in mouse plasma and their metabolites were analyzed at each time point using LC-MS/MS. The concentrations were adjusted for the free fraction of drug in mouse plasma (method below). Area under the curve was calculated using the trapezoidal rule for 0-24 hours.

Method for Detecting Free Fraction of Drug in Plasma:

Compounds were screened for binding to human and mouse plasma (Bioreclamation, IVT) using a rapid equilibrium dialysis device (Thermo Fisher Scientific) and compounds subsequently detected by LC-MS/MS. Percent free drug equals the concentration of compound in buffer chamber divided by that in the tissue fraction chamber×100.

Compound B has high oral bioavailability and half-life in BALB/c nude mice. Compound B also exhibits better 24 hour drug exposure compared to other compounds. See FIGS. 1A-B.

Example 19—ER-α Binding

Compounds were screened for their ability to displace a fluorescent labelled tracer ERα ligand via time resolved fluorescent energy transfer using the LanthaScreen Competitive Binding Assay screening service (Thermo Fisher Scientific).

Specifically, Compounds B and C show comparable activity to fulvestrant, Goodacre Compound 102, and Goodacre Compound 107. Compounds B and C have potency similar to fulvestrant in blocking estrogen driven gene expression and proliferation of human breast cancer. See FIG. 2.

The invention claimed is:
1. A compound of Formula I:

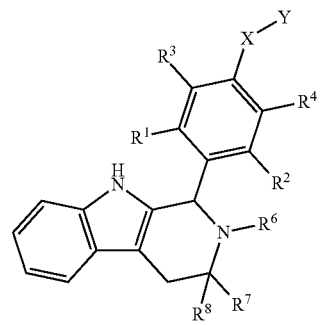

or a pharmaceutically acceptable salt thereof, wherein:
X is $CH_2$— or —O—;
Y is

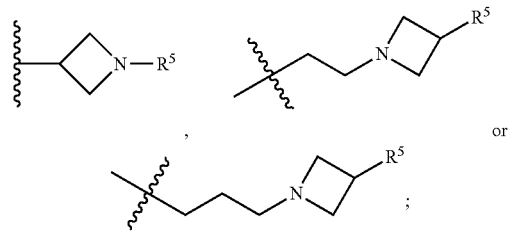

;

$R^1$ and $R^2$ are each hydrogen;
$R^3$ and $R^4$ are each independently selected from hydrogen and halo, and when one of $R^3$ or $R^4$ is halo, the other of $R^3$ or $R^4$ is hydrogen;
$R^5$ is hydrogen, $C_1$-$C_6$ alkyl, $C_1$-$C_6$ haloalkyl, $C_2$-$C_6$ alkenyl, $C_0$-$C_4$($C_3$-$C_6$ cycloalkyl), or $C_1$-$C_6$ heteroalkyl;
$R^6$ is hydrogen, $C_1$-$C_6$ alkyl, $C_1$-$C_6$ haloalkyl, or $C_0$-$C_4$ ($C_3$-$C_6$ cycloalkyl); and
$R^7$ and $R^8$ are each independently selected from hydrogen and $C_1$-$C_6$ alkyl.

2. The compound of claim 1, wherein X is —O—.
3. The compound of claim 1, wherein Y is

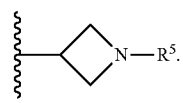

4. The compound of claim 1, wherein Y is

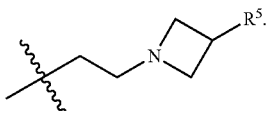

5. The compound of claim 3, wherein $R^5$ is $C_1$-$C_6$ alkyl.
6. The compound of claim 4, wherein $R^5$ is $C_1$-$C_6$ haloalkyl.

7. The compound of claim 1, wherein $R^6$ is $C_1$-$C_6$ haloalkyl.

8. The compound of claim 1, wherein $R^7$ is $C_1$-$C_6$ alkyl and $R^8$ is hydrogen.

9. The compound of claim 1, wherein the compound is of Formula I(a):

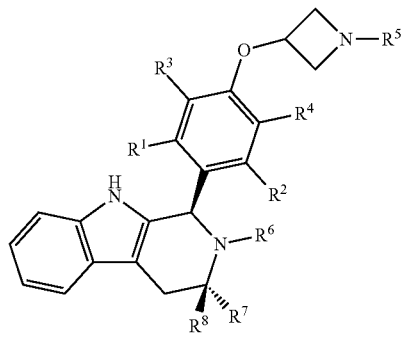

I(a)

or a pharmaceutically acceptable salt thereof.

10. The compound of claim 9, wherein $R^5$ is $C_1$-$C_6$ alkyl.

11. The compound of claim 10, wherein $R^6$ is $C_1$-$C_6$ haloalkyl.

12. The compound of claim 11, wherein $R^6$ is —$CH_2CF(CH_3)_2$.

13. The compound of claim 9, wherein $R^7$ is $C_1$-$C_6$ alkyl and $R^8$ is hydrogen.

14. The compound of claim 1, wherein the compound is of Formula I(c):

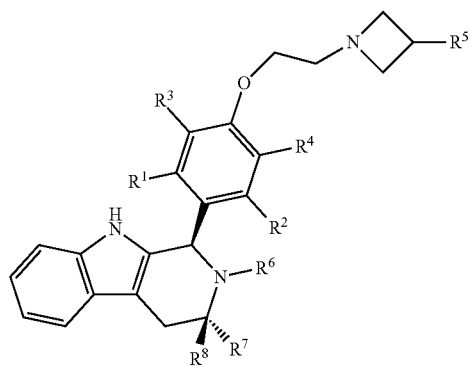

I(c)

or a pharmaceutically acceptable salt thereof.

15. The compound of claim 14, wherein $R^5$ is $C_1$-$C_6$ haloalkyl.

16. The compound of claim 15, wherein $R^5$ is —$CH_2F$.

17. The compound of claim 16, wherein $R^6$ is $C_1$-$C_6$ haloalkyl.

18. The compound of claim 17, wherein $R^6$ is —$CH_2CF(CH_3)_2$.

19. The compound of claim 18, wherein $R^7$ is $C_1$-$C_6$ alkyl and $R^8$ is hydrogen.

20. The compound of claim 1, wherein the compound is selected from:

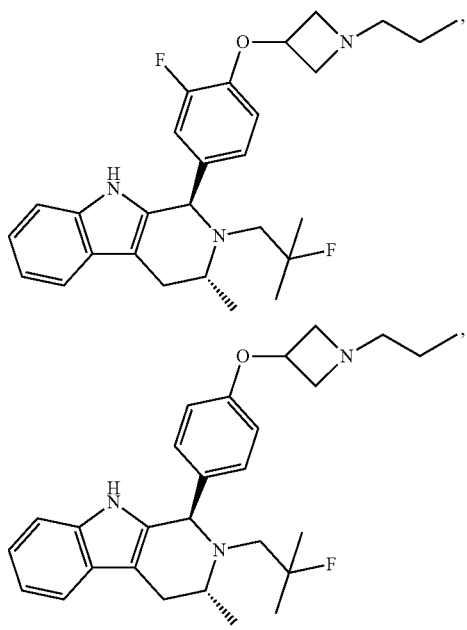

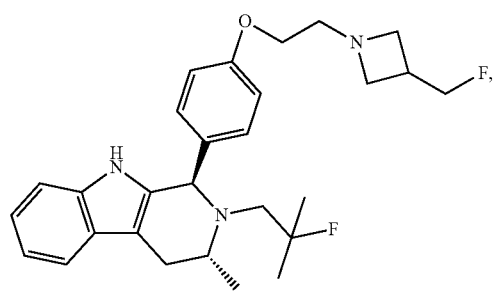

or a pharmaceutically acceptable salt thereof.

21. The compound of claim 20, wherein the compound is:

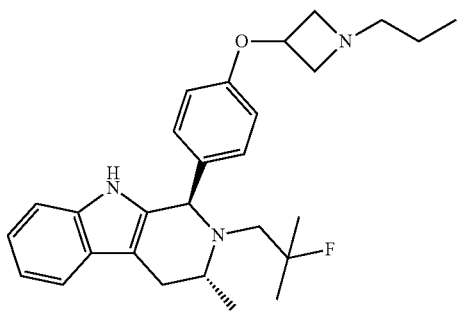 [SMILES: CCCN1CC(Oc2ccc([C@@H]3c4[nH]c5ccccc5c4C[C@@H](C)N3CC(C)(C)F)cc2)C1]

or a pharmaceutically acceptable salt thereof.

22. The compound of claim 20, wherein the compound is:

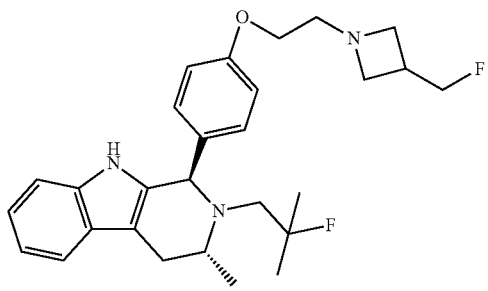 [SMILES: C[C@@H]1Cc2c([nH]c3ccccc23)[C@@H](c2ccc(OCCN3CC(CF)C3)cc2)N1CC(C)(C)F]

or a pharmaceutically acceptable salt thereof.

23. A composition comprising a compound according to claim 1 and a pharmaceutically acceptable carrier.

24. A method for treating a disorder mediated by the estrogen receptor in a patient, which comprises administering to the patient a therapeutically effective amount of the compound of claim 1, optionally in a pharmaceutically acceptable carrier.

25. The method of claim 24, wherein the disorder is selected from the group consisting of breast cancer, ovarian cancer, endometrial cancer, vaginal cancer, lung cancer, bone cancer, uterine cancer and endometriosis.

26. The method of claim 24, further comprising administering the compound in combination or alternation with another anti-cancer agent for the treatment of cancer.

27. The method of claim 24, further comprising administering the compound in combination or alternation with an estrogen or a partial estrogen receptor antagonist for the treatment of a postmenopausal disorder.

28. The compound of claim 20, wherein the compound is:

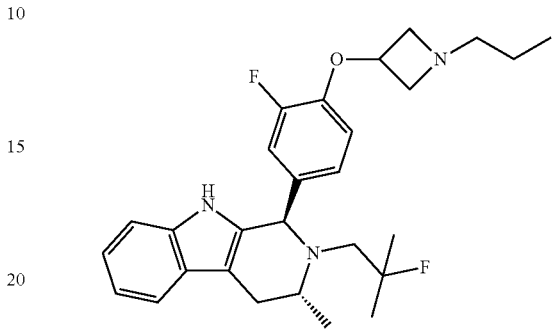

or a pharmaceutically acceptable salt thereof.

29. The method of claim 25, wherein the cancer is breast cancer.

* * * * *